(12) United States Patent
Almirante et al.

(10) Patent No.: US 7,217,733 B2
(45) Date of Patent: May 15, 2007

(54) ACE INHIBITOR DERIVATIVES

(75) Inventors: Nicoletta Almirante, Milan (IT); Ennio Ongini, Segrate (IT); Piero Del Soldato, Monza (IT)

(73) Assignee: Nicox, S.A., Sophia Antipolis - Valbonne (FR)

( * ) Notice: Subject to any disclaimer, the term of this patent is extended or adjusted under 35 U.S.C. 154(b) by 222 days.

(21) Appl. No.: 10/869,038

(22) Filed: Jun. 17, 2004

(65) Prior Publication Data

US 2005/0004100 A1  Jan. 6, 2005

(30) Foreign Application Priority Data

Jun. 19, 2003  (EP) .................. 03101796

(51) Int. Cl.
*A61K 31/40* (2006.01)
*C07D 207/00* (2006.01)

(52) U.S. Cl. ...................... 514/418; 548/400

(58) Field of Classification Search ............... 514/418, 514/400; 548/400, 418
See application file for complete search history.

(56) References Cited

U.S. PATENT DOCUMENTS 4,574,079 A * 3/1986 Gavras et al. ............ 424/1.85
6,242,432 B1 * 6/2001 del Soldato .................. 514/89

FOREIGN PATENT DOCUMENTS

| WO | 97/16405 | 5/1997 | .................. 203/4 |
| WO | 98/21193 | 5/1998 | .................. 285/10 |
| WO | WO 98/21193 | 5/1998 | |
| WO | WO 00/61537 | 10/2000 | |
| WO | WO 00/61541 | 10/2000 | |
| WO | WO 01/12584 A2 | 2/2001 | |

OTHER PUBLICATIONS

Olson et al., "Altered Glomerular Permselectivity and Progression Sclerosis Following Extreme Ablation of Renal Mass," *Kidney International* 22 112-126, 1982.
Schroth et al., "Strong Distortion of the Tetrahedral Geometry in a Spirosilicate: Molecular Structure of Bis(tetramethylethylenedioxy)silane," *Angew. Chem. Int. Ed. Engl.* 22 65-66, 1983.
Kubota et al., "Studies on Angiotensin Converting Enzyme Inhibitors. V. [1)] The Diastereoselective 2-Oxoimidazolidine Derivatives [2)]," *Chem. Pharm. Bull.* 39 1374-1377, 1991.
Wanstall et al., "Vascular Smooth Muscle Relaxation Mediated by Nitric Oxide Donors: A Comparison With Acetylcholine, Nitric Oxide and Nitroxyl Ion," *British Journal of Pharmacology* 134 463-472, 2001.
Iwanaga et al., "A Nitric Oxide-Releasing Derivative of Enalapril, NCX 899, Prevents Progressive LV Dysfunction and Improves Remodeling in Cardiomyopatic Hamsters with Heart Failure," *AHA* 75, 2002.
Iwanaga et al., "A Nitric Oxide-Releasing Derivative of Enalapril, NCX 899, Prevents Progressive LV Dysfunction and Improves Remodeling in Cardiomyopatic Hamsters with Heart Failure," *The FASEB Journal*, 2004.
Sweetman et al., "Martindale The Complete Drug Reference," *Pharmaceutical Press*.

* cited by examiner

*Primary Examiner*—Kamal A. Saeed
*Assistant Examiner*—Susannah L. Chung
(74) *Attorney, Agent, or Firm*—Arent Fox LLP

(57) ABSTRACT

ACE inhibitor nitroderivatives of formula (I):

$$A\text{---}(X_1\text{---}ONO_2)_s \qquad (I)$$

having wider pharmacological activity and enhanced tolerability. They can be employed for treating cardiovascular and renal diseases and inflammatory processes.

12 Claims, No Drawings

ACE INHIBITOR DERIVATIVES

The present invention relates to ACE inhibitor derivatives. More particularly, the present invention relates to ACE inhibitor nitroderivatives, pharmaceutical compositions containing them and their use for the treatment of cardiovascular and renal diseases, inflammatory processes, and ocular hypertension.

With ACE inhibitors a class of compounds is intended, comprising as main components Alacepril, Benazepril, Captopril, Ceronapril, Cilazapril, Delapril, Enalapril, Enalaprilat, Fosinopril, Imidapril, Lisinopril, Moexipril, Moveltipril, Perindopril, Quinapril, Ramipril, Spirapril, Temocapril and Trandolapril. They are antihypertensive drugs that act as vasodilators and reduce peripheral resistance. They inhibit angiotensin converting enzyme (ACE), which is involved in the conversion of angiotensin I to angiotensin II. Angiotensin II stimulates the synthesis and secretion of aldosterone and raises blood pressure via a potent direct vasoconstrictor effect. ACE is identical to kininase II, an enzyme that inactivates bradykinin and other potent vasodilator peptides. ACE inhibitors may reduce the degradation and increase levels of bradykinin, a potent vasodilator. ACE inhibitors are used in the treatment of heart failure, hypertension, myocardial infarction and diabetic nephropathy (Martindale, Thirty-third edition, pp. 820–825).

Now, it has been reported that ACE inhibitors have side-effects such as for example hypotension, persistent dry cough, gastrointestinal disturbances, taste disturbances, hyperkalaemia, acute renal failure, skin rashes, angioedema, and blood disorders, as already described in U.S. Pat. No. 6,218,417. Nitric salts, described in said patent, have platelet anti-aggregating activity and antihypertensive activity having reduced bronchial side effects.

U.S. Pat. No. 6,242,432 discloses derivatives of formula A—$(X_1$—$NO_2)_{to}$ having an antithrombotic activity, wherein A is the residue of ACE inhibitors, $X_1$ is a bivalent connecting bridge and $t_o$ is 1 or 2.

It was now object of the present invention to provide a specific class of ACE inhibitor derivatives able not only to eliminate or at least reduce the side effects associated with their parent compounds, but also having an improved pharmacological activity.

It has been so surprisingly found that ACE inhibitors nitroderivatives have a significantly improved overall profile as compared to native ACE inhibitors both in term of wider pharmacological activity and enhanced tolerability.

In particular, it has been recognized that the ACE inhibitor nitroderivatives of the present invention, differently from the above mentioned compounds of the prior art, exhibit an improved anti-inflammatory and antithrombotic activity and can be employed for treating or preventing acute coronary syndromes, stroke, pulmonary and ocular hypertension, hypertension, diabetic nephropathy and peripheral vascular diseases.

Object of the present invention are, therefore, ACE inhibitors nitroderivatives of general formula (I) and pharmaceutically acceptable salts or stereoisomers thereof:

A—$(X_1$—$ONO_2)_s$ (I)

wherein:
s is an integer equal to 1 or 2;
A is selected from the following groups:

1a)

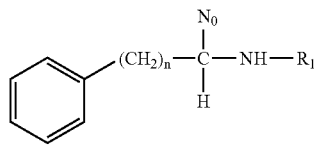

wherein n is an integer from 1 to 6, preferably equal to 1 or 2; $N_0$=—$COOR_0$ wherein $R_0$ is H or a linear or branched ($C_1$-$C_{10}$)-alkyl, or —COO— i.e. it has a free valance capable of binding $X_1$;

$R_1$ can be:

(II)

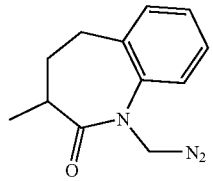

(III)

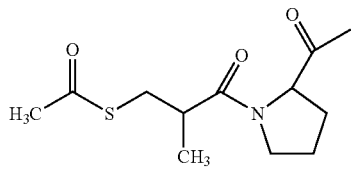

(IV)

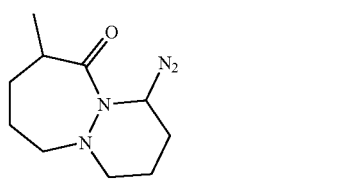

(V)

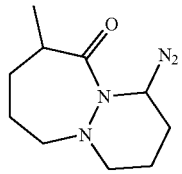

(VI)

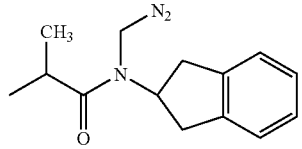

(VII)

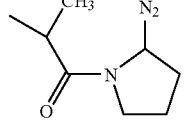

(VIII)

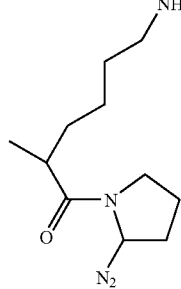

(IX)

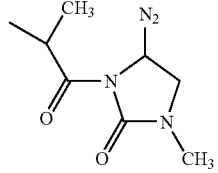

-continued

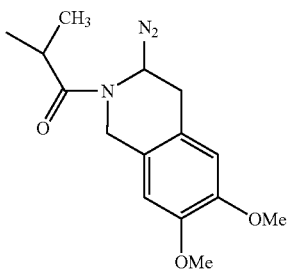
(X)

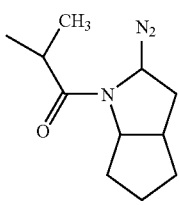
(XI)

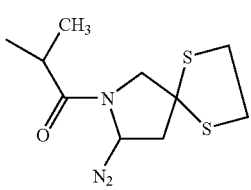
(XII)

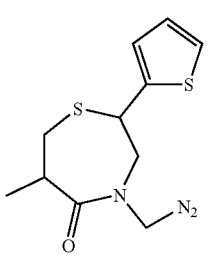
(XIII)

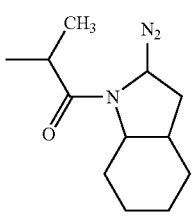
(XIV)

wherein $N_2$ has the same meanings as defined for $N_0$ and they may be equal or different, $N_{2a}$=H, —C(O)—, —COO—, —COOR$_o$, —C(O)R$_0$— wherein $R_0$ is linear or branched ($C_1$–$C_{10}$)-alkyl; with the proviso that at least one of the groups $N_0$, $N_2$ or $N_{2a}$ is —COO— or —C(O)— i.e. it has a free valence capable of binding to $X_1$;

1b)

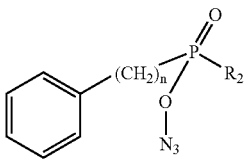

wherein n is defined above, preferably equal to 4; $N_3$ is H or

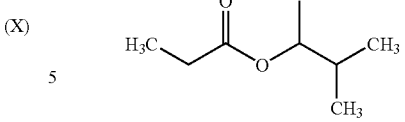
(XV)

$R_2$ can be:

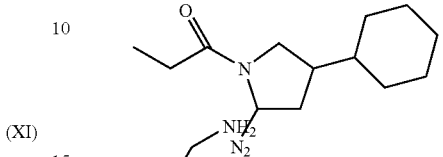
(XVI)

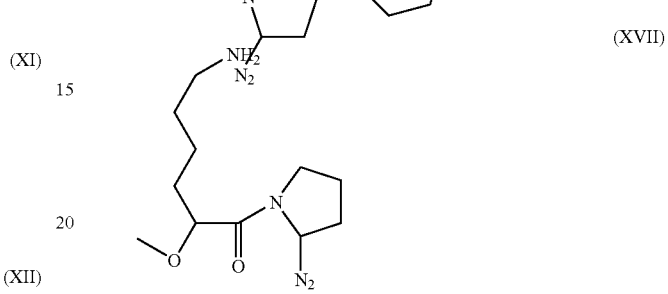
(XVII)

wherein $N_2$ is equal to —COO—, that has a free valence capable of binding to $X_1$;

1c)

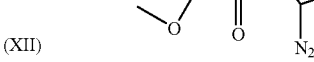
(XVIII)

wherein $R_{1c}$ is chosen from H, —COCH$_3$, or

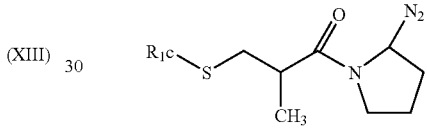
(XIX)

wherein $N_2$ is equal to —COO—, that has a free valence capable of binding to $X_1$;

1d)

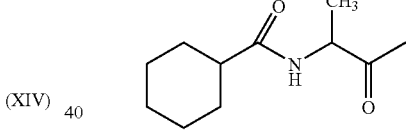
(XX)

wherein $N_2$ is as above defined, with the proviso that at least one of the groups $N_2$ is equal to —COO—, i.e. it has a free valence capable of binding to $X_1$;

$X_1$ is a linear or when possible branched ($C_1$–$C_6$)-alkylene optionally substituted with at least an halogen atom, preferably having from 3 to 5 carbon atoms or $X_1$ is a bivalent radical equal to —(CH$_2$—CH$_2$—O)$_2$— or —(CH$_2$—CH$_2$—S)$_2$—; provided that when A is the group 1a) and $R_1$ is the group of formula (III) or A is the group 1c) and $R_{1c}$ is —COCH$_3$, $X_1$ is different from a linear or when possible branched $C_1$–$C_6$ alkylene.

As stated above, the invention includes also the pharmaceutically acceptable salts of the compounds of formula (I) and stereoisomers thereof.

Examples of pharmaceutically acceptable salts are either those with inorganic bases, such as sodium, potassium, calcium and aluminium hydroxides, or with organic bases, such as lysine, arginine, triethylamine, dibenzylamine, piperidine and other acceptable organic amines.

The compounds according to the present invention, when they contain in the molecule one salifiable nitrogen atom, can be transformed into the corresponding salts by reaction in an organic solvent such as acetonitrile, tetrahydrofuran with the corresponding organic or inorganic acids.

Examples of organic acids are: oxalic, tartaric, maleic, succinic, citric acids. Examples of inorganic acids are: nitric, hydrochloric, sulphuric, phosphoric acids. Salts with nitric acid are preferred.

The compounds of the invention which have one or more asymmetric carbon atoms can exist as optically pure enantiomers, pure diastereomers, enantiomers mixtures, diastereomers mixtures, enantiomer racemic mixtures, racemates or racemate mixtures. Within the object of the invention are also all the possible isomers, stereoisomers and their mixtures of the compounds of formula (I).

It was found that the ACE inhibitor nitroderivatives of the present invention release NO with a different kinetic pattern respect to the ACE inhibitors nitroderivatives of the prior art, this different NO release allows to prevent side-effects (i.e. hypothension) and to prolong the pharmacological effect.

Preferred compounds are those of formula (I) wherein:

s is as above defined;

A is the following group:

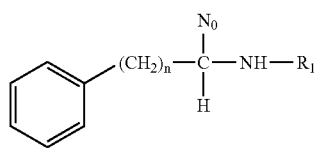

wherein n is 2; $N_0$=—COO— or —COOR$_0$ wherein R$_0$ is H or $(C_1-C_6)$-alkyl;

R$_1$ can be:

(V)

(VI)

(VII)

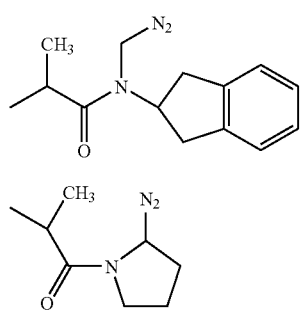

(VIII)

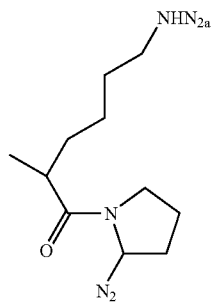

(IX)

(X)

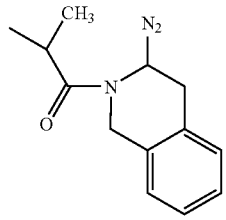

(XI)

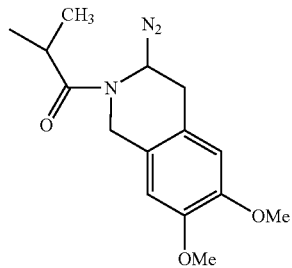

(XII)

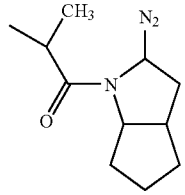

(XIV)

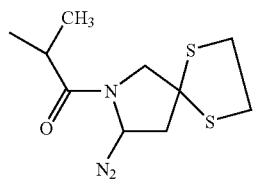

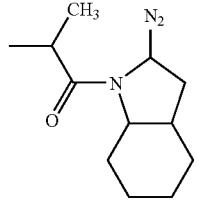

wherein $N_2$ has the same meanings as defined for $N_0$ and they may be equal or different, $N_{2a}$ is H, —C(O)—, —COO— or COOR$_0$ wherein R$_0$ is H or $(C_1-C_6)$-alkyl; with the proviso that at least one of the groups $N_0$, $N_2$, or $N_{2a}$ is —COO— or —C(O)— i.e. it has a free valence capable of binding to $X_1$;

$X_1$ is a linear $(C_3-C_5)$-alkylene or a bivalent radical equal to —(CH$_2$—CH$_2$—O)$_2$— or —(CH$_2$—CH$_2$—S)$_2$—.

Other preferred compounds are those of formula (I) wherein:
s is 1;
A is the following group:

1a)

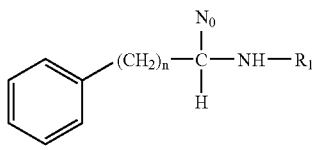

wherein n is 1, $N_0$=—COO— that has a free valence capable of binding to $X_1$ and $R_1$ is (III)

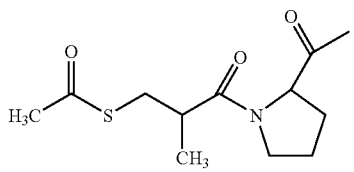

$X_1$ is a bivalent radical equal to —(CH$_2$—CH$_2$—O)$_2$— or —(CH$_2$—CH$_2$—S)$_2$—;

Other preferred compounds are those of formula (I) wherein:
s is 1;
A is the following group:

1c)

(XVIII)

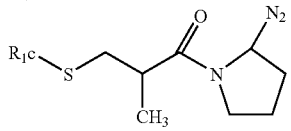

wherein $R_{1c}$ is H or —COCH$_3$, $N_2$ is equal to —COO—, that has a free valence capable of binding to $X_1$;
$X_1$ is a bivalent radical equal to —(CH$_2$—CH$_2$—O)$_2$— or —(CH$_2$—CH$_2$—S)$_2$—;
or $R_{1c}$ is (XIX)

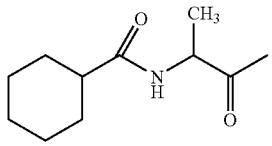

wherein $N_2$ is equal to —COO—, that has a free valence capable of binding to $X_1$;
$X_1$ is a linear (C$_3$–C$_5$)-alkylene or a bivalent radical equal to —(CH$_2$—CH$_2$—O)$_2$— or —(CH$_2$—CH$_2$—S)$_2$—.

The following are preferred compounds according to the present invention:

(1)

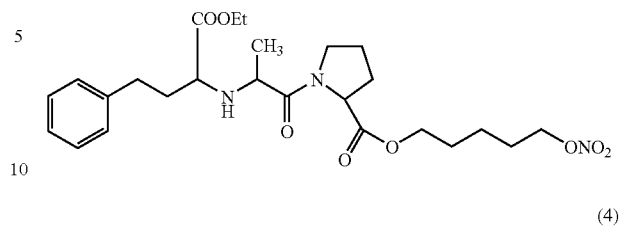

(2)

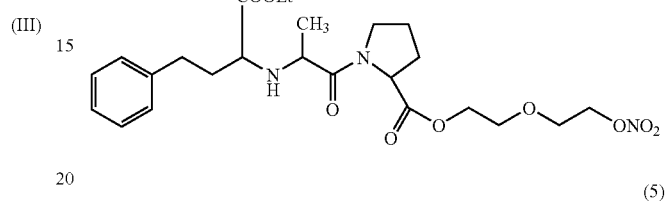

(3)

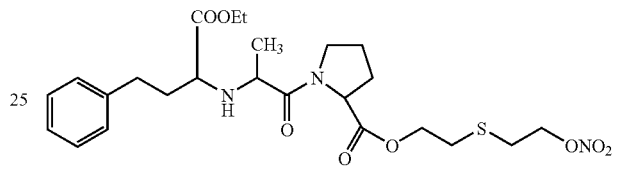

(4)

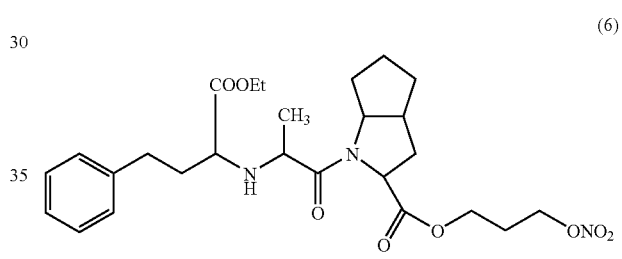

(5)

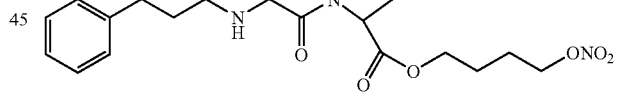

(6)

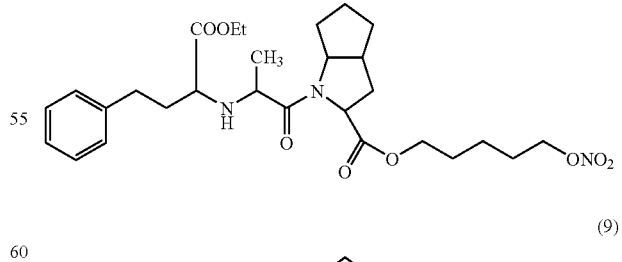

(7)

(8)

(9)

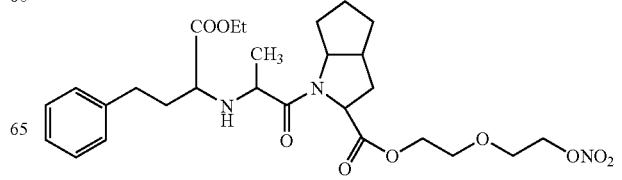

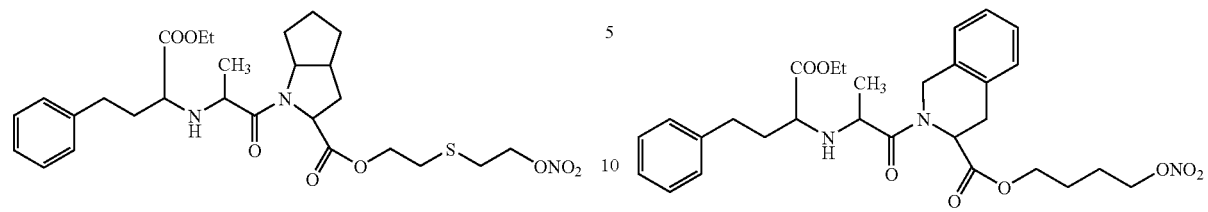
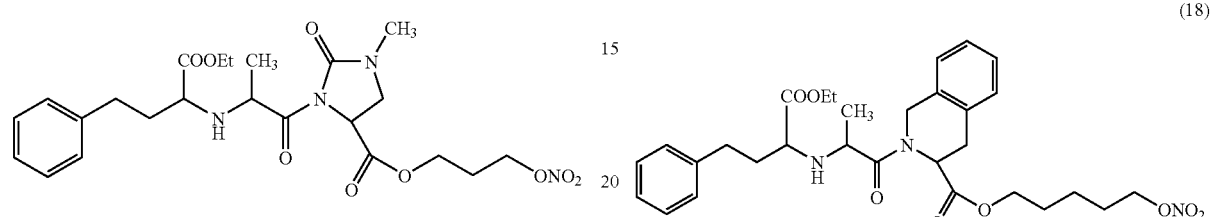
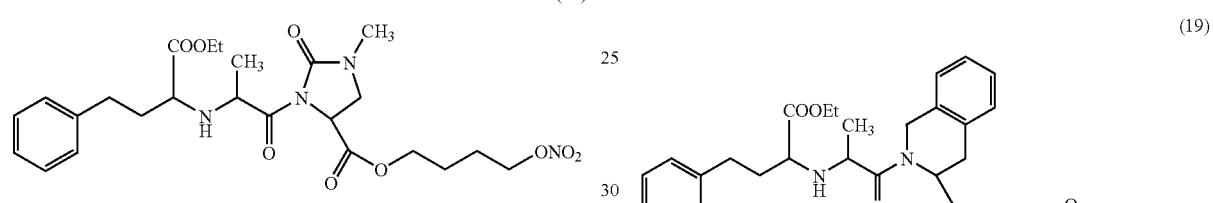
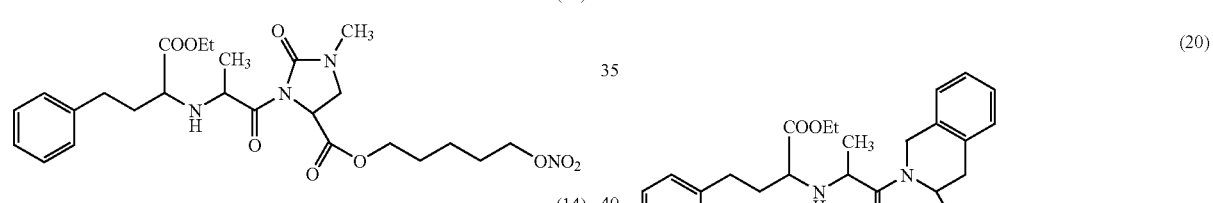
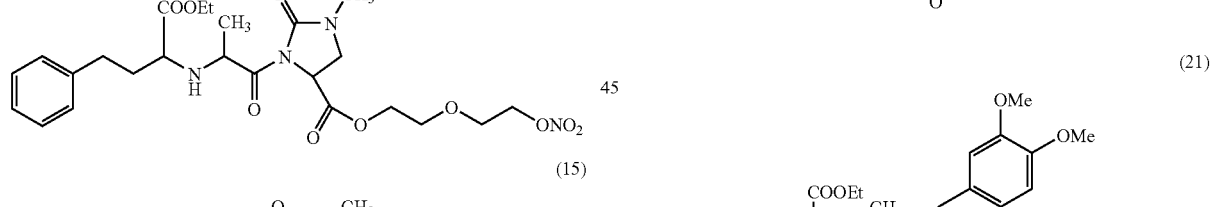
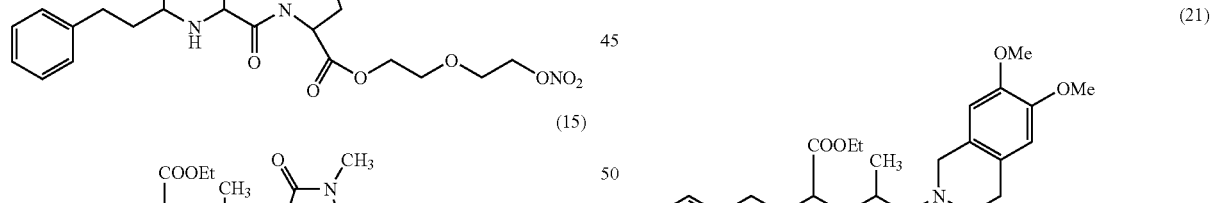
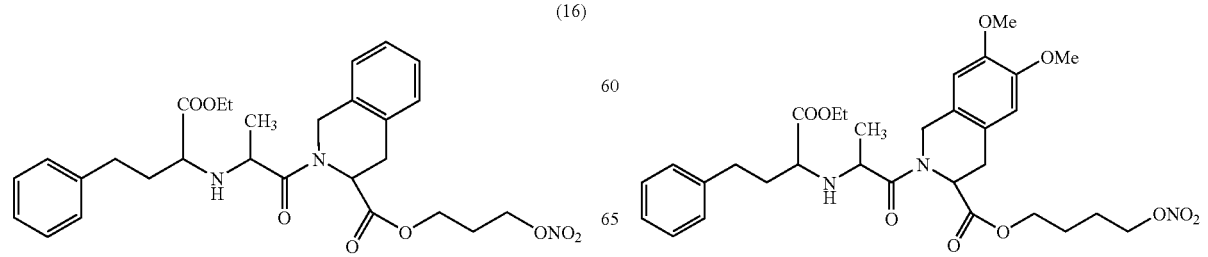

-continued
(23)
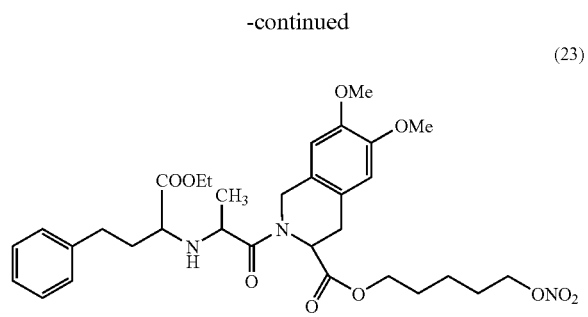
(24)
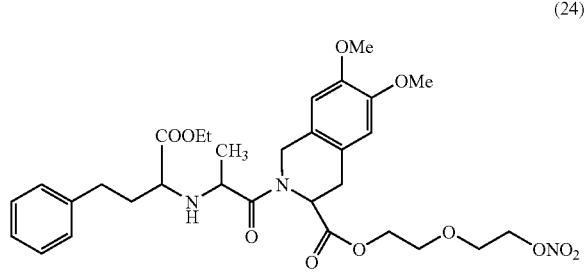
(25)
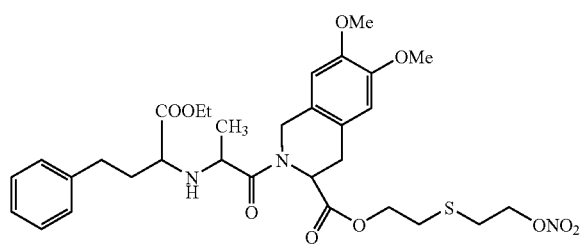
(26)
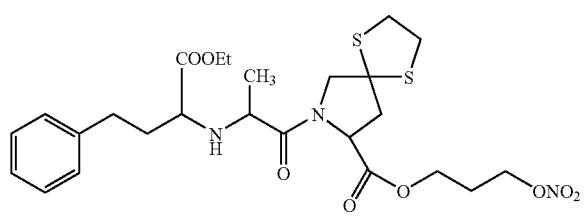
(27)
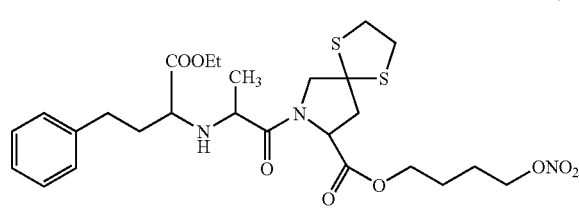
(28)
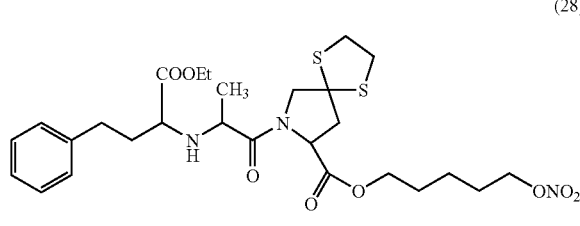
-continued
(29)
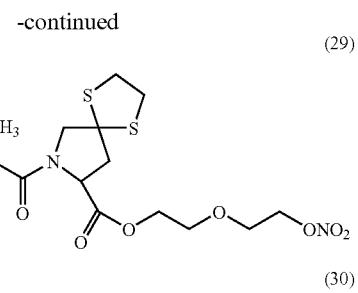
(30)
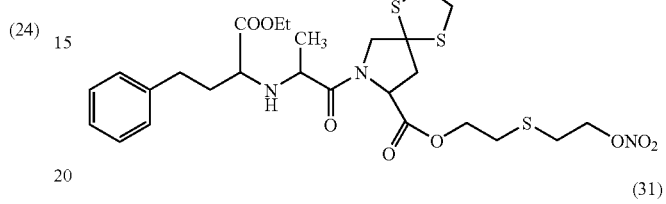
(31)
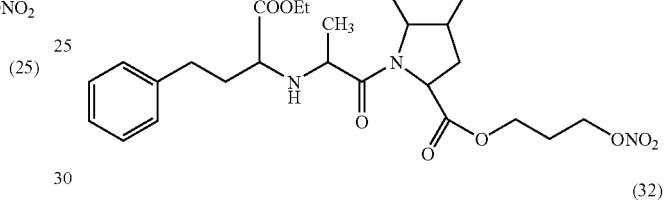
(32)
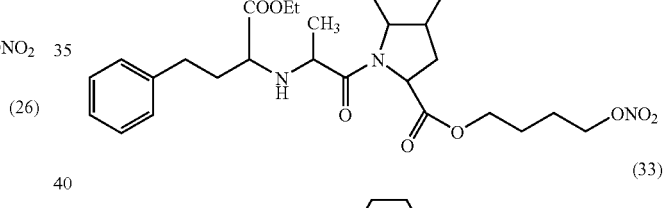
(33)
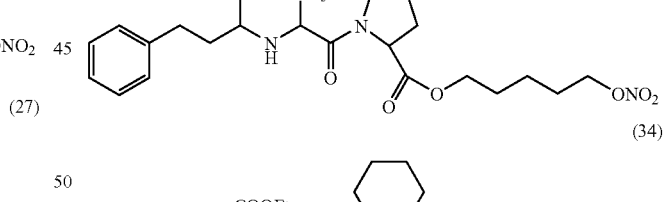
(34)
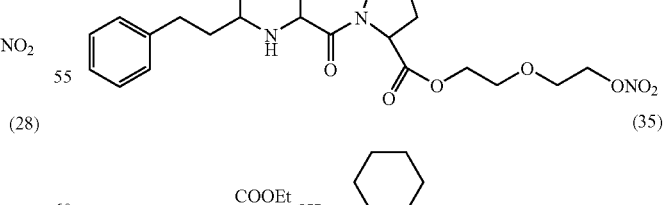
(35)

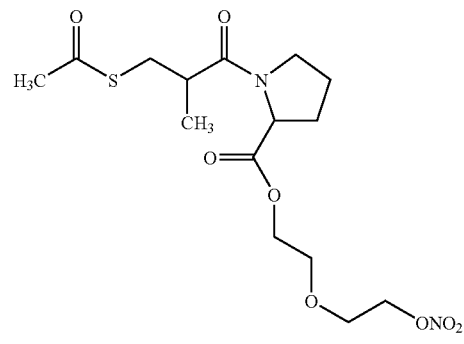
(39)
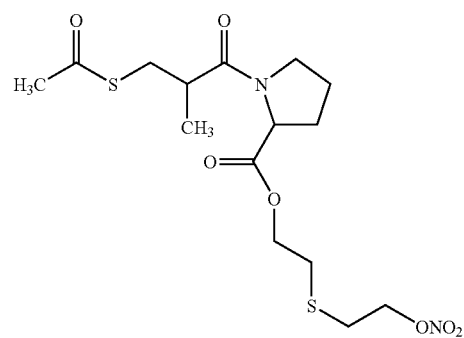
(40)
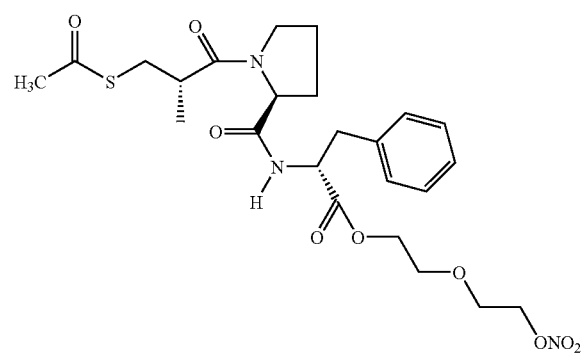
(44)
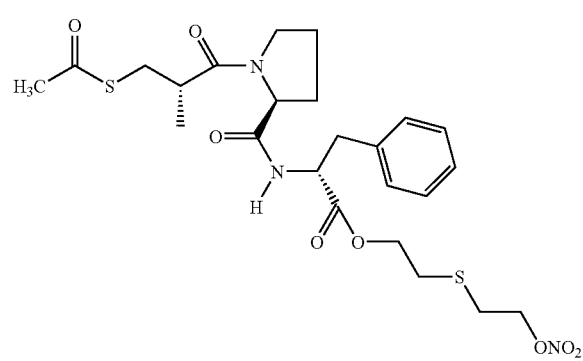
(45)
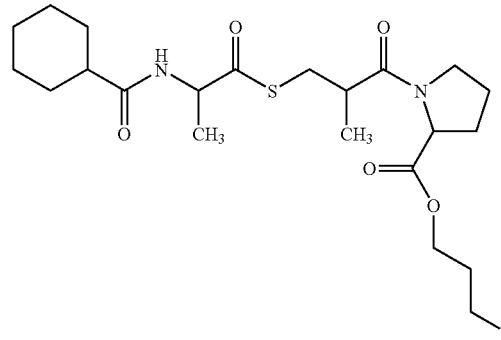
(46)
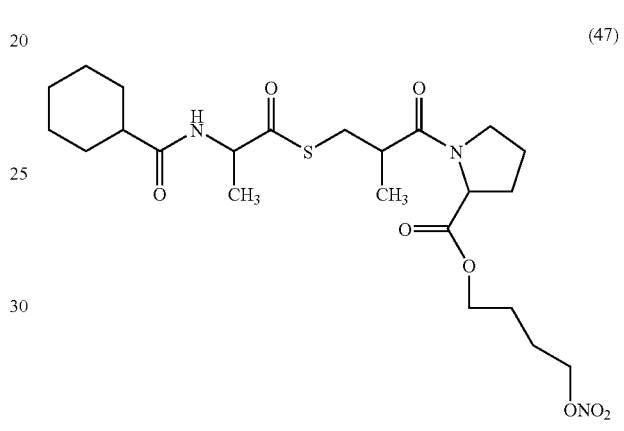
(47)
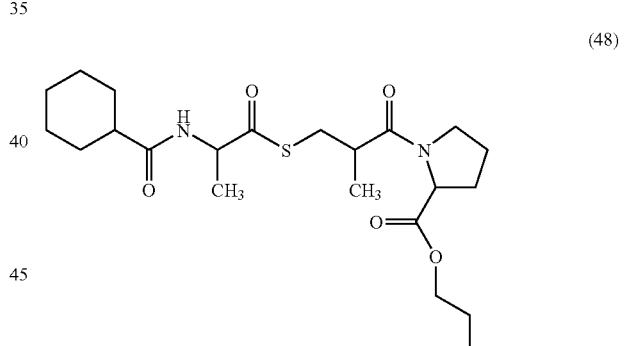
(48)
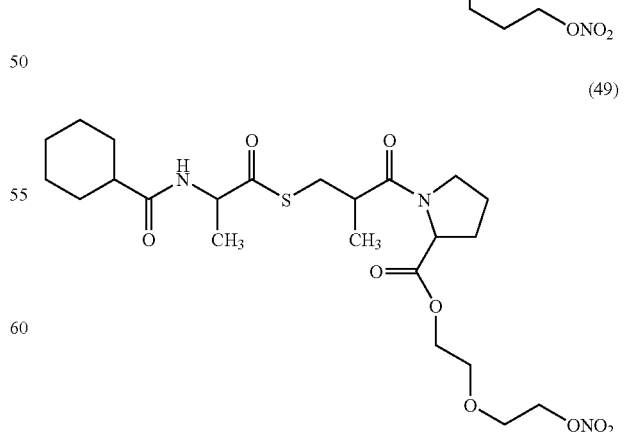
(49)

(50)
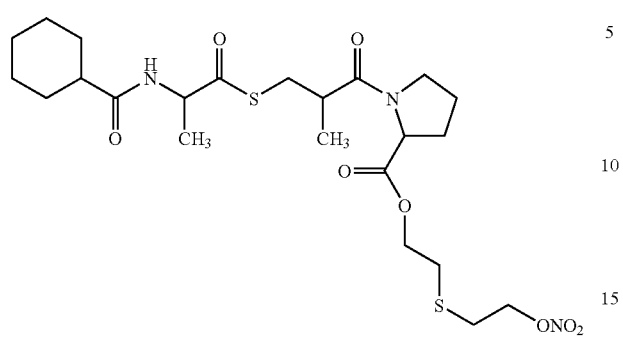
(51)
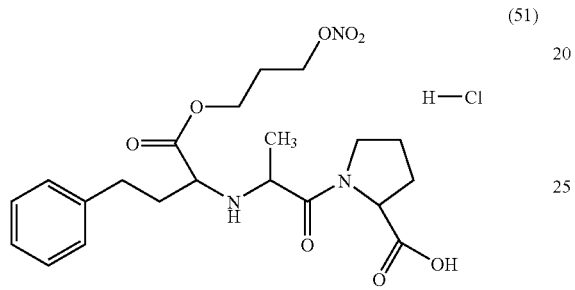
H—Cl
(52)
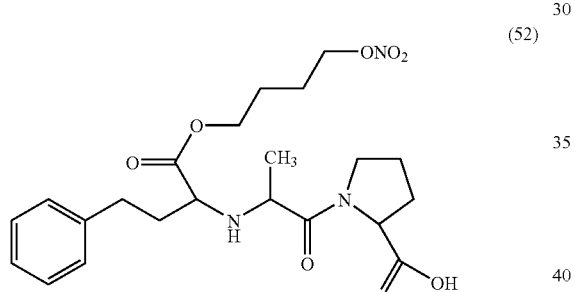
(53)
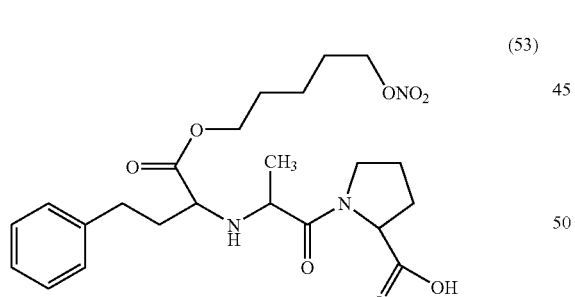
(54)
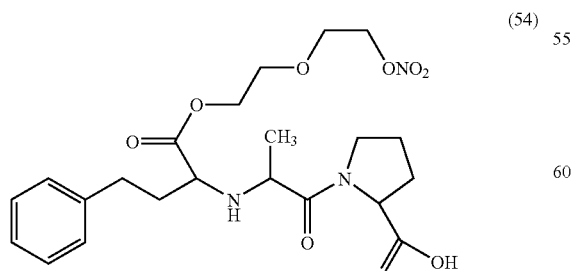
(55)
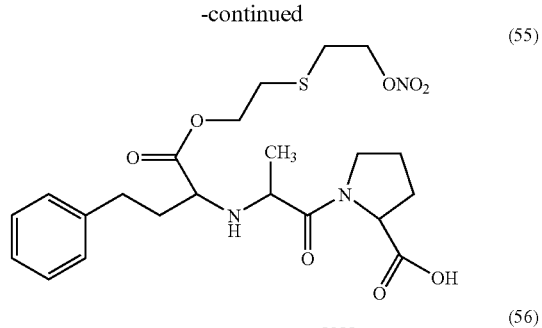
(56)
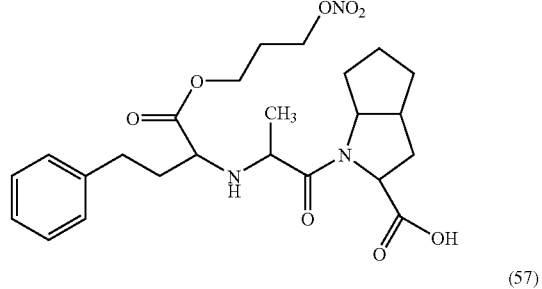
(57)
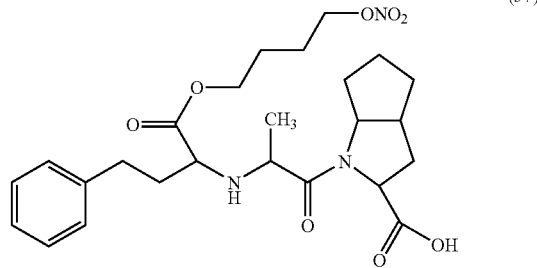
(58)
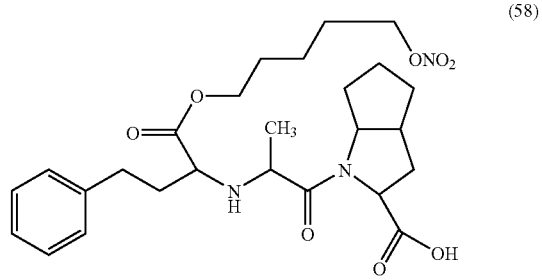
(59)
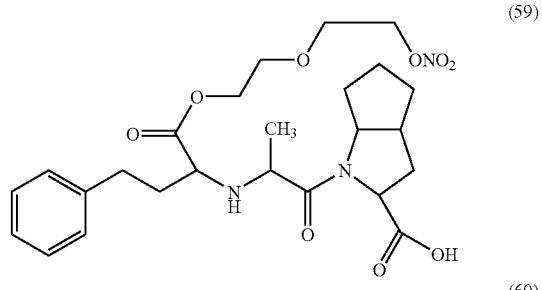
(60)
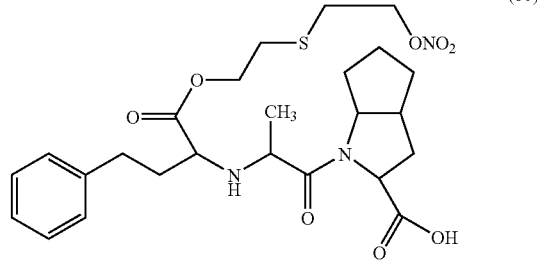

-continued
(61)
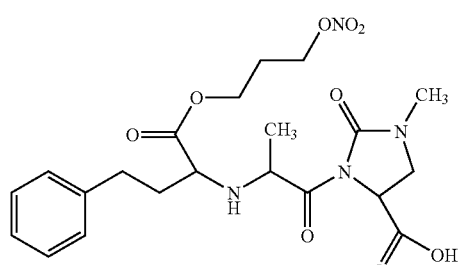
(62)
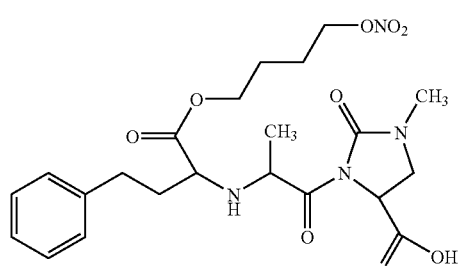
(63)
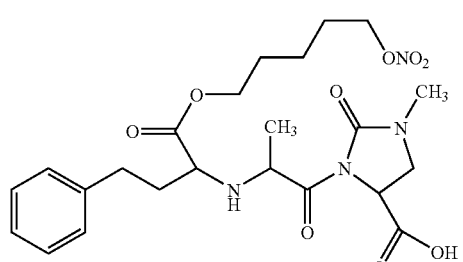
(64)
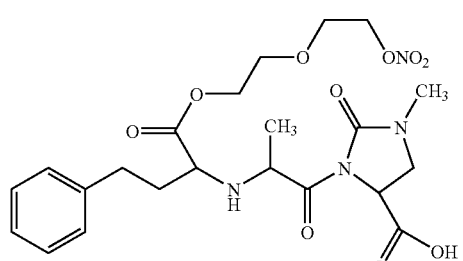
(65)
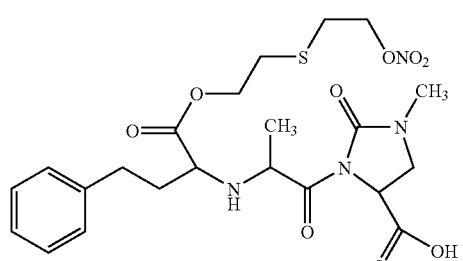
(66)
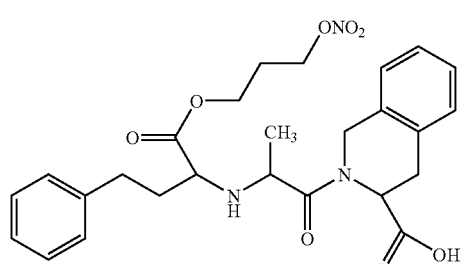
-continued
(67)
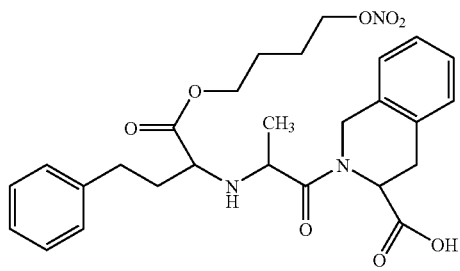
(68)
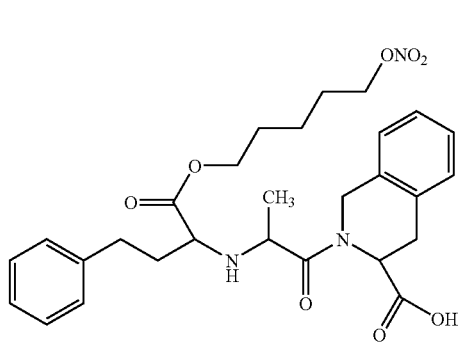
(69)
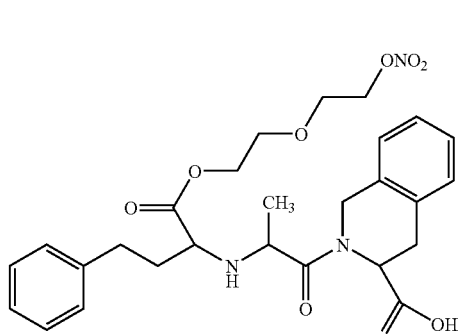
(70)
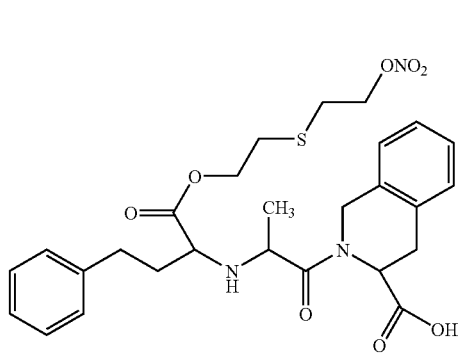
(71)
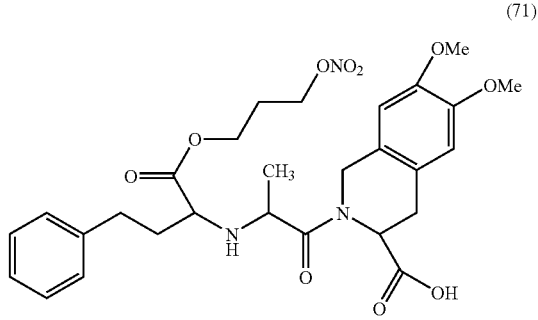

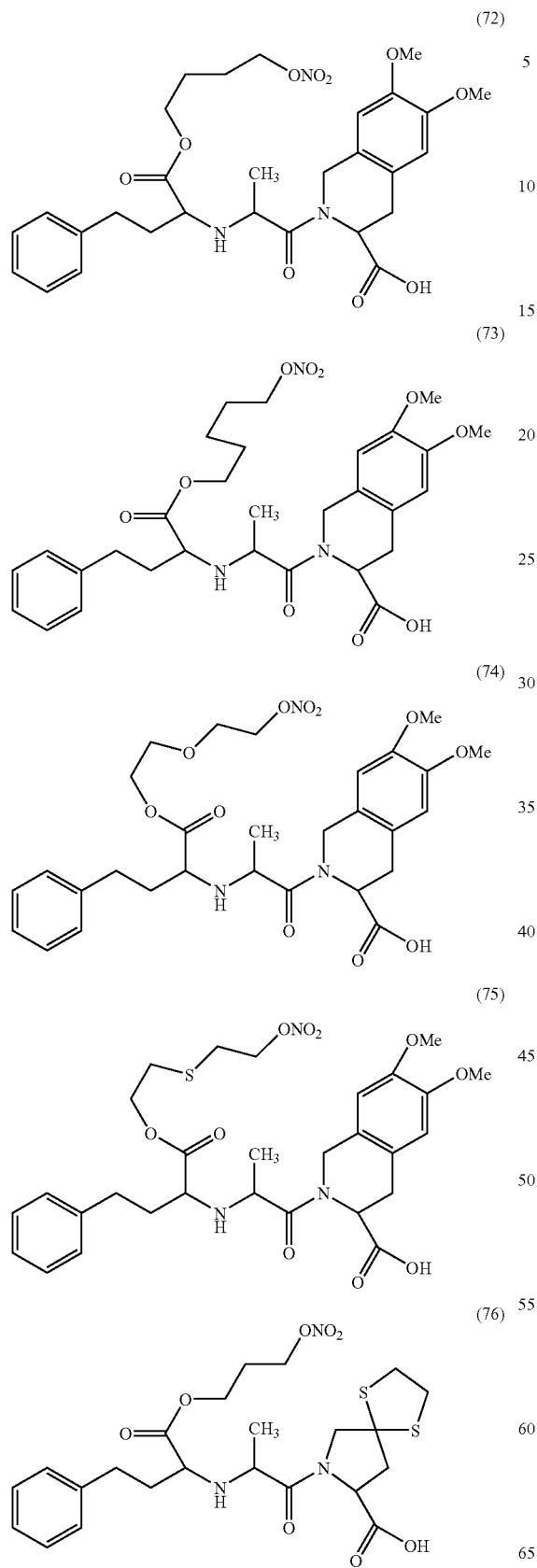

-continued
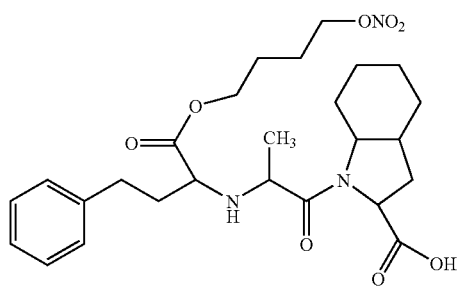
(82)
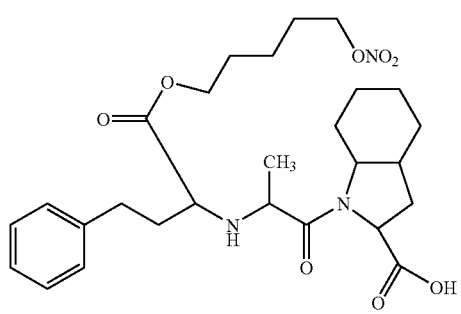
(83)
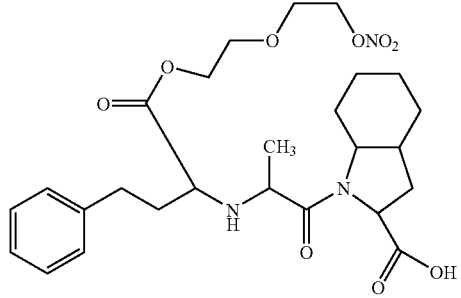
(84)
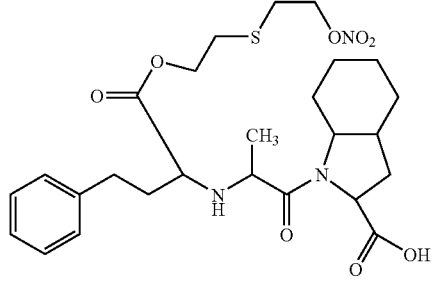
(85)
-continued
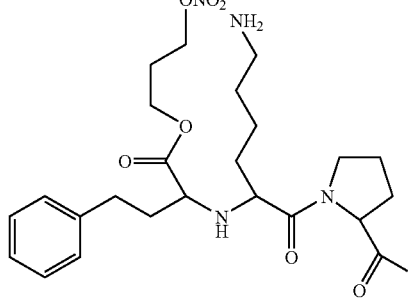
(86)
(87)
(88)
(89)

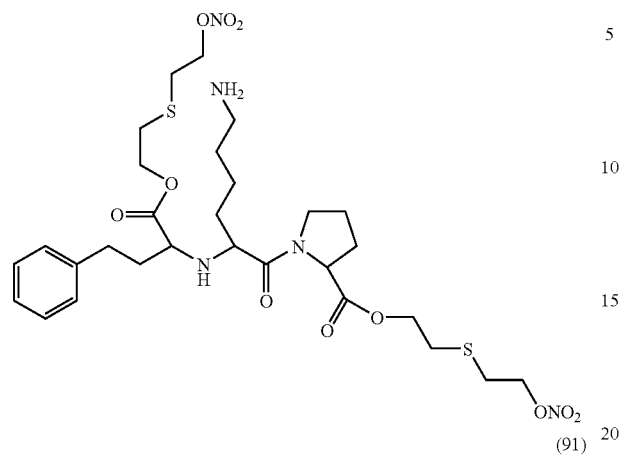
(90)
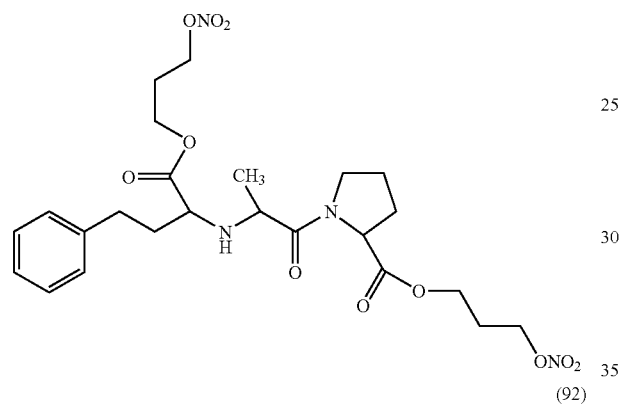
(91)
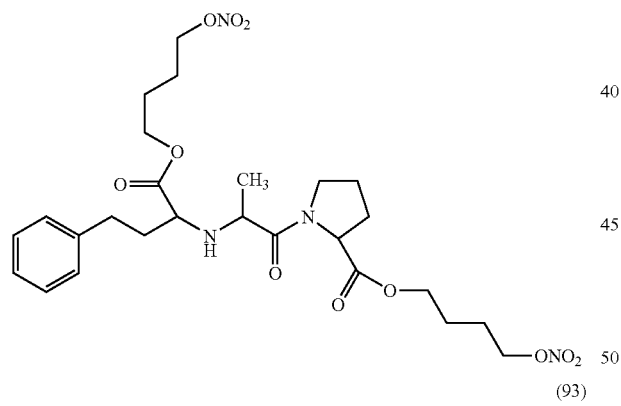
(92)
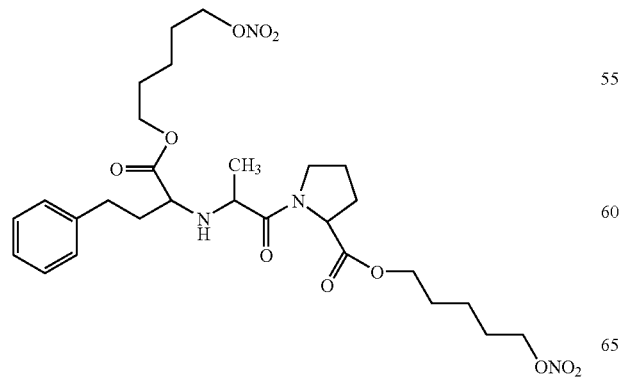
(93)
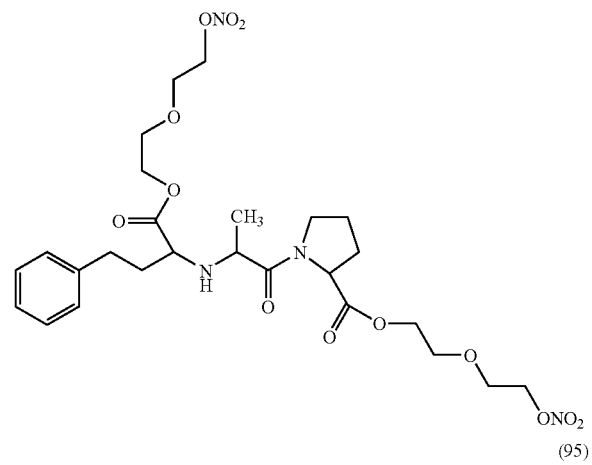
(94)
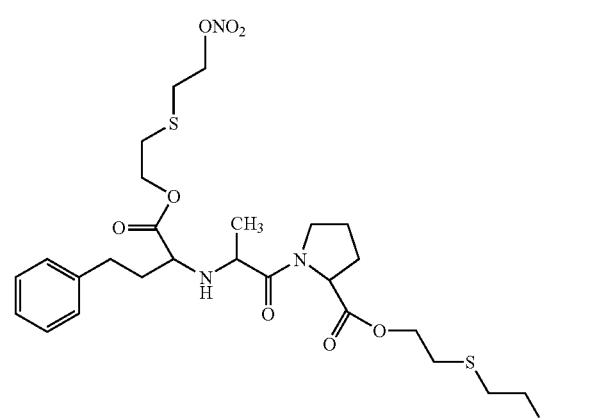
(95)
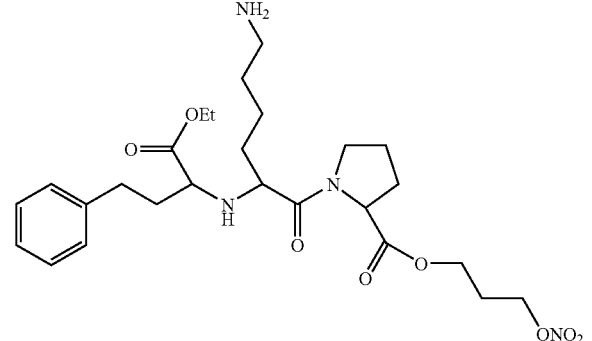
(96)
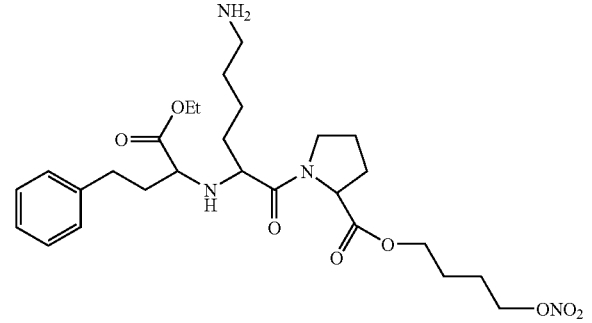
(97)

-continued
(98)
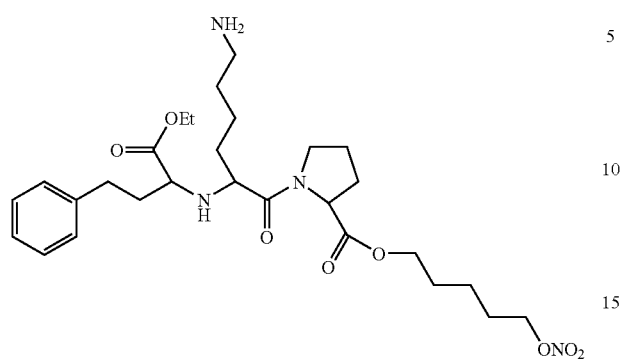
(99)
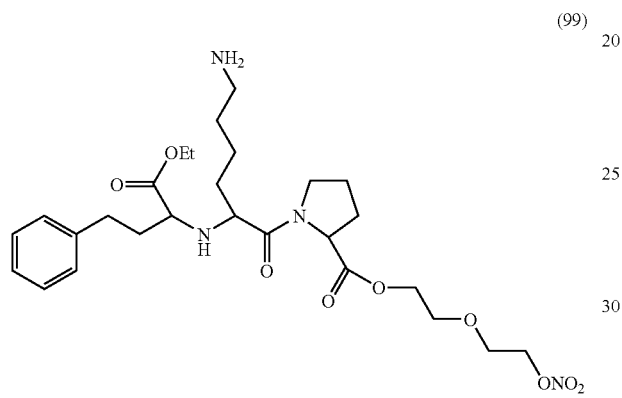
(100)
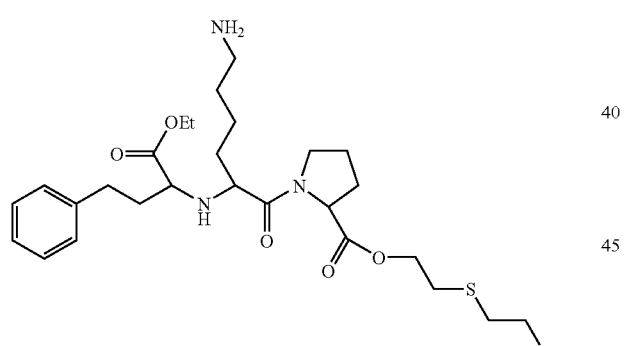
(101)
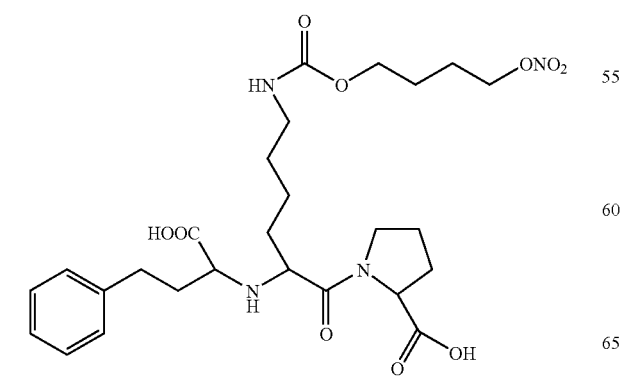
-continued
(102)
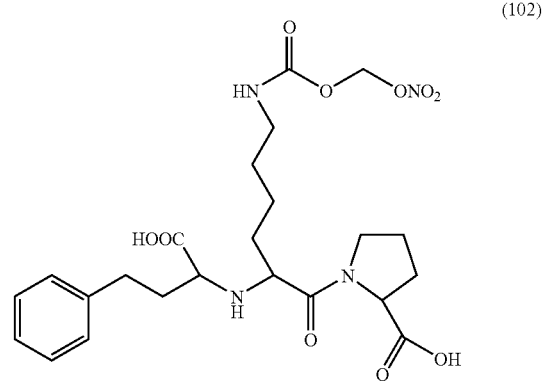
(103)
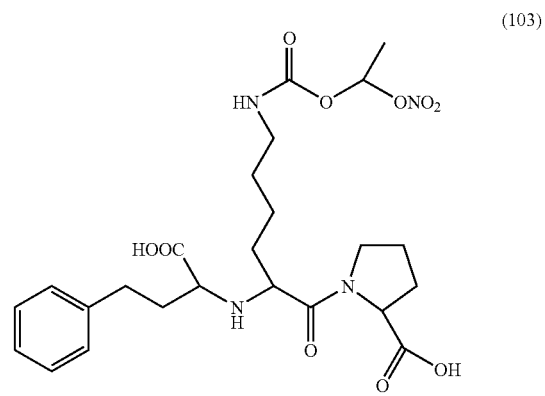
(104)
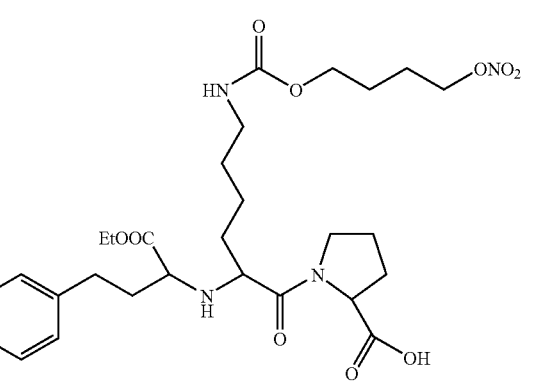
(105)
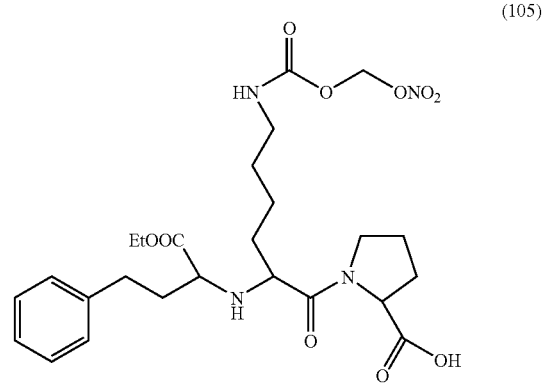

-continued
(106)
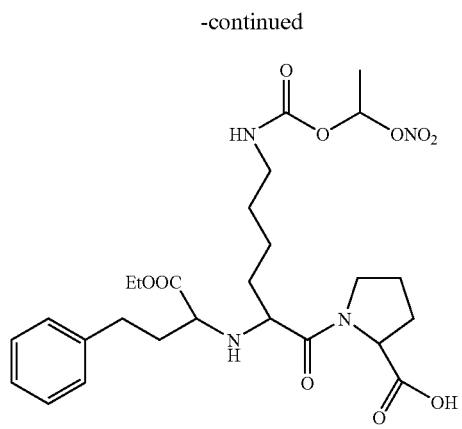
(107)
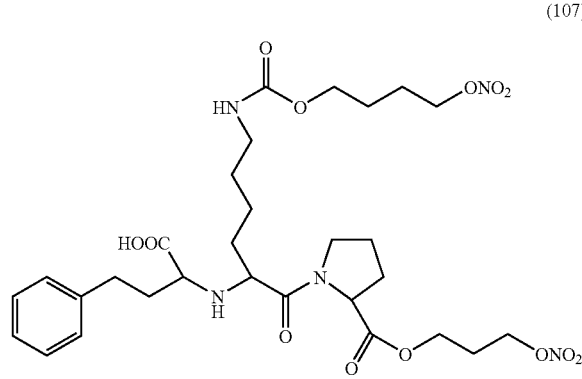
(108)
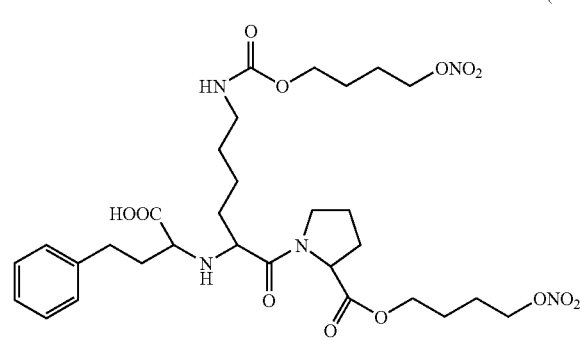
(109)
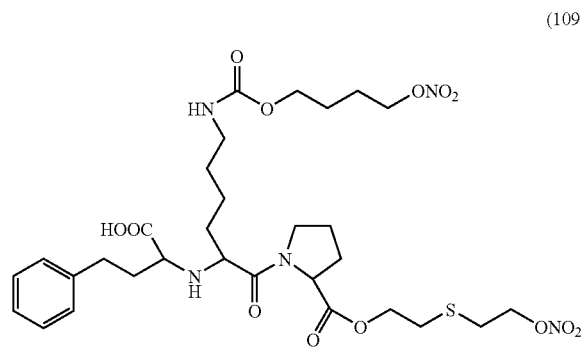
-continued
(110)
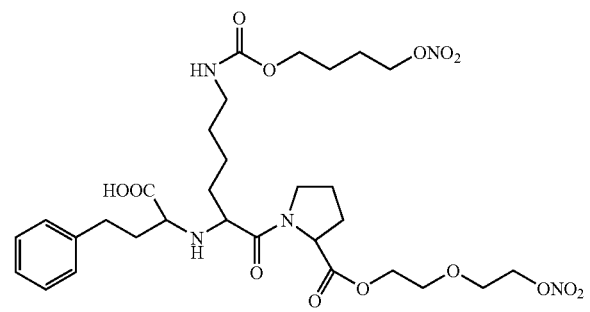
(111)
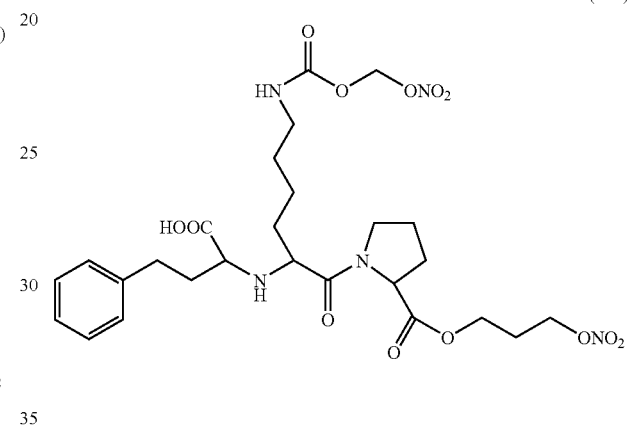
(112)
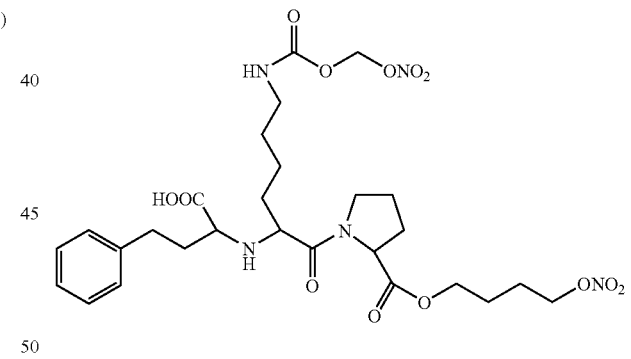
(113)
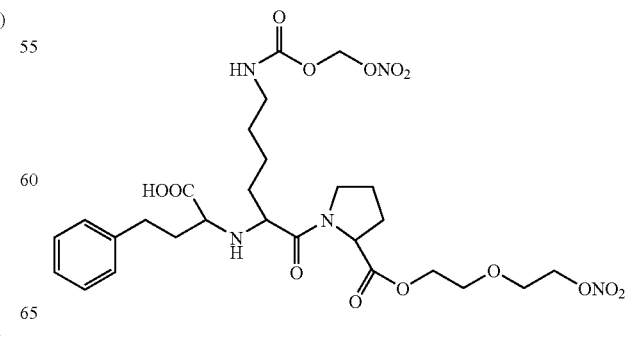

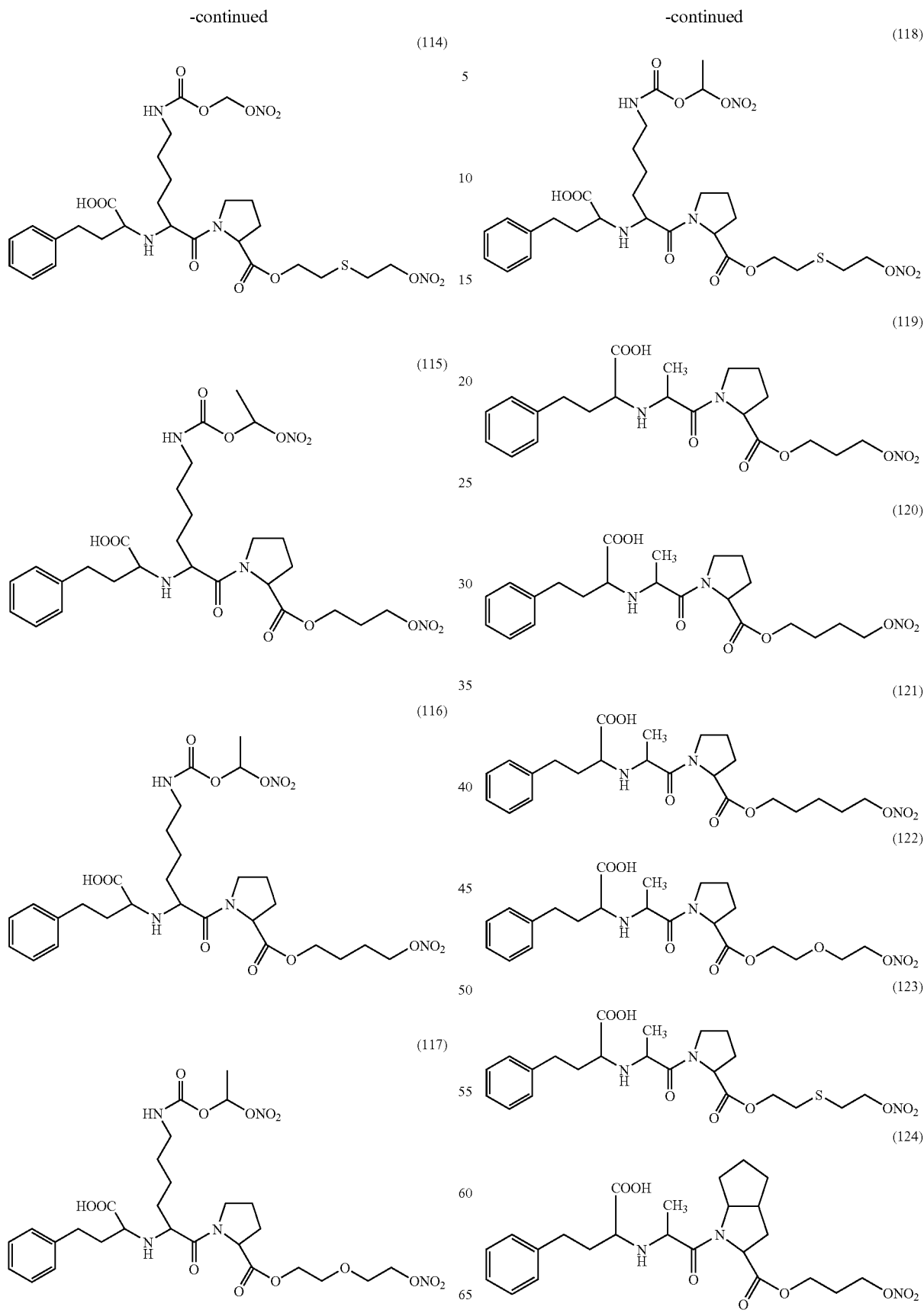

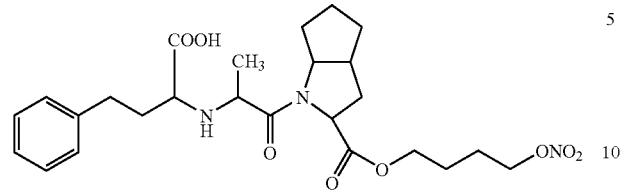
(125)
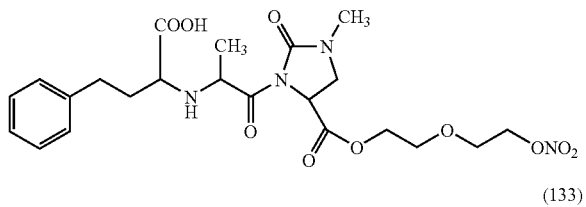
(132)
(126)
(133)
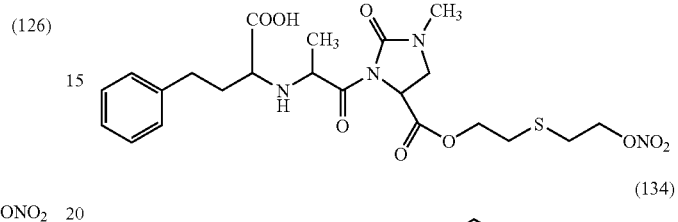
(127)
(134)
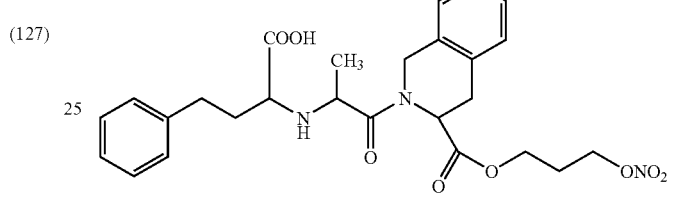
(128)
(135)
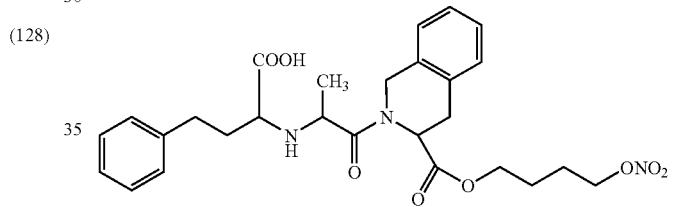
(129)
(136)
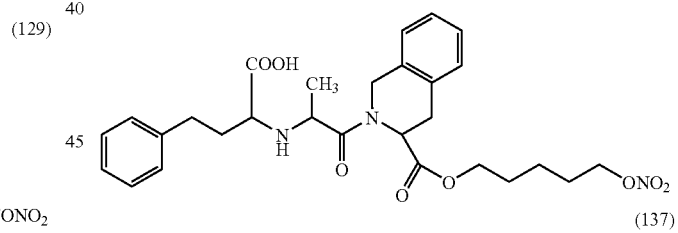
(130)
(137)
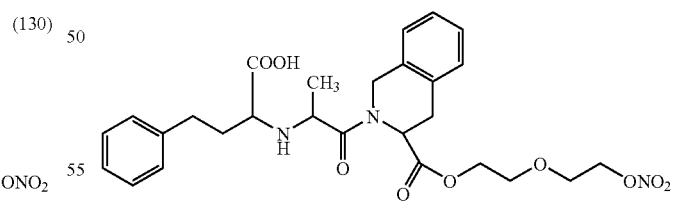
(131)
(138)
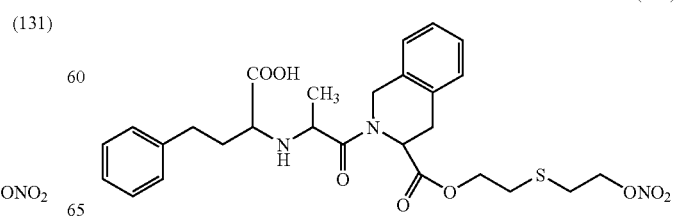

(139)
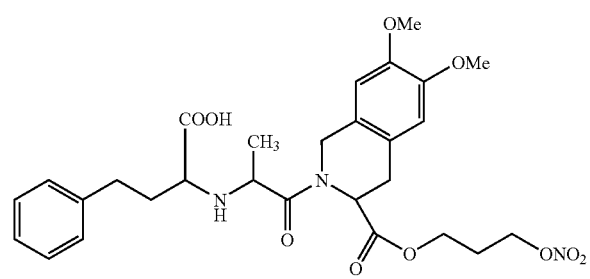
(140)
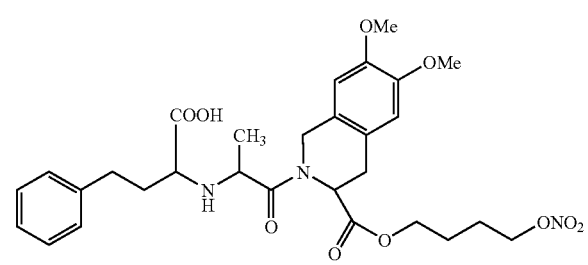
(141)
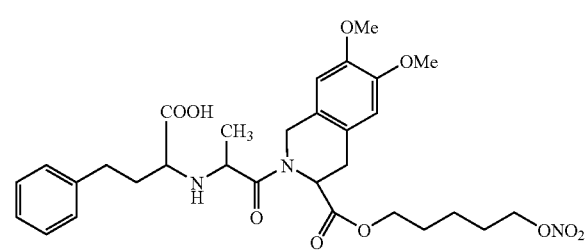
(142)
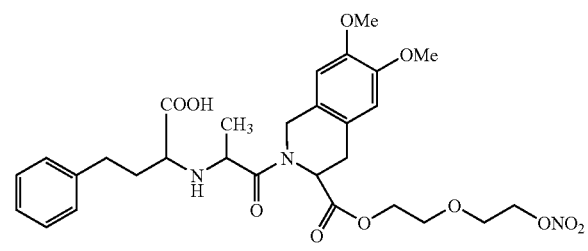
(143)
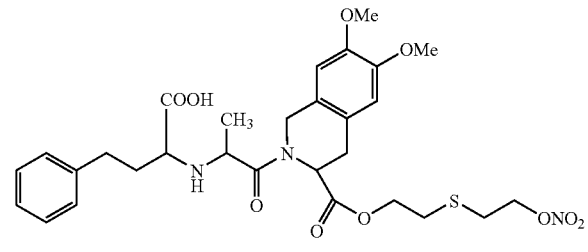
(144)
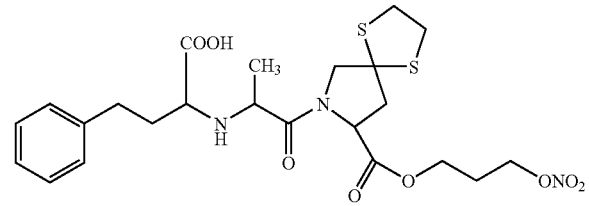
(145)
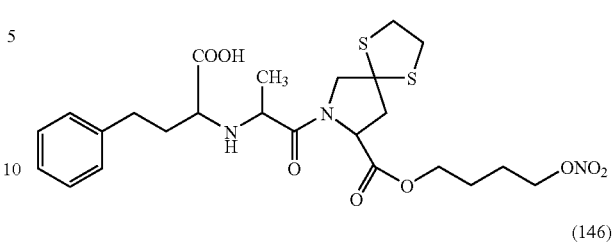
(146)
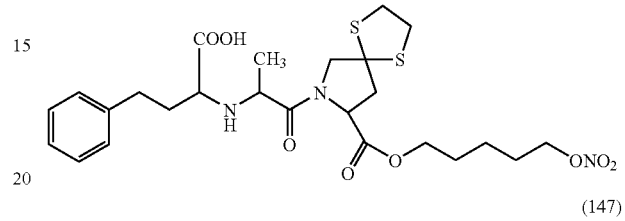
(147)
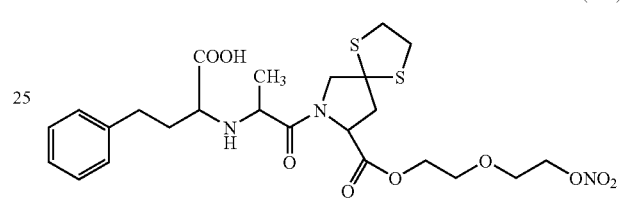
(148)
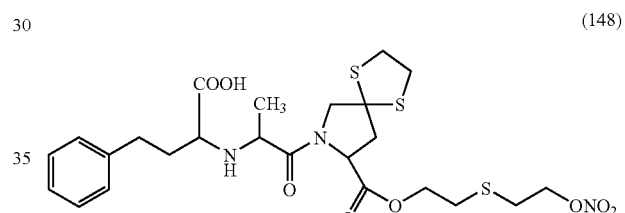
(149)
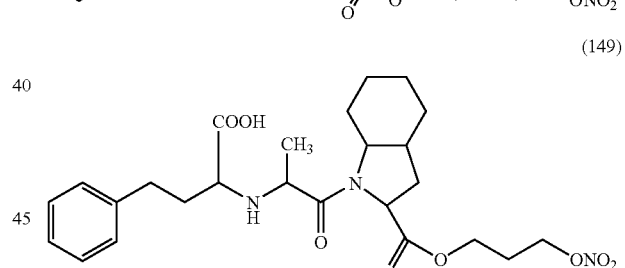
(150)
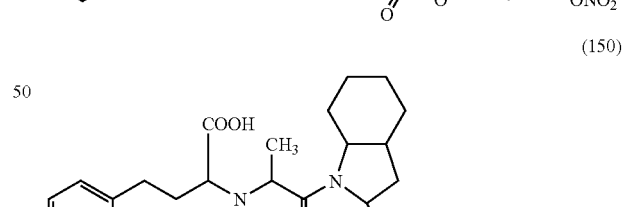
(151)
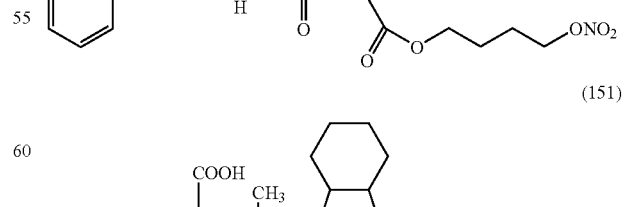

-continued

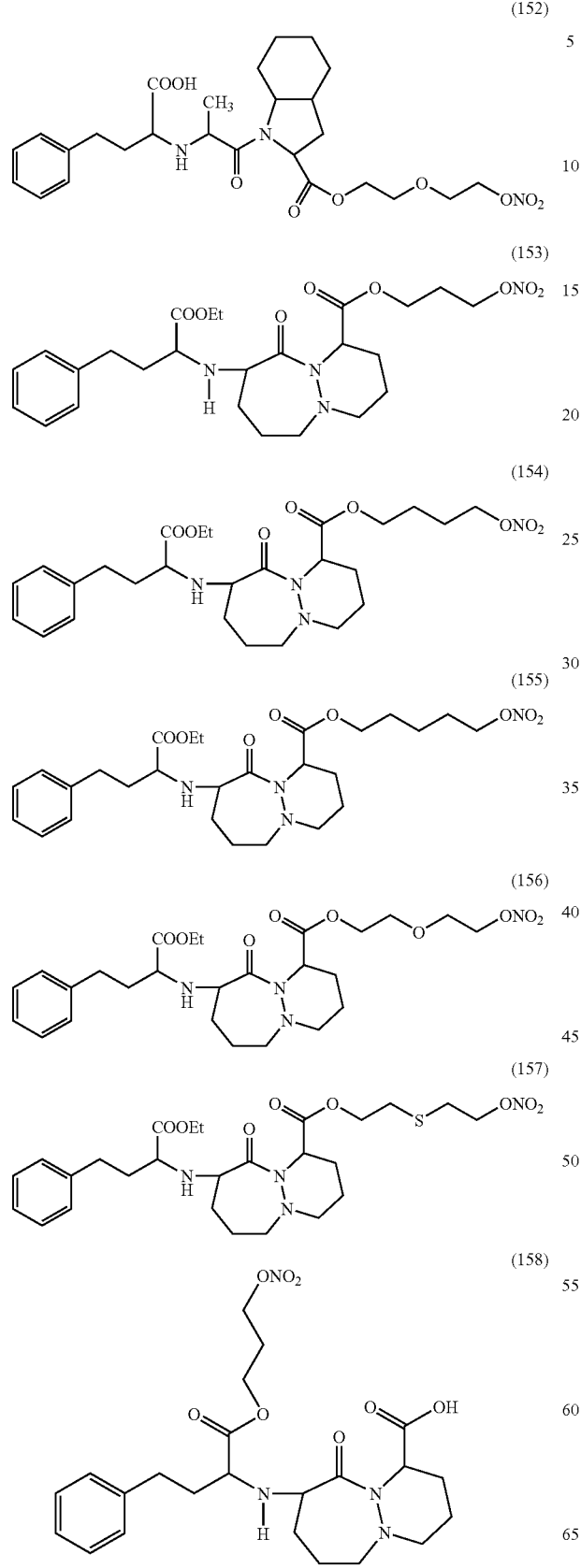

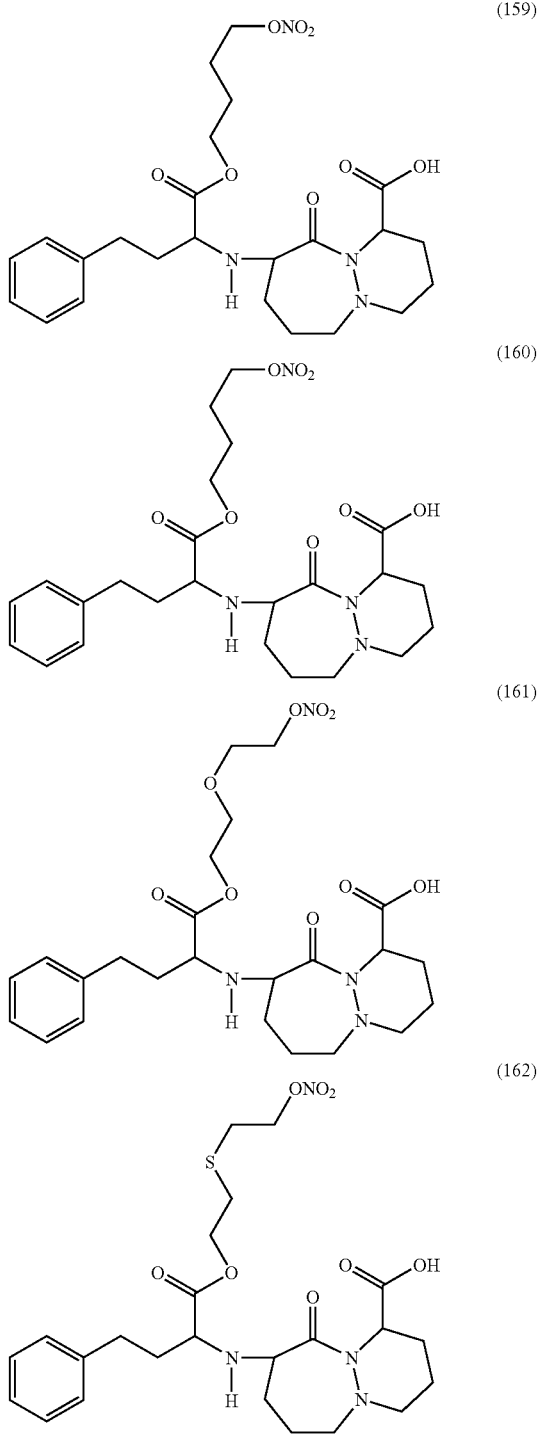

As mentioned above, object of the present invention are also pharmaceutical compositions containing at least a compound of the present invention of formula (I) together with non toxic adjuvants and/or carriers usually employed in the pharmaceutical field.

The daily dose of active ingredient that should be administered can be a single dose or it can be an effective amount divided into several smaller doses that are to be administered throughout the day. Usually, total daily dose may be in amounts preferably from 50 to 500 mg. The dosage regimen and administration frequency for treating the mentioned diseases with the compound of the invention and/or with the pharmaceutical compositions of the present invention will be selected in accordance with a variety of factors, including for example age, body weight, sex and medical condition of the patient as well as severity of the disease, route of administration, pharmacological considerations and eventual concomitant therapy with other drugs. In some instances, dosage levels below or above the aforesaid range and/or more frequent may be adequate, and this logically will be within the judgment of the physician and will depend on the disease state.

The compounds of the invention may be administered orally, parenterally, rectally or topically, by inhalation or aerosol, in formulations eventually containing conventional non-toxic pharmaceutically acceptable carriers, adjuvants and vehicles as desired. Topical administration may also involve the use of transdermal administration such as transdermal patches or iontophoresis devices. The term "parenteral" as used herein, includes subcutaneous injections, intravenous, intramuscular, intrasternal injection or infusion techniques.

Injectable preparations, for example sterile injectable aqueous or oleaginous suspensions may be formulated according to known art using suitable dispersing or wetting agents and suspending agents. The sterile injectable preparation may also be a sterile injectable solution or suspension in a non-toxic parenterally acceptable diluent or solvent. Among the acceptable vehicles and solvents are water, Ringer's solution and isotonic sodium chloride. In addition, sterile, fixed oils are conventionally employed as a solvent or suspending medium. For this purpose any bland fixed oil may be employed including synthetic mono or diglycerides, in addition fatty acids such as oleic acid find use in the preparation of injectables.

Suppositories for rectal administration of the drug can be prepared by mixing the active ingredient with a suitable non-irritating excipient, such as cocoa butter and polyethylene glycols.

Solid dosage forms for oral administration may include capsules, tablets, pills, powders, granules and gels. In such solid dosage forms, the active compound may be admixed with at least one inert diluent such as sucrose, lactose or starch. Such dosage forms may also comprise, as in normal practice, additional substances other than inert diluents, e.g. lubricating agents such as magnesium stearate. In the case of capsules, tablets and pills, the dosage forms may also comprise buffering agents. Tablets and pills can additionally be prepared with enteric coatings.

Liquid dosage forms for oral administration may include pharmaceutically acceptable emulsions, solutions, suspensions, syrups and elixirs containing inert diluents commonly used in the art, such as water. Such compositions may also comprise adjuvants, such as wetting agents, emulsifying and suspending agents, and sweetening, flavouring and the like.

Another aspect of the present invention provides the use of the compounds of formula (I) in combination with at least a compounds used to treat cardiovascular disease selected from the group consisting of: beta adrenergic blokers, calcium channel blockers, angiotensin II receptor antagonists, antithrombotics, HMGCoA reductase inhibitors, aspirin or nitrooxyderivatives of aspirin, nitrosated beta blockers, nitrosated or nitrosylated calcium channel blockers.

The present invention also provides kits comprising a compound of formula (I) and a compound used to treat cardiovascular disease as combined preparation for simultaneous, separated, sequential use for the treatment of cardiovascular disease.

Suitable beta adrenergic blockers, calcium channel blockers, angiotensin II receptor antagonists, antithrombotics, are described in the literature such as The Merck Index (13$^{th}$ edition).

Suitable nitrosated beta adrenergic blockers and nitrooxyderivatives of aspirin are disclosed respectively in WO 98/21193 and WO 97/16405.

The compounds of the present invention can be synthesized as follows.

The compound of general formula (I) as above defined wherein A is the group 1a), or a pharmaceutically acceptable salt thereof, can be obtained by a process comprising:

i) reacting a compound of formula (IIa) with a compound of formula (IIIa):

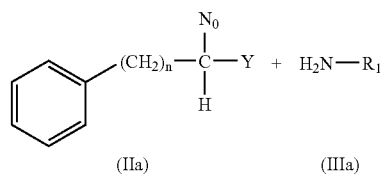

wherein n is 2 and $R_1$ are as above defined, $N_0$ is —COO—$X_1$—$ONO_2$ wherein $X_1$ is as above defined, or $N_0$ is —$COOR_0$ wherein $R_0$ a linear or branched $(C_1$–$C_{10})$-alkyl; Y is a leaving group such as a mesylate, triflate, tosylate or an halogen such as I, Br, Cl, in a suitable solvent as $CH_3CN$, THF, DMF, DMSO, in presence of an organic or inorganic base at a temperature in the range from 20° C. to 80° C. for a period in the range from 2 hours to a week, as described in Angew. Chem. Int. Ed. Engl. 22, 65, (1983); eventually acid hydrolysing the carboxylic protecting group such as tert-butyl ester, as well known in the art, for example as described in T. W. Greene "Protective groups in organic synthesis", Harvard University Press, 1980.

Compounds of formula (IIa) wherein Y is a sulphuric acid ester such as a triflate, mesylate or tosylate, can be obtained by reacting compounds of formula (IIa.1)

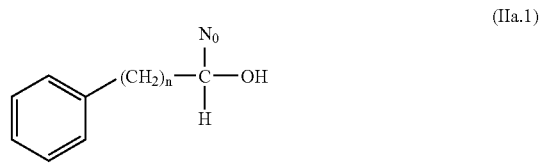

wherein $N_0$ is —$COOR_0$ being $R_0$ as above defined and n is 2, with the commercially available sulphuric acid chloride such as trifluoromethanesulfonyl, mesyl or tosyl chloride by well known methods in inert solvents such as toluene, chloroform, DMF, etc. in the presence of an organic base; Alternatively, when Y is an halogen atom, compounds (IIa) can be obtained from compounds (IIa.1), as above defined, by well known reactions, for example by reaction with thionyl chloride, halides of P$^{III}$ or P$^V$ in solvents inert such as toluene, chloroform, DMF, etc;

Compounds of formula (IIa.1) are commercially available or can be obtained by reduction of compounds of formula (IIa.2)

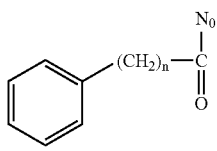
(IIa.2)

in the presence of commonly used reducing reagents such as sodium borohydride or sodium cyanobohydride at a suitable pH optionally in the presence of a chiral catalysts.

Compounds of formula (IIa.2) wherein $N_0$ is —COO—$X_1$—$ONO_2$ can be obtained by reacting compounds of formula (IIa.3)

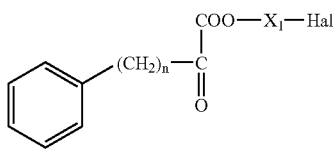
(IIa.3)

wherein $X_1$ and n are as above defined and Hal is an halogen atom such as preferably Cl, Br, I, with $AgNO_3$ in a suitable organic solvent such as acetonitrile or tetrahydrofuran (THF) under nitrogen in the dark at temperatures range between 20°–80° C.; alternatively the reaction with $AgNO_3$ can be performed under microwave irradiation in solvents such acetonitrile or THF at temperatures in the range between about 100–180° C. for time range about 1–60 min.

Compounds of formula (IIa.3) can be obtained by reacting compounds of formula (IIa.4)

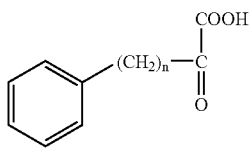
(IIa.4)

with compounds of formula (IIa.5) HO—$X_1$—Hal wherein $X_1$ is as above defined and Hal is an halogen atom such as preferably Cl, Br, I; the reaction is generally carried out in the presence of a condensing agent like dicyclohexylcarbodiimide (DCC) or other commonly used in peptide chemistry in solvent such as DMF, THF, chloroform at a temperature in the range from −5° C. to 50° C.;

Alternatively compounds of formula (IIa.2) can be obtained by reacting compounds of formula (IIa.4) with compounds of formula HO—$X_1$—$ONO_2$ (IIa.6) wherein $X_1$ is as above defined, in the presence of a condensing agent like dicyclohexylcarbodiimide (DCC) or other commonly used in peptide chemistry in solvent such as DMF, THF, chloroform at a temperature in the range from −5° C. to 50° C.;

Compounds of formula (IIIa) can be obtained from compounds of formula (IIIa.1):

$R_1$—NH—BOC     (IIIa.1)

by hydrolysis of the N—BOC protective group as known in the literature;

Compounds (IIIa.1) wherein $R_1$ is selected from (VI–VII, IX–XII) or (XIV) and $N_2$ is —$COON_4$ wherein $N_4$ is $X_1$—$ONO_2$, a linear or branched ($C_1$-$C_{10}$)-alkyl or a carboxyl protective group are obtained by reaction of the N-Boc-aminoacid of formula (IIIa.2):

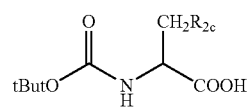
(IIIa.2)

wherein $R_2$, is H or —$CH_2$—$CH_2$—$CH_2$—NHBOC or —$CH_2$—$CH_2$—$CH_2$—$NHCOCF_3$, which is known in the literature, with a suitable amino acid ester of formula (IIIa.3):

$R_{3c}$—Z     (IIIa.3)

wherein Z is H and $R_{3c}$ is selected from:

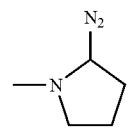
(VIb)

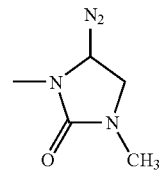
(VIIb)

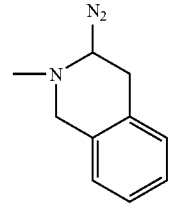
(IXb)

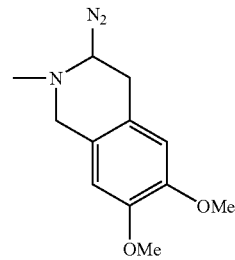
(Xb)

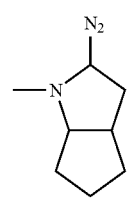
(XIb)

-continued

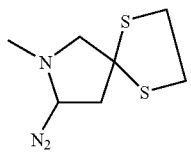
(XIIb)

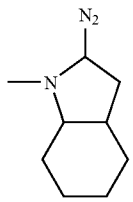
(XIVb)

wherein $N_2$ is —$COON_4$ and $N_4$ is as above defined;

the reaction is generally carried out in the presence of a condensing agent like dicyclohexylcarbodiimide (DCC) or other commonly used in pepetide chemistry condensing agents in solvent such as DMF, THF, chloroform at a temperature in the range from −5° C. to 50° C.;

Compounds of formula (IIIa.3) are obtainable by deprotection of the amine group of the corresponding compounds (IIIa.3) wherein Z is the BOC protective group or another commonly used N-protective group;

Compounds (IIIa.3) wherein $N_2$ is equal to —$COON_4$ and $N_4$ is a t-but and Z is suitable N-protective group can be obtained by esterification of the corresponding compound (IIIa.3) wherein Z is the N-protective group and $N_2$ is —COOH by known methods in the literature for the preparation of esters;

Compounds (IIIa.3), wherein $N_4$ is —$X_1$—$ONO_2$ wherein $X_1$ is as above defined, can be obtained:

by reacting a compound of formula (IIIa.3), as above defined, wherein Z is the BOC protective group and $N_2$ is COOH with a compound of formula HO—$X_1$—$ONO_2$ (IIa.6) in presence of a condensing agent like DCC as above described;

alternatively compounds (IIIa.3) can be obtained by reacting the corresponding compound wherein Z is the BOC protective group and $N_2$ is —COOH with a compound of formula HO—$X_1$—Hal (IIa.5) wherein $X_1$ and Hal are as above defined, in presence of a condensing agent like DCC as above described; the obtained compound is then reacted with $AgNO_3$ in a suitable organic solvent such as acetonitrile or tetrahydrofuran (THF) under nitrogen in the dark at temperatures range between 20°–80° C.; alternatively the reaction with $AgNO_3$ can be performed under microwave irradiation in solvents such acetonitrile or THF at temperatures in the range between about 100–180° C. for time range about 1–60 min.

Compounds (IIa.5) are commercially available or can be obtained by method well known in the literature.

Compounds of formula HO—$X_1$—$ONO_2$ (IIa.6) can be obtained by reacting compounds (IIa.5) with AgNO3 as previously described.

Alternatively to the previous synthesis, the compound of general formula (I) as above defined wherein A is the group 1a) can be obtained by reacting a compound of formula (IVa) with a compound of formula (Va):

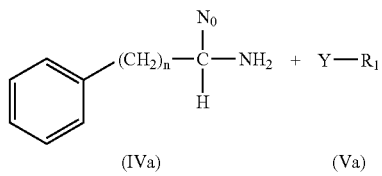

(IVa)          (Va)

wherein n is 2, $R_1$ and Y are as above defined, $N_0$ is —COO—$X_1$—$ONO_2$ or —$COOR_0$ wherein $R_0$ is as above defined; optionally acid hydrolysing the carboxylic protecting group such as tert-butyl ester, as well known in the art, for example as described in T. W. Greene "Protective groups in organic synthesis", Harvard University Press, 1980.

Compounds of formula (IVa) can be obtained from compounds of formula (IVa.1):

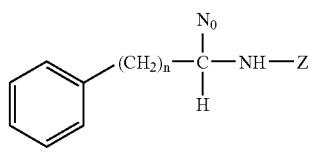
(IVa.1)

wherein Z is a suitable N-protective group by deprotection of the amine group as above described;

Compounds (IVa.1) wherein $N_0$ is —$COOR_0$, $R_0$ being a linear or branched ($C_1$–$C_{10}$)-alkyl and n is as above defined, can be obtained by esterification of the corresponding compounds of formula (IVa.2) wherein Z is a suitable N-protective group:

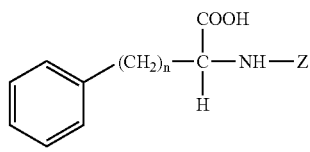
(IVa.2)

in presence of a condensing agent like DCC as above described;

Compounds (IVa.1), wherein $N_0$ is —COO—$X_1$—$ONO_2$ wherein $X_1$ is as above defined, can be obtained by reacting a compound of formula (IVa.3) with $AgNO_3$ as above described:

(IVa.3) → (IVa.1)

Compounds (IVa.3) can be obtained by converting a compound of formula (IVa.2) wherein Z is Boc, into the ester by reaction with a compound of formula HO—X$_1$—Hal (IIa.5). The reaction is generally carried out in the presence of condensing agent such as DCC as above described;

Alternatively compounds (IVa.1) can be obtained by reacting a compound of formula (IVa.2) with a compound of formula HO—X$_1$—ONO$_2$ (IIa.6) in presence of a condensing agent like DCC as above described;

Compounds (Va) wherein Y is above defined, R$_1$ is (VI–XII) or (XIV) and N$_2$ is —COO—X$_1$—ONO$_2$ wherein X$_1$ is as above defined, or N$_2$ is —COOR$_0$ wherein R$_0$ is a linear or branched (C$_1$–C$_{10}$)-alkyl is as above defined, can be obtained by reacting a compound of formula (Va.1) or (Va.2) wherein R$_2$c is CH$_3$ or —CH$_2$—CH$_2$—CH$_2$—NHBOC with a suitable aminoacid ester R$_{3c}$—Z (IIIa.3) wherein Z is H and R$_{3c}$ is as above defined:

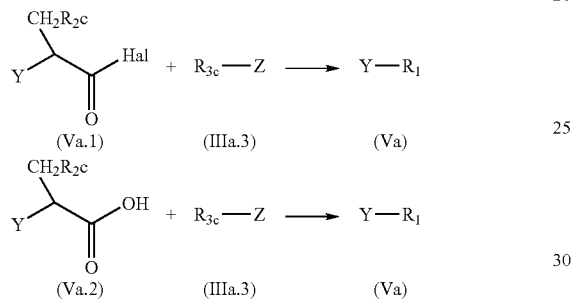

Compounds (Va.1) can be obtained from a compound of formula (Va.3) by well known methods (Chem. Pharm. Bull. 39(6), 1374–1377), of esterification hydrolysis and halogenation. The reaction scheme is the following:

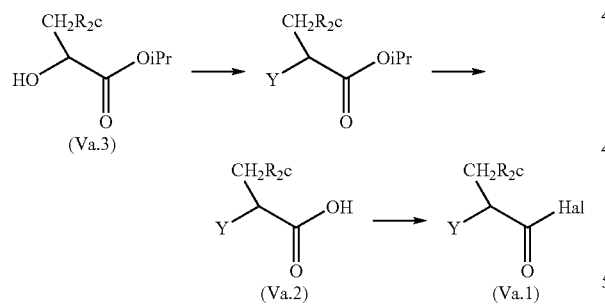

Compounds of formula (I) wherein s is 1, A is 1a) wherein R$_1$ is selected from (VI, VII, IX–XII) or (XIV) can be obtained as the following scheme:

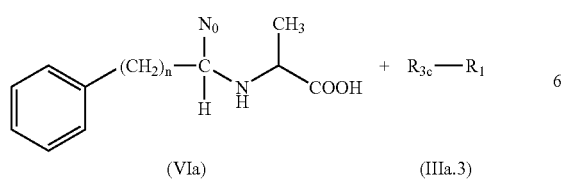

by reacting a compound of formula (VIa) wherein N$_0$ is —COOR$_0$ wherein R$_0$ is a linear or branched (C$_1$–C$_{10}$)-alkyl or a carboxyl protective group and n is 2, with a suitable aminoacid ester R$_{3c}$—Z (IIIa.3) wherein Z is H and R$_{3c}$ is selected from:

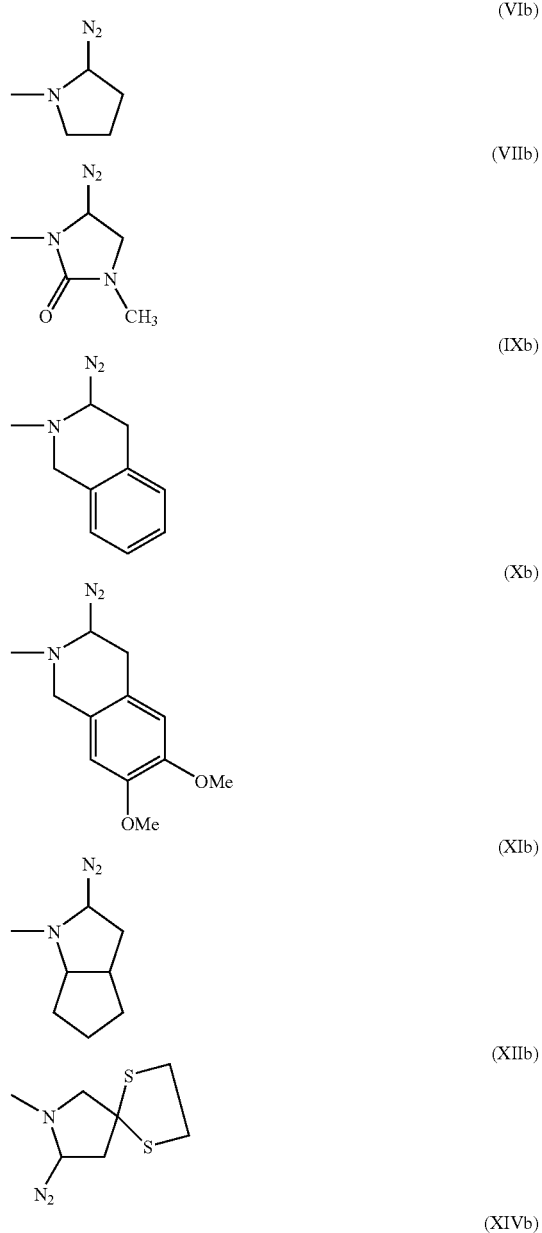

wherein N$_2$ is —COO—X$_1$—ONO$_2$ wherein X$_1$ is selected from:
a linear or when possible branched (C$_1$–C$_6$)-alkylene optionally substituted with at least an halogen atom,
a bivalent radical equal to —(CH$_2$—CH$_2$—O)$_2$— or —(CH$_2$—CH$_2$—S)$_2$—,
a compound of formula (IB)

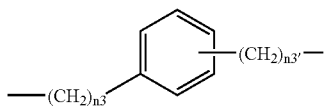

(IB)

wherein n3 is an integer from 0 to 20, preferably from 0 to 5, n3' is an integer from 1 to 20, preferably from 1 to 5, provided that the —ONO$_2$ group is bound to a —CH$_2$ group;

in the presence of a condensing agent like carbonyldiimadazole, DCC, EDAC, HATU or other commonly used in pepetide chemistry condensing agents in solvents such as DMF, THF, chloroform methylene chloride at a temperature in the range from −5° C. to 50° C. as above described; optionally acid hydrolysing the carboxylic protective group of the obtained compound;

Compounds of formula (VIa) are commercially available or can be obtained by known methods in the literature.

Compounds of formula (I) wherein s is 2, $X_1$ is a linear or when possible branched ($C_1$–$C_6$)-alkylene optionally substituted with at least an halogen atom, or $X_1$ is a bivalent radical equal to —(CH$_2$—CH$_2$—O)$_2$— or —(CH$_2$—CH$_2$—S)$_2$—, A is 1a) wherein $N_0$ is COOR$_0$ wherein $R_0$ is H or linear or branched alkyl, $R_1$ is the compound of formula (VIII) wherein $N_{2a}$ and $N_2$ are —COO—$X_1$—ONO$_2$ wherein $X_1$ is as above defined, can be obtained by reacting compounds of formula (VIIa)

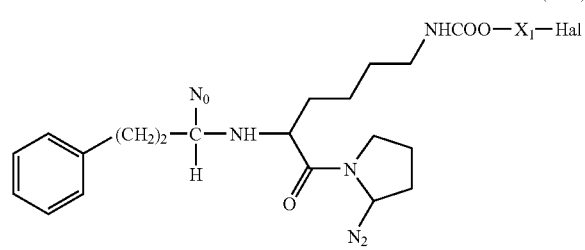

(VIIa)

wherein $N_0$ is —COOR$_0$ wherein $R_0$ is a linear or branched ($C_1$–$C_{10}$)-alkyl, $N_2$ is —COO—$X_1$—ONO$_2$ with AgNO$_3$ as previously described; optionally hydrolysing the carboxylic protective group.

Compound (VIIa) can be obtained from compound (VIIa.1)

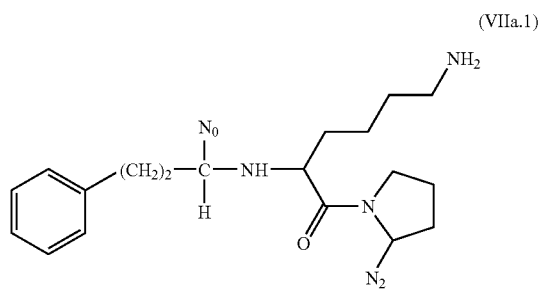

(VIIa.1)

wherein $N_0$ and $N_2$ are as above defined, by reaction with a compound of formula Act-COO—$X_1$—Hal (VIIa.2)

wherein $X_1$ and Hal are as previously defined and Act is an Halogen atom or a commonly used in peptide chemistry activating carboxylic group selected from the following compounds of formula (VIIa.3) or of formula (VIIa.4)

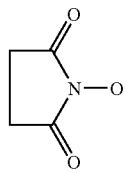

(VIIa.3)

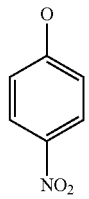

(VIIa.4)

the reaction is carried out in the presence of an organic or inorganic base in solvents such as CH$_2$Cl$_2$, DMF, THF, acetonitrile, water, dioxane/water THF/water.

Compounds (VIIa.1) are obtainable with the general methods above described.

Alternatively compounds of formula (I) wherein s is 2, A is 1a) wherein $N_0$ is —COOR$_0$ wherein $R_0$ is H or linear or branched ($C_1$–$C_{10}$)-alkyl, $R_1$ is the compound of formula (VIII) wherein $N_{2a}$ and $N_2$ are —COO—$X_1$—ONO$_2$ wherein $X_1$ is as above defined, can be obtained by reacting a compound of formula (VIIa.1) wherein $N_0$ is —COOR$_0$ wherein $R_0$ is a linear or branched ($C_1$–$C_{10}$)-alkyl, $N_2$ is —COO—$X_1$—ONO$_2$ wherein $X_1$ as above defined, with a compound of formula Act-COOX$_1$—ONO$_2$ (VIIa.5) in a suitable solvent as previously described; optionally hydrolysing the carboxylic protective group.

Compounds of formula (I) wherein s is 2, A is 1a) wherein $N_0$ is —COOR$_0$ wherein $R_0$ is H or a linear or branched ($C_1$–$C_{10}$)-alkyl, $R_1$ is the compound of formula (VIII) wherein $N_{2a}$ is —CO—$X_1$—ONO$_2$ and $N_2$ is —COO—$X_1$—ONO$_2$, can be obtained by reacting a compound of formula (VIIIa)

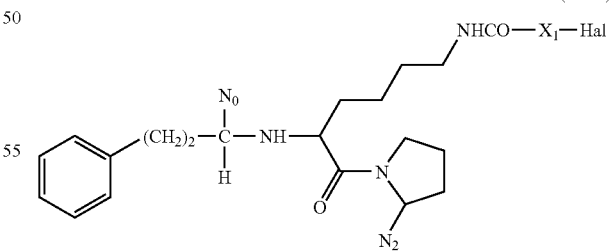

(VIIIa)

wherein $N_0$ is —COOR$_0$ wherein $R_0$ is a linear or branched ($C_1$–$C_{10}$)-alkyl, $N_2$ is —COO—$X_1$—ONO$_2$ wherein $X_1$ as above defined, with AgNO$_3$ as previously described; optionally hydrolysing the carboxylic protective group.

Compound (VIIIa) can be obtained from compound (VIIa.1) where $N_0$ and $N_2$ are as previously defined and $N_{2a}$ is H by reaction with compounds of formula Act-CO—$X_1$—Hal (VIIIa.2) wherein Act, $X_1$ and Hal are as above defined, in the presence of an organic or inorganic base in solvents such as $CH_2Cl_2$, DMF, THF, acetonitrile, water, dioxane/water THF/water.

Compounds (VIIa.1) can be obtained by the general methods above described.

Alternatively compounds of formula (I) wherein s is 2, A is 1a) wherein $N_0$ is $COOR_0$ wherein $R_0$ is H or a linear or branched ($C_1$–$C_{10}$)-alkyl, $R_1$ is the compound of formula (VIII) wherein $N_{2a}$ is —CO—$X_1$—$ONO_2$ and $N_2$ is —COO—$X_1$—$ONO_2$, can be obtained by reacting a compound of formula (VIIa.1) wherein $N_0$ is —$COOR_0$ wherein $R_0$ is a linear or branched ($C_1$–$C_{10}$)-alkyl, $N_2$ is —COO—$X_1$—$ONO_2$ wherein $X_1$ is as above defined, with a compound of formula Act-CO—$X_1$—$ONO_2$ (VIIIa.3) wherein $X_1$ and Act are as above defined, with a condensing agent as above described; optionally hydrolysing the carboxylic protective group.

Compounds of formula (I) wherein s is 2, A is 1a), $R_1$ is the compound of formula (VIII) wherein $N_{2a}$ is H, $N_0$ and $N_2$ are —COO—$X_1$—$ONO_2$ wherein $X_1$ is as above defined, can be obtained by reacting a compound of formula (VIIc)

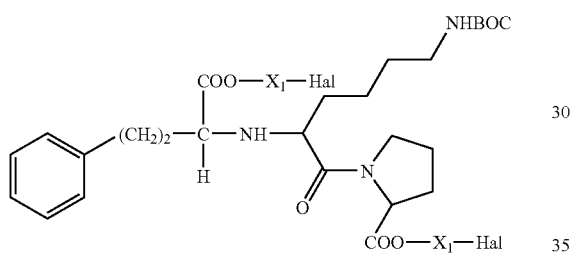

(VIIc)

with $AgNO_3$ as previously described; eventually hydrolysing the amine protective group.

Compounds of formula (VIIc) can be obtained by reacting compound of formula (VIIc.1)

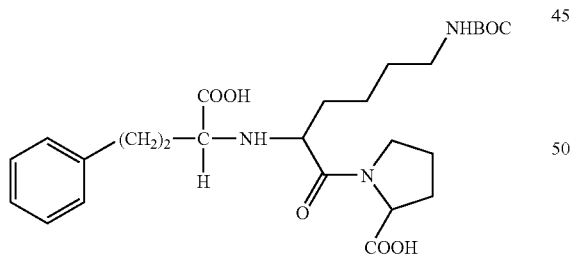

(VIIc.1)

with a compound of formula HO—$X_1$—Hal (IIa.5) where $X_1$ and Hal are as above defined with DCC or other condensing agents as previously described.

Compounds (VIIc.1) can be obtained from commercial available Lisinopril.

Alternatively compounds of formula (I) wherein s is 2, A is 1a) wherein n is 2, $R_1$ is the compound of formula (VIII) $N_{2a}$ is H, $N_0$ and $N_2$ are —COO—$X_1$—$ONO_2$ wherein $X_1$ as above defined, can be obtained by reacting a compound of formula (VIIc.1) with a compound of formula HO—$X_1$—$ONO_2$ (IIa.6) wherein $X_1$ is as above defined with DCC or other condensing agents as previously described and hydrolysing the amino protective group.

Alternatively compounds (I) wherein s is 1, A is 1a) wherein n is 2, $N_0$ is equal to —$COOR_0$ wherein $R_0$ is H or linear or branched ($C_1$–$C_{10}$)-alkyl, $R_1$ is selected from (VI–VII, IX–XII) or (XIV) wherein $N_2$ is —COO—$X_1$—$ONO_2$, can be obtained by reacting a compound of formula (IXa)

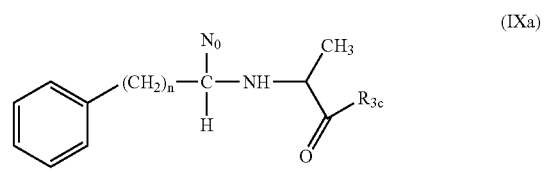

(IXa)

wherein $R_{3c}$ is selected from (VIb–VIIb, IXb–XIIb) or (XIVb) wherein $N_2$ is —COO—$X_1$—Hal wherein $X_1$ and Hal are as above described, with $AgNO_3$ in a suitable solvent as above described; optionally hydrolysing the carboxylic protective group.

Compounds (IXa) can be obtained by reacting a compound of formula (IXa.1)

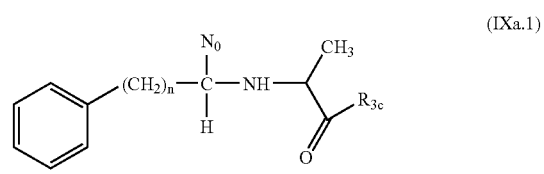

(IXa.1)

wherein $N_0$ is as above defined and in $R_{3c}$ $N_2$ is —COOH, with a compound of formula HO—$X_1$—Hal (IIa.5) in the presence of DCC or other condensing agents as above described;

Alternatively compounds (I) where A is 1a) s is 1, $N_0$ is equal to —$COOR_0$ wherein $R_0$ is H or linear or branched ($C_1$–$C_{10}$)-alkyl, $R_1$ is selected from (VI–VII, IX–XII) or (XIV) wherein $N_2$ is —COO—$X_1$—$ONO_2$, can be obtained by reacting a compound of formula (IXa.1) with a compound of formula HO—$X_1$—$ONO_2$ (IIa.6) with DCC or other condensing agents as already described; eventually hydrolysing the carboxylic protective group.

Compounds (I) wherein s is 2, $X_1$ is as above described, A is 1a) wherein $N_0$ is —COO—$X_1$—$ONO_2$, $R_1$ is selected from (VI–VII, IX–XII) or (XIV) wherein $N_2$ is —COO—$X_1$—$ONO_2$ can be obtained by reacting a compound of formula (Xa)

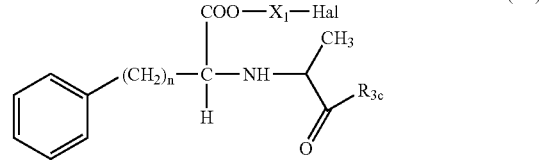

(Xa)

wherein $X_1$ and Hal are as above described, $R_{3c}$ is selected from (VIb–VIIb, IXb–XIIb) or (XIVb) wherein $N_2$ is —COO—$X_1$—Hal, with $AgNO_3$ in a suitable solvent according to the methods above described.

Compounds (Xa) are obtainable by reacting a compound of formula (Xa.1)

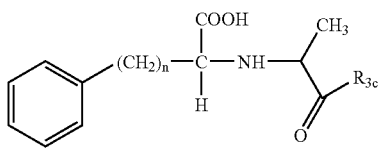

wherein in $R_{3c}$ $N_2$ is —COOH, with a compound of formula HO—$X_1$—Hal (IIa.5) wherein $X_1$ and Hal are as above described, in the presence of DCC or EDAC or other commonly used in peptide chemistry condensing agents.

Alternatively compounds of formula (I) wherein s is 2, $X_1$ is as above described, A is 1a) wherein $N_0$ is —COO—$X_1$—$ONO_2$, $R_1$ is selected from (VI–VII, IX–XII) or (XIV) wherein $N_2$ is —COO—$X_1$—$ONO_2$ can be obtained by reacting a compound of formula (XIa.1) in a suitable solvent with a compound of formula HO—$X_1$—$ONO_2$ (IIa.6) in the presence of a condensing agent using method as above described.

Compound of formula (I) wherein s is 1, $X_1$ is a linear or when possible branched $(C_1-C_6)$-alkylene optionally substituted with at least an halogen atom or $X_1$ is —($CH_2$—$CH_2$—O)$_2$— or —($CH_2$—$CH_2$—S)$_2$—, A is 1a) wherein $N_0$ is —$COOR_0$ wherein $R_0$ is a linear or branched $(C_1-C_{10})$-alkyl or a carboxyl protective group, $R_1$ is the radical of formula (VIII) wherein $N_{2a}$ is H, can be prepared by hydrolyzing a compound obtained by reacting a compound of formula (XIa)

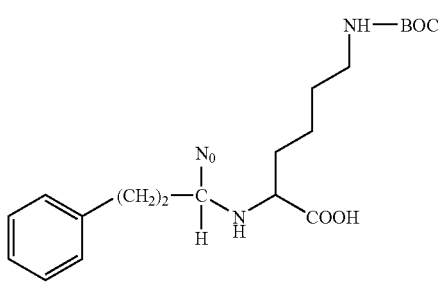

wherein $N_0$ is —$COOR_0$ wherein $R_0$ is a linear or branched $(C_1-C_{10})$-alkyl or a carboxyl protective group, with a compound of formula (XIa.1)

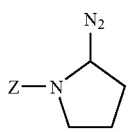

wherein $N_2$ is —COO—$X_1$—$ONO_2$ and Z is H.

Compounds of formula (XIa) are commercially available or can be obtained from the commercially available compounds following known procedures or can be prepared by reacting a compound of formula (XIa.2)

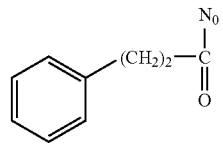

wherein n is 2, $N_0$ are as above defined with compounds of formula (XIa.3)

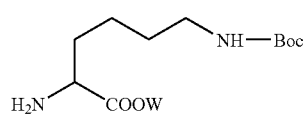

wherein W is H or a carboxylic acid protective group, in the presence of hydrogen or commonly used reducing reagents such as sodium borohydride or sodium cyanoborohydride at a suitable pH, optionally in the presence of chiral catalysts; eventually hydrolysing the W protective groups.

Compounds (XIa.3) wherein W is a carboxilic protective group can be obtained from the corresponding commercially available amino acid by methods known in the literature.

Compounds (XIa.1) can be obtained by reacting a compound of formula (XIa.1) wherein Z is the BOC protective group and $N_2$ is COOH with a compound of formula HO—$X_1$—$ONO_2$ (IIa.6) or a compound of formula HO—$X_1$—Hal (IIa.5) as above described. In the last case the obtained product is reacted with $AgNO_3$.

Compounds of general formula (I) wherein s is 1, $X_1$ is —($CH_2$—$CH_2$—O)$_2$— or —($CH_2$—$CH_2$—S)$_2$—, A is the group 1a) wherein n is 1, $N_0$ is —COO— and $R_1$ is (III) can be obtained:

by reacting alacepril with a compound of formula HO—$X_1$—$ONO_2$ (IIa.6) wherein $X_1$ is as above defined, in the presence of a condensing agent like DCC as above described;

or by reacting a compound of formula (XIIa)

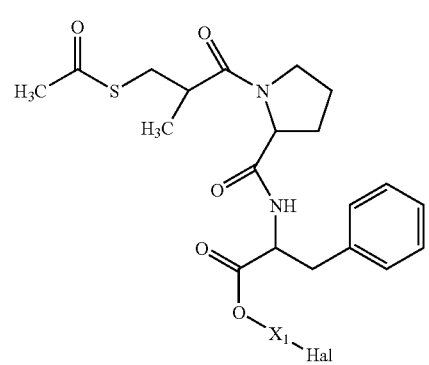

with $AgNO_3$ as above described.

compounds (XIIa) can be obtained by reacting alacepril with a compound of formula HO—$X_1$—Hal (IIa.5) wherein $X_1$ is as above defined, according to the above described methods:

Compounds of general formula (I) wherein s is 1, $X_1$ is —($CH_2$—$CH_2$—O)$_2$— or —($CH_2$—$CH_2$—S)$_2$—, A is the group 1c) wherein $R_{1c}$ is H or —$COCH_3$, can be obtained:

by reacting S-acetylcaptopril with a compound of formula HO—$X_1$—$ONO_2$ (IIa.6) wherein $X_1$ is as above defined, in the presence of a condensing agent like DCC as above described;

or by reacting compound of formula (XIIIa)

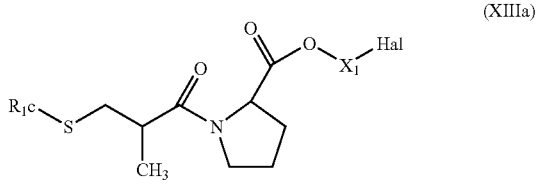

(XIIIa)

wherein $R_{1c}$, $X_1$ and Hal are as above defined, with $AgNO_3$ as above described.

compounds (XIIIa) can be obtained by reacting S-acetyl-captopril with a compound of formula HO—$X_1$—Hal (IIa.5) in the presence of a condensing agent like DCC as above described.

A compound of general formula (I) wherein s is 1, $X_1$ is a linear or when possible branched ($C_1$–$C_6$)-alkylene optionally substituted with at least an halogen atom, or $X_1$ is a bivalent radical equal to —($CH_2$—$CH_2$—O)$_2$— or —($CH_2$—$CH_2$—S)$_2$—, A is the group 1c) wherein $R_{1c}$ is the group (XIX), can be obtained:

by reacting commercially available Moveltipril with a compound of formula HO—$X_1$—$ONO_2$ (IIa.6) wherein $X_1$ is as above defined, in the presence of a condensing agent like DCC as above described;

or by reacting compound of formula (XIIIa) wherein $R_{1c}$, $X_1$ and Hal are as above defined, with $AgNO_3$ as above described.

compounds (XIIIa) can be obtained by reacting moveltipril with a compound of formula HO—$X_1$—Hal (IIa.5) in the presence of a condensing agent like DCC as above described.

The obtained compounds of general formula (I) can be converted into a pharmaceutically acceptable salt thereof.

EXAMPLES

The following examples are to further illustrate the invention without limiting it.

Example 1

Synthesis of N-[(1S)-1-(3-nitrooxypropoxycarbonyl)-3-phenylpropyl]-L-alanyl-L-proline hydrochloride (corresponding to compound 51)

N-Boc-Homophenylalanine (5.00 g, 17.9 mmol) and 3-bromo-1-propanol (1.60 mL, 17.7 mmol) were dissolved in $CH_2Cl_2$ (25 mL) and the mixture was cooled to 0° C. A solution of N,N-dicyclohexylcarbodiimide (4.80 g, 23.3 mmol) and N,N-dimethylaminopyridine (0.23 g, 1.90 mmol) in $CH_2Cl_2$ (25 mL) was slowly added and the reaction was slowly warmed to room temperature and stirred for 12 hours. The dicyclohexylurea was filtered off and the mother liquor was concentrated and purified by flash chromatography (Hexane/EtOAc 8:2) affording N-Boc-Homophenylalanine 3-bromopropyl ester as a clear oil (5.64 g, 79%).

N-Boc-Homophenylalanine 3-bromopropyl ester (5.37 g, 13.4 mmol) was suspended in $CH_3CN$ (28 mL), $AgNO_3$ (5.72 g, 33.7 mmol) was added and the reaction was warmed at 40° C. for 7 hours. The formed salts were filtered off and the organic phase was diluted with $CH_2Cl_2$ (150 mL) and washed with $H_2O$ (2×50 mL), brine (50 mL), dried over $Na_2SO_4$ and concentrated, affording N-Boc-Homophenylalanine 3-nitrooxypropyl ester as a clear oil (4.79 g, 92%).

N-Boc-Homophenylalanine 3-nitrooxypropyl ester was dissolved in $Et_2O$ (50 mL) and HCl gas was bubbled into the solution for 5 hours. Then the mixture was concentrated, affording Homophenylalanine 3-nitrooxypropyl ester hydrochloride as a white-off powder (3.85 g, 96%).

(2R)-2-(4-Toluenesulfonyloxy)propionic acid (Chem. Pharm. Bull. 39(6) 1374, 1991) (7.00 g, 28.7 mmol) was dissolved in $CHCl_3$ (50 mL) and $SOCl_2$ (10.2 mL, 141 mmol) was added. The reaction was refluxed for 3 hours, then concentrated. The residue was dissolved in $CHCl_3$ (100 mL) and added to a 0° C. solution of L-Proline t-butyl ester (4.98 g, 29.1 mmol) in $CHCl_3$ (50 mL). The reaction was slowly warmed to room temperature and stirred overnight.

The organic phase was washed with HCl (4%, 3×50 mL), $NaHCO_3$ (5%, 3×50 mL), brine (3×50 mL), dried over $Na_2SO_4$ and concentrated, affording N-[(2R)-2-(4-toluenesulfonyloxy)propionyl]-L-proline t-butyl ester as a white powder (10.4 g, 91%)

Homophenylalanine 3-nitrooxypropyl ester hydrochloride (3.85 g, 12.1 mmol) and N-[(2R)-2-(4-toluenesulfonyloxy) propionyl]-L-proline t-butyl ester (6.40 g, 16.1 mmol) were dissolved in DMF (15 mL) and triethylamine (3.9 mL, 28 mmol) was added to the solution. The reaction was stirred at room temperature for 48 hours, then N-[(2R)-2-(4-toluenesulfonyloxy)propionyl]-L-proline t-butyl ester (3.21 g, 8.1 mmol) was added again and the reaction stirred for further 48 hours. The reaction mixture was diluted with $Et_2O$ (100 mL), washed with brine (3×50 mL) dried over $Na_2SO_4$ and concentrated. The crude material was purified by flash chromatography ($CHCl_3$/EtOAc 2:1) affording N-[(1S)-1-(3-nitrooxypropoxycarbonyl)-3-phenylpropyl]-L-alanyl-L-proline t-butyl ester as a clear oil (2.84 g, 46%). The product was dissolved in $CH_3CN$ (20 mL), maleic acid was added (0.69 g, 5.9 mmol) and the solvent was removed. The crude material was crystallised from EtOAc/$iPr_2O$ affording N-[(1S)-1-(3-nitrooxypropoxycarbonyl)-3-phenylpropyl]-L-alanyl-L-proline t-butyl ester hydrogen maleate as a white powder (2.27 g, 30%, 98%).

N-[(1S)-1-(3-nitrooxypropoxycarbonyl)-3-phenylpropyl]-L-alanyl-L-proline t-butyl ester hydrogen maleate was dissolved in $Et_2O$ (100 mL) and the organic phase was extracted with $NaHCO_3$ (5%, 5×50 mL), dried over $Na_2SO_4$ and concentrated. The residue was dissolved in $Et_2O$ (30 mL) and HCl gas was bubbled into the solution for 5 hours. The reaction was concentrated and the residue was treated with hexane affording the title compound as a white powder (1.52 g, 76%).

$^1$H-NMR ($D_2O$) (2 rotamers): 7.32–7.19 (m, 5H), 4.49 (m, 2H) 4.41–4.11 (m, 4H), 3.99+3.84 (q+t, 2H), 3.57+3.49+3.37 (3m, 2H), 2.70 (m, 2H), 2.21 (m, 3H), 2.02 (m, 2H) 1.92 (m, 2H), 1.50 (d, 3H), 1.44 (d, 3H)

Example 2

Synthesis of N-[(1S)-1-(5-nitrooxyethoxyethoxycarbonyl)-3-phenylpropyl]-L-alanyl-L-proline maleate (corresponding to compound 54)

Starting from N-Boc-homophenylalanine (5.87 g, 21 mmol) and diethylenglycol monochloride (2.23 mL, 21 mmol) following the procedure above described, N-Boc-homophenylalanine 5-Chloroethoxyethyl ester (6.0 g 74%) was obtained.

A mixture of N-Boc-Homophenylalanine 5-Chloroethoxyethyl ester (5.58 g, 14.21 mmol), NaI (21.3 g, 142.1 mmol) in $CH_3CN$ was refluxed for 11 hrs then concentrated and partitioned between $CH_2Cl_2$ and water and separated. The organic layer was dried over $Na_2SO_4$ and evaporated yielding N-Boc-homophenylalanine 5-iodoethoxyethyl ester as a colourless oil (6.72 g, 99%).

A mixture of N-Boc-homophenylalanine 5-iodoethoxyethyl ester (6.6 g, 13.84 mmol), $AgNO_3$ (5.88 g, 34.6 mmol) in $CH_3CN$ (70 ml) was heated to 60° C. for 7 hrs in the dark. The formed salts were filtered off and the organic phase was diluted with $CH_2Cl_2$ (150 mL) and washed with $H_2O$ (2×50 mL), brine (50 mL), dried over $Na_2SO_4$ and concentrated, affording N-Boc-Homophenylalanine 5-nitrooxyethoxyethyl ester as a pale yellow oil (5.39 g, 95%).

N-Boc-Homophenylalanine 5-nitrooxyethoxyethyl ester (4.5 g, 10.9 mmol) was dissolved in $Et_2O$ (30 mL) and HCl gas was bubbled into the solution for 5 hours. Then the mixture was concentrated, affording homophenylalanine 5-nitrooxyethoxyethyl ester hydrochloride as a white-off powder (3.55 g, 93%).

Starting from homophenylalanine 5-nitrooxyethoxyethyl ester hydrochloride (3.2 g, 9.17 mmol) and N-[(2R)-2-(4-toluenesulfonyloxy)propionyl]-L-proline t-butyl ester (obtained in Example 1) (6.8 g 17.2 mmol) following the procedure described in Example 1, N-[(1S)-1-(5-nitrooxyethoxyethoxycarbonyl)-3-phenylpropyl]-L-alanyl-L-proline t-butyl ester (1.7 g 35%) was obtained. The product was purified as maleate salt following the same procedure described in Example 1 (1.45 g, 78%).

N-[(1S)-1-(5-nitrooxyethoxyethoxycarbonyl)-3-phenylpropyl]-L-alanyl-L-proline t-butyl ester maleate (1 g, 1.89 mmol was converted into N-[(1S)-1-(5-nitrooxyethoxyethoxycarbonyl)-3-phenylpropyl]-L-alanyl-L-proline hydrochloride (0.92 g, 94%) as a white, hygroscopic solid following the procedure described in Example 1.

N-[(1S)-1-(5-nitrooxyethoxyethoxycarbonyl)-3-phenylpropyl]-L-alanyl-L-proline hydrochloride (0.92 g) was treated with a pH 4.13 buffer solution and the internal salt was extracted with $CHCl_3$. The organic phase was dried and concentrated then it was dropped into a solution of maleic acid (0.2 g) in $CH_3CN$. After 0.5 h stirring the solution is concentrated and the title compound was grounded with $CHCl_3/Et_2O$ and isolated as a white solid (0.6 g, 60%).

$^1$H-NMR (D2O): 7.26–7.19 (5H, m); 6.21 (2H, s); 4.54 (2H, m); 4.21 (4H, m); 3.84 (1H, m); 3.72 (4H, m), 3.46 (2H, m); 2.70 (2H, m); 2.21 (2H, m); 1.89 (2H, m); 1.49–1.41 (3H, d).

Example 3

Synthesis of N-[(1S)-1-(Ethoxycarbonyl)-3-phenylpropyl]-L-alanyl-L-proline 3-nitrooxypropyl ester hydrogen maleate (corresponding to compound 1)

To a solution of L-Boc-proline (3.23 g. 15 mmol) 3 bromopropanol (1.97 mL, 22.5 mmol) and N,N-dimethylaminopyridine (0.2 g, 1.63 mmol) in methylene chloride (50 mL), cooled at 0° C., a solution of N,N-dicyclohexyl-carbodiimide (3.5 g, 17 mmol) in methylene chloride (50 mL), was slowly added. The reaction was slowly warmed to room temperature and stirred for one hour. The dicyclohexylurea was filtered off and the mother liquor was concentrated and purified by flash chromatography (Hexane/EtOAc 3:1) affording N-Boc-L-proline 3-bromopropyl ester as a pale yellow oil oil (4.8 g, 95%).

To a solution of N-Boc-L-proline 3-bromopropyl ester (4.7 g, 14 mmol) in acetonitrile/THF 1:1 (100 mL) $AgNO_3$ (7.1 g, 42 mmol) was added and the reaction was warmed at 60° C. for 8 hours in the dark. The formed salts were filtered off, the solvent was concentrated and the residue purified by flash chromatography (Hexane/methylene chloride 1:1) affording N-Boc-L-proline 3-nitrooxypropyl ester as an oil (4.1 g, 92%).

To a cooled at 0° C. solution of N-Boc-L-proline 3-nitrooxypropyl ester (2.1 g, 6.6 mmol) in Ethyl acetate (50 mL) a 6.8 M solution of HCl in ethyl acetate (19.4 mL) was added and the solution was slowly warmed to room temperature and stirred for 5 hours. Then the solvent was evaporated affording L-proline 3-nitrooxypropyl ester hydrochloride (1.7 g, quantitative) as a foam.

To a cooled at 0° C. solution of L-proline 3-nitrooxypropyl ester hydrochloride (1.7 g, 6.67 mmol) N-Boc-L-alanine (1.4 mL, 7.4 mmol), TEA (1.85 mL, 13.3 mmol), N,N-dimethylaminopyridine (0.122 g, 1 mmol) in methylene chloride (50 mL) a solution of N,N-dicyclohexylcarbodiimide (2.0 g, 10 mmol) in $CH_2Cl_2$ (50 mL) was slowly added and the reaction was slowly warmed to room temperature and stirred for 3 hours. The dicyclohexylurea was filtered off and the mother liquor was concentrated and purified by flash chromatography (n-Hexane/$Et_2O$ 2:1) affording N-Boc-alanine-L-Proline 3-nitrooxypropyl ester as an oil (1.6 g, 62%).

N-Boc-alanine-L-Proline 3-nitrooxypropyl ester (1.5 g, 3.85 mmol) was transformed in alanine-L-Proline 3-nitrooxypropyl ester hydrochloride (1.1 g, 85%) by acidic hydrolysis with HCl/EtOAc with the same method already described.

To a solution of trifluoromethanesulfonic anhydride (2.6 ml, 15.8 mmol) in $CH_2Cl_2$ (35 mL) cooled at 4° C., a solution of ethyl-R-hydroxy-4-phenyl butyrrate (3 g, 14.4 mmol) and pyridine (1.3 ml, 16.12 mL) was added dropwise in one hour. After stirring for additional 2 hours the solution was washed with water (2×30 mL) and the organic layer was The organic layer was then treated with $Na_2SO_4$ concentrate and the residue was purified by chromatography (n-Hexane/EtOAc 9:1) to afford ethyl-R-trifluoromethansulfonyloxy-4-phenyl butyrrate (2.78 g, 57%) as a colourless oil.

To a solution of alanine-L-Proline 3-nitrooxypropyl ester hydrochloride (1.1 g, 3.37 mmol) obtained as above described, in $CH_2Cl_2$ (50 mL) cooled at 0° C., TEA was added (0.42 g, 4.04 mmol). After 10 minutes cold water was added and the two phases separated. The organic layer was treated with $Na_2SO_4$ then was filtered and cooled to 0° C. again. To this solution a solution of TEA (0.42 g, 4.04 mmol) and ethyl-R-trifluoromethansulfonyloxy-4-phenyl butyrrate (2.3 g, 6.74 mmol) in $CH_2Cl_2$ (50 mL) was added and the resulting solution was stirred for 24 hours. Then was washed with water (2×30 mL) and the organic layer was then treated with $Na_2SO_4$, concentrate and the residue was purified by chromatography ($CH_2Cl_2$ 100 to $CH_2Cl_2$/ethyl ether 1:1) to afford N-[(1S)-1-(ethoxycarbonyl)-3-phenylpropyl]-L-alanyl-L-proline 3-nitrooxypropyl ester (1 g, 61%) as a pale yellow oil.

The compound was then salified with maleic acid (0.266 g, 2.30 mmol) in acetonitrile affording after recrystallization with acetonitrile/diethyl ether 1:1 the title compound (1 g, 80%) as a white solid.

$^1$H-NMR (DMSO): 7.28 (5H, m); 6.10 (2H, s); 4.58 (3H, m); 4.35 (1H, m); 4.15 (4H, m); 4.1 (1H, bs); 3.55 (3H, m); 2.65 (2H, dm); 2.2 (1H, m); 1.9 (7H, m); 1.25 (3H, d); 1.55 (3H, t).

Example 4

Synthesis of N-[(1S)-1-(Ethoxycarbonyl)-3-phenyl-propyl]-L-alanyl-L-proline 3-nitrooxypropyl ester hydrogen maleate (corresponding to compound 1)

To a suspension of 1,1-carbonylimidazole (22 g, 136 mmol) in EtOAc (150 mL) a solution of commercial N-[(1S)-1-(ethoxycarbonyl)-3-phenylpropyl]-L-alanine (20.2 g, 72.32 mmol) in EtOAc (100 mL) was added dropwise in 10 minutes. The resulting solution was stirred at room temperature for 1 hour then L-proline 3-nitrooxypropyl ester (28.8 g, 113 mmol) was added and the mixture was stirred for 16 hours. Then was treated with saturated NaHCO$_3$ and brine. The organic layer was anhydrified with magnesium sulphate and concentrated. The residue was purified by flash chromatography (nHexane/EtOAc 4:6) affording N-[(1S)-1-(ethoxycarbonyl)-3-phenylpropyl]-L-alanyl-L-proline 3-nitrooxypropyl ester (14.2 g, 26%) as a pale yellow oil.

The compound was then salified with maleic acid (3.8 g, 32.6 mmol) in acetonitrile affording after recrystallization with acetonitrile/diethyl ether 1:1 the title compound (14 g, 79%) as a white solid.

Example 5

Synthesis of N-[(1S)-1-(Ethoxycarbonyl)-3-phenyl-propyl]-L-alanyl-L-proline 4-nitrooxybutyl ester hydrogen maleate (corresponding to compound 2)

Starting from N-[(1S)1-(ethoxycarbonyl)-3-phenylpropyl]-L-alanine (4.2 g, 1.49 mmol) and L-proline 4-nitrooxybutyl ester hydrochloride (obtained from N-BOC-proline as a clear oil following the procedure described in Example 6) (4.0 g, 1.49 mmol) following the procedure described in Example 4 the title compound (3.9 g, 42%) was obtained as a white solid.

$^1$H-NMR (DMSO): 7.28 (5H, m); 6.10 (2H, s); 4.58 (3H, m); 4.35 (1H, m); 4.15 (4H, m); 4.1 (1H, bs); 3.55 (3H, m); 2.65 (2H, dm); 2.2 (1H, m); 1.9 (9H, m); 1.25 (3H, d); 1.55 (3H, t).

Example 6

Synthesis of N-[(1S)-1-(Ethoxycarbonyl)-3-phenyl-propyl]-L-lysyl-L-proline 4-nitrooxybutyl ester dihydrochloride (corresponding to Product 97).

L-Boc-Proline (5.00 g, 23.2 mmol) and 4-chloro-1-butanol (2.3 mL, 23.2 mmol) were dissolved in CH$_2$Cl$_2$ (70 mL) and the mixture was cooled to 0° C. N,N-dicyclohexylcarbodiimide (7.20 g, 34.8 mmol) and N,N-dimethylaminopyridine (0.28 g, 2.3 mmol) were added and the reaction was slowly warmed to room temperature and stirred for 12 hours. The dicyclohexylurea was filtered off and the mother liquor was concentrated and purified by flash chromatography (n-hexan/EtOAc 85:15) affording N-Boc-L-proline 4-chlorobutyl ester as a clear oil (4.60 g, 65%).

To a solution of N-Boc-L-proline 4-chlorobutyl ester (1.40 g, 4.6 mmol) in CH$_3$CN (20 mL) AgNO$_3$ (1.90 g, 11.4 mmol) was added and the reaction was warmed at 150° C. for 30 minutes at the microwave. The formed salts were filtered off, the solvent was concentrated and the residue purified by flash chromatography (n-hexan/EtOAc 7:3) affording N-Boc-L-proline 4-nitrooxybutyl ester as a clear oil (1.24 g, 83%).

N-Boc-L-proline 4-nitrooxybutyl ester (1.24 g, 3.7 mmol) was dissolved in CH$_2$Cl$_2$ (20 mL) and HCl gas was bubbled into the solution for 2 hours. Then the mixture was concentrated, affording L-proline 4-nitrooxybutyl ester hydrochloride as a clear oil (1.00 g, quantitative).

Commercial N2-[(1S)-ethoxycarbonyl-3-phenylpropyl]-N6-trifluoroacetyl-L-lysine (5.00 g, 11.6 mmol) was suspended in a NaOH solution (pH=12.5, 150 mL). NaOH (6 M) was slowly added in order to maintain pH=12.5. The solution was stirred at room temperature for 2 hours. Then a solution of Boc$_2$O in H$_2$O (5 mL) was added and the reaction was stirred for 3 hours. The solution was diluted with NaH$_2$PO$_4$ (5%, 150 mL), acidified with HCl (3 N) to pH=3 and extracted with EtOAc (3×200 mL). The organic layer was dried over Na$_2$SO$_4$, filtered and concentrated to yield N2-[(1S)-ethoxycarbonyl-3-phenylpropyl]-N6-BOC-L-lysine (2.6 g, 52%) as a white solid.

To a suspension of N2-[(1S)-Ethoxycarbonyl-3-phenylpropyl]-N6-BOC-L-lysine (1.40 g, 3.1 mmol) in CH$_2$Cl$_2$ (18 mL) TEA (4 mmol) was added and the resulting solution was cooled to 0° C. O-(7-Azabenzotriazol-1-yl)-N,N,N',N'-tetramethyluronium hexafluorophosphate (HATU) (1.80 g, 4.6 mmol) was added and the reaction was slowly warmed to room temperature and stirred for 2 hours. A solution of L-proline 4-nitrooxybutyl ester hydrochloride (1.00 g, 3.7 mmol) in CH$_2$Cl$_2$ (5 mL) was added and the reaction was stirred for 12 hours. Then the reaction was treated with NaH$_2$PO$_4$ (5%, 30 mL). The organic layer was washed with Na$_2$CO$_3$ (10%, 30 mL) and brine, dried over Na$_2$SO$_4$, filtered and concentrated. The crude material was purified by flash chromatography (n-hexane/EtOAc 1:1), affording N-[(1S)-1-(ethoxycarbonyl)-3-phenylpropyl]-L-lysyl(Boc)-L-proline 4-nitrooxybutyl ester (1.20 g, 60%) as a clear oil.

N-[(1S)-1-(ethoxycarbonyl)-3-phenylpropyl]-L-lysyl (BOC)-L-proline 4-nitrooxybutyl ester (1.20 g, 1.9 mmol) was dissolved in CH$_2$Cl$_2$ (20 mL) and HCl gas was bubbled into the solution for 1.5 hours. Then the reaction was concentrated and the residue was treated with Et$_2$O affording the title compound as a highly hygroscopic white powder (1.05 g, 86%).

$^1$H-NMR (MeOD) (2 rotamers): 7.40–7.13 (m, 5H), 4.75–4.47 (m, 3H), 4.43–4.04 (m, 5H), 3.95 (t, 1H), 3.76–3.45 (m, 2H), 3.13–2.93 (m, 2H), 2.93–2.66 (m, 2H), 2.47–2.20 (m, 3H), 2.18–1.91 (m, 5H), 1.91–1.51 (m, 8H), 1.35 (t, 3H).

Example 7

Synthesis of N-[(1S)-1-(ethoxycarbonyl)-3-phenyl-propyl]-L-lysyl-L-proline 3-nitrooxypropyl ester dihydrochloride (corresponding to compound 96)

Starting from N2-[(1S)-ethoxycarbonyl-3-phenylpropyl]-N6-BOC-L-lysine (obtained as described in Example 6) and L-proline 3-nitrooxypropyl ester hydrochloride (obtained as described in Example 3) applying the same procedure described in Example 6) the title compound was obtained as a highly hygroscopic white powder (0.85 g, 28%).

H-NMR (MeOD) (2 rotamers): 7.42–7.11 (m, 5H), 4.76–4.51 (m, 3H), 4.40–4.03 (m, 5H), 3.95 (t, 1H), 3.76–3.43 (m, 2H), 3.15–2.95 (m, 2H), 2.91–2.65 (m, 2H), 2.49–2.20 (m, 3H), 2.15–1.91 (m, 5H), 1.91–1.52 (m, 6H), 1.35 (t, 3H).

Example 8

Synthesis of N-[(1S)-1-(3-Nitrooxypropoxycarbonyl)-3-phenylpropyl]-L-lysyl-L-proline 3-nitrooxypropyl ester dihydrochloride (corresponding to compound 86)

To a suspension of commercial (S)-1-[$N^2$-(1-Carboxy-3-phenylpropyl)-L-lysyl]-L-proline dihydrate (Lisinopril) (5.00 g, 11.3 mmol) in dioxane/water (1:1, 20 mL) was added triethylamine (4.70 mL, 33.7 mmol). The solution was cooled to 0° C. and $Boc_2O$ (2.97 g, 13.6 mmol) was added. The reaction was slowly warmed to room temperature and stirred overnight. The crude (S)-1-[$N^2$-(1-Carboxy-3-phenylpropyl)-L-lysyl(Boc)]-L-proline was lyophilised and used without any further purification.

(S)-1-[$N^2$-(1-Carboxy-3-phenylpropyl)-L-lysyl(Boc)]-L-proline (5.70 g, 11.3 mmol), 3-bromo-1-propanol (8.80 mL, 97.3 mmol) and N,N-dimethylaminopyridine (295 mg, 2.41 mmol) were dissolved in $CH_2Cl_2$ (16 mL). The solution was cooled to 0° C. and 1-(3-dimethylaminopropyl-)3-ethylcarbodiimide hydrochloride (6.96 g, 36.3 mmol) was added. The reaction was slowly warmed to room temperature and stirred for 3 hours. The mixture was partitioned between EtOAc (80 mL) and $NaH_2PO_4$ (5%, 75 mL) and the two phases were separated. The organic phase was washed with $NaH_2PO_4$, $NaHCO_3$ (5%) and brine, dried over $Na_2SO_4$ and concentrated. The crude was purified by flash chromatography (EtOAC/Hexane 1:1) affording N-[(1S)-1-(3-bromopropoxycarbonyl)-3-phenylpropyl]-L-lysyl(BOC)-L-proline 3-bromopropyl ester (1.40 g, 15%) as an oil.

A solution of N-[(1S)-1-(3-bromopropoxycarbonyl)-3-phenylpropyl]-L-lysyl(BOC)-L-proline 3-bromopropyl ester (1.40 g, 1.9 mmol) and $AgNO_3$ (968 mg, 5.70 mmol) in $CH_3CN$ (30 mL) was warmed to 50° C. for 3 hours in the dark. The mixture was diluted with EtOAc and the organic phase was washed with $NaH_2PO_4$ (5%, 3×50 mL), $NaHCO_3$ (5%, 2×50 mL), and brine (2×50 mL), dried over $Na_2SO_4$ and adsorbed on silica. The crude was purified by flash chromatography (Hexane/EtOAc 7:3, then Hexane/EtOAC 1:1) affording N-[(1S)-1-(3-nitrooxypropoxycarbonyl)-3-phenylpropyl]-L-lysyl(BOC)-L-proline 3-nitrooxypropyl ester as a clear oil (1.72 g)

N-[(1S)-1-(3-nitrooxypropoxycarbonyl)-3-phenylpropyl]-L-lysyl(BOC)-L-proline 3-nitrooxypropyl ester (620 mg, 0.87 mmol) was dissolved in $CH_2Cl_2$ (5 mL) and $HCl_{gas}$ was bubbled into the solution for 30 minutes. Then n-hexane was added and N-[(1S)-1-(3-nitrooxypropoxycarbonyl)-3-phenylpropyl]-L-lysyl-L-proline 3-nitrooxypropyl ester dihydrochloride was isolated as a white solid (360 mg, 59%).

NMR ($D_2O$): 7.33–7.20 (m, 5H), 4.55 (m, 4H), 4.40–4.10 (m, 5H), 3.91 (m, 1H), 3.77 (m, 1H), 3.54–3.39 (m, 2H), 2.95 (m, 2H), 2.83–2.69 (m, 2H), 2.37–2.19 (m, 4H), 2.09–1.89 (m, 8H), 1.70–1.56 (m, 2H), 1.48 (m, 2H).

Example 9

Synthesis of N-[(1S)-1-(4-Nitrooxybutoxycarbonyl)-3-phenylpropyl]-L-lysyl-L-proline 4-nitrooxybutyl ester dihydrochloride (corresponding to compound 87)

Starting from (S)-1-[$N^2$-(1-Carboxy-3-phenylpropyl)-L-lysyl(Boc)]-L-proline (obtained as described in Example 8) (5.70 g, 11.3 mmol) and 4-chloro-1-butanol (9.70 mL, 97.3 mmol) applying the procedure described in Example 8 the title compound was isolated as a white solid (590 mg, 61%).

NMR ($D_2O$): 7.33–7.20 (m, 5H), 4.55 (m, 4H), 4.40–4.10 (m, 5H), 3.91 (m, 1H), 3.77 (m, 1H), 3.54–3.39 (m, 2H), 2.95 (m, 2H), 2.83–2.69 (m, 2H), 2.37–2.19 (m, 4H), 2.09–1.89 (m, 12H), 1.70–1.56 (m, 2H), 1.48 (m, 2H).

Example 10

Study on Vascular Tone

The ability of ACE inhibitor nitroderivatives to induce vasorelaxation in comparison to native ACE inhibitors, was tested in vitro in isolated rabbit thoracic aorta preparations (Wanstall J. C. et al., Br. J. Pharmacol., 134:463–472, 2001). Male New Zealand rabbits were anaesthetized with thiopental-Na (50 mg/kg, iv), sacrificed by exsanguinations and then the thorax was opened and the aorta dissected. Single ring preparations (4 mm in length) of thoracic aorta were set up in physiological salt solution (PSS) at 37° C. in small organ chambers (5 ml). The composition of PSS was (mM): NaCl 130, $NaHCO_3$ 14.9, $KH_2PO_4$ 1.2, $MgSO_4$ 1.2, HEPES 10, $CaCl_2$, ascorbic acid 170 and glucose 1.1 (95% $O_2$/5% $CO_2$; pH 7.4). Each ring was mounted under 2 g passive tension in 5 ml organ bath. Isometric tension was recorded with a Grass transducer (Grass FT03) attached to a BIOPAC MP150 System. Preparations were allowed to equilibrate for 1 h, then contracted submaximally with noradrenaline (NA, 1 µM) and, when the contraction was stable, acetylcholine (ACh, 10 µM) was added. A relaxant response to ACh indicated the presence of a functional endothelium. When a stable precontraction was reached, a cumulative concentration-response curve to either of the vasorelaxant agents was obtained in the presence of a functional endothelium. Time intervals between different concentrations were based on the time needed to reach a full response. Moreover, the effect of the soluble guanylyl cyclase inhibitor ODQ (1-H-(1,2,4)-oxadiazol(4,3-a)quinoxalin-1-one) on the dilator responses elicited by the compounds was examined preincubating the aortic rings with ODQ (10 µM) for 20 min. Responses to vasorelaxing agents were measured from the plateau of NA contraction. The $IC_{50}$ (concentration giving 50% reversal of NA contraction) was interpolated from the plots of relaxant-response vs log molar concentration of tested compound.

During the experimental period, the plateau obtained with NA was stable without significant spontaneous loss of contraction in the aortic rings. Under these experimental conditions, the native ACE inhibitor, enalapril, did not produce relaxation at any of the concentration tested, the curve being not different from that built up in presence of vehicle alone.

As shown in Table 1, the nitroderivatives of the invention were able to induce relaxation in a concentration-dependent manner. Furthermore, in experiments performed in presence of ODQ (10 µM), the vasorelaxant responses to all the tested drugs were inhibited.

TABLE 1

| Compound | $IC_{50}$ (µM) ± sem |
|---|---|
| Enalapril | >100 |
| Compound of Ex. 3 | 30.9 ± 8.4 |
| Compound of Ex. 1 | 21.9 ± 6.9 |

$IC_{50}$ is the concentration which inhibits 50% of the response.

Example 11

Effects of Enalapril Nitroderivative on Proteinuria and Renal Disease Progression in Rats with Renal Mass Reduction (RMR)

Sprague-Dawley rats underwent right nephrectomy and ligation of two or tree branches of the main renal artery according to Olson et al. (1982). Twenty one days after the renal ablation, when the animals are proteinuric, rats were divided in 3 groups (RMR) of 10 each and received a daily oral dose of enalapril nitroderivative (Compound of Ex. 3) (50 mg/kg), enalapril (7.5 mg/kg) or vehicle for 90 days. A group of sham operated rats was also included (Sham).

Urinary protein excretion measurements were performed before the treatment and every month thereafter. Twenty-four hour urine samples were collected using metabolic cages and proteinuria was determined by the modified Coomassie Blu G dye-binding assay for the proteins with bovine serum albumin as standard.

As shown in Table 2, repeated treatment with enalapril nitroderivative (Compound of Ex. 3) reduced proteinuria at 3 months differently from the parent compound, enalapril, which shows only a marginal effect.

The results of the present study indicate that in the rat model of renal mass reduction, enalapril nitroderivative reduces proteinuria to a larger extent than enalapril by itself.

TABLE 2

| | Proteinuria (mg/day) ± sem | | | |
| --- | --- | --- | --- | --- |
| Time | Sham | RMR-Vehicle | RMR-Enalapril | RMR-Compound of Ex. 3 |
| Basal | 20.5 ± 1.4 | 15.5 ± 1.5 | 15.7 ± 1.2 | 17.5 ± 1.3 |
| 21 days | 28 ± 1.9 | 69.5 ± 22.8 | 72.4 ± 18.3 | 76.5 ± 20.3 |
| 3rd month | 26.8 ± 3.2 | 347.8 ± 46.1* | 290.5 ± 43.2* | 163.9 ± 29.5*,**,° |

*p < 0.01 vs sham
**p < 0.01 vs RMR-vehicle
°p < 0.05 vs RMR-enalapril

Example 12

Evaluation of ACE activities in CD1 mouse of an enalapril nitroderivative according to the invention (compound of Ex. 3) vs enalapril 3-(nitrooxymethyl)phenyl ester maleate (NO-ENA compound of Ex. 2A reported in U.S. Pat. No. 6,242,432) and enalapril.

CD1 mouse were treated i.v. with a single dose of 3 mg/Kg of enalapril and with a equimolar doses of enalapril nitroderivatives (compound of Ex. 3; 3.6 mg/Kg) and NO-ENA (3.92 mg/Kg). After 30 min, 1, 3, 6 and 24 hours the animal were anaesthetized with tiopental-Na to collect the blood from the vena cava. Heparinized blood samples were centrifuged at 1000 g for 20 min at 4° C. The plasma was stored at −20° C. until the ACE activity measurements. The ACE activity was determined by a spectrophotometric method (Sigma) based on the enzymatic reaction catalysed by ACE, where the FAPGG was hydrolysed to FAP. FAPGG hydrolysis produced a decrease in the absorbance at 340 nm, a marker of ACE activity in the sample.

The results, reported in Table 3, are expressed as % of ACE activity vs basal condition.

TABLE 3

| | ACE Activity (% of activity) | | |
| --- | --- | --- | --- |
| Time | Enalapril | Compound Ex. 3 | NO-ENA |
| 15 min | 4.8 | 2.9 | 5.4 |
| 30 min | 5.1 | 3.7 | 4.8 |
| 1 h | 7.3 | 4.1 | 9.3 |
| 3 hs | 19.6 | 11.1 | 23.6 |
| 6 hs | 50.8 | 49.2 | 55.2 |
| 24 hs | 100 | 83.55 | 90.1 |

Example 13

Effect on L-NAME-Induced Hypertension in Rats of a Nitroxyderivative of Enalapril (Compound Ex. 3) Versus Enalapril Male Wistar rats weighing 225–250 g were used. The rats were divided into two groups. Under halothane anesthesia, radiotelemetry probes were inserted into descending aorta to measure systolic blood pressure (SBP). Baseline blood pressure was recovered (103 mmHg). Both groups were then provided with drinking water supplemented with L-NAME (400 mg/L) for 7 days to induce hypertension. After this treatment all the animals have a SBP of about 140 mmHg. The rats were then treated orally each day with enalapril or an equimolar dose of enalapril-nitroderivative (compound Ex. 3). Blood pressure recordings were made 2 hours after drug administration. The study was continued over three days period of drug administration.

The results reported in table 4 demonstrated that the effects of enalapril-nitroderivative (compound Ex. 3) were superior to those of enalapril.

TABLE 4

| Effects of enalapril-nitroxyderivative (compound Ex. 3) vs enalapril on L-NAME-Induced hypertension | | | |
| --- | --- | --- | --- |
| | Systolic blood pressure (mmHg) | | |
| Day | basal | Enalapril | Compound of Ex. 3 |
| 1st | 140 | 128 | 120 |
| 2nd | 140 | 125 | 117 |
| 3rd | 140 | 120 | 115 |

Example 14

Evaluation of hypotensive properties in SHR rats of enalapril-nitroderivative (compound of Ex. 3) vs enalapril.

Compound of Ex. 3 produced a higher decrease in blood pressure than enalapril after an i.v. bolus injection of equimolar doses in a well established rat model of spontaneous hypertension.

After at least 5 days after surgical catheterization of the arterial and venous femoral, conscious old (>9 months) male SHR rats were injected iv bolus with Enalapril, compound of Ex. 3 (equimolar doses) and vehicle (saline) (0.0335 mL/100 g body weight). Blood pressure and heart rate were recorded before (control period 1 h) and after IV bolus administration for up to 4 h.

Example 15

Evaluation of NO release in rat plasma of an enalapril-nitroderivative according to the invention (compound of Ex. 3) vs enalapril 3-(nitrooxymethyl)phenyl ester maleate (NO-ENA compound of Ex. 2A reported in U.S. Pat. No. 6,242,432).

Rat blood was freshly collected with Na-heparin as anticoagulant from male Sprague Dawley rats weighing about 300–330 g. Blood was immediately centrifuged to obtain plasma. Plasma was incubated for up to 240 min at 37° C. in presence of either compound of Ex. 3 (250 μM) or of NO-ENA (250 μM). At fixed times points samples were withdrawn from the incubation and NOx (nitrites+nitrates), the oxidative products of NO, were determined by GPC (gas phase chemiluminescence).

NOx formation from compound of Ex. 3 and NO-ENA is reported in Table 5.

The results show that the NO-release of compound 3 is much slower than the NO-release of NO-ENA.

TABLE 5

| Time (min) | NOx (μM) | |
| --- | --- | --- |
| | Compound of Ex. 3 | NO-ENA (cfr) |
| 1 | 4.82 ± 2.56 | 6.07 ± 10.5 |
| 30 | 5.83 ± 5.15 | 132.4 ± 75.1 |
| 60 | 6.74 ± 6.53 | 173 ± 53.8 |
| 120 | 7.03 ± 6.67 | 216.3 ± 27.3 |
| 240 | 12.91 ± 7.95 | 290.7 ± 47.8 |

Data are expressed as mean ± SD (n = 3)

The invention claimed is:

1. A compound of general formula (I) or a pharmaceutically acceptable salt or stereoisomer thereof:

$$A—(X_1—ONO_2)_s \quad (I)$$

wherein:
s is an integer equal to 1 or 2;
A is:

1a)

wherein n is an integer from 1 to 6, preferably equal to 1 or 2; $N_0$ is —COO— or —COOR$_0$
wherein $R_0$ is H or a linear or branched ($C_1$–$C_{10}$)-alkyl;
$R_1$ is selected from the group consisting of:

(II)

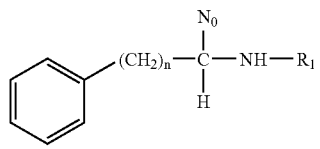

(III)

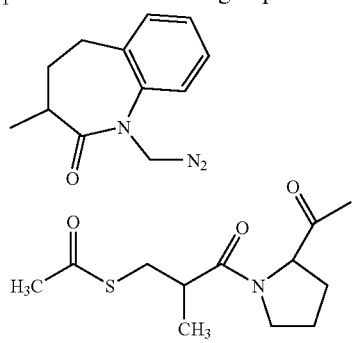

(IV)

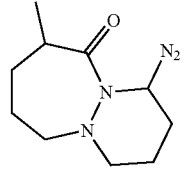

(V)

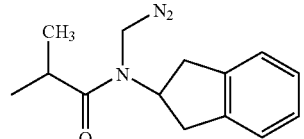

(VI)

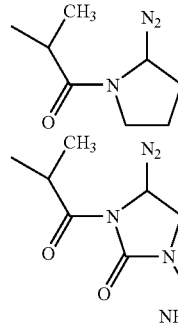

(VII)

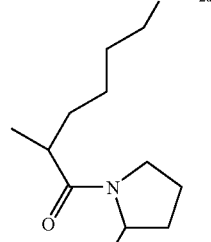

(VIII)

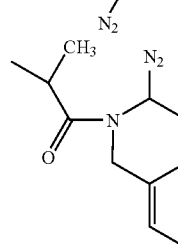

(IX)

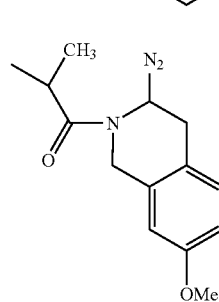

(X)

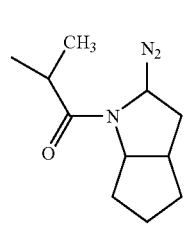

(XI)

-continued

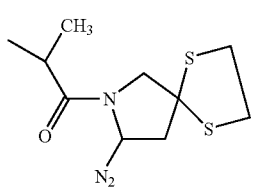
(XII)

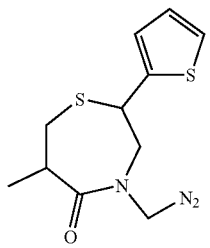
(XIII)

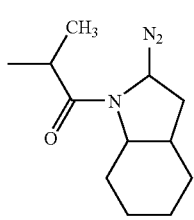
(XIV)

wherein $N_2$ has the same meanings as defined for $N_0$ and they may be equal or different, $N_{2a}$ is H, —C(O)—, —COO—, —COOR$_0$, —C(O)R$_0$— wherein R$_0$ is a linear or branched (C$_1$–C$_{10}$)-alkyl; with the proviso that at least one of the groups $N_0$, $N_2$ or $N_{2a}$ is —COO— or —C(O)— i.e. it has a free valence capable of binding to $X_1$;

$X_1$ is a linear or when possible branched (C$_1$–C$_6$)-alkylene, optionally substituted with at least an halogen atom, or —(CH$_2$—CH$_2$—S)$_2$—;

provided that when A is 1a) and R$_1$ is the group of formula (III) is different from a linear or when possible branched (C$_1$–C$_6$)-alkylene.

2. A compound of general formula (I) or a pharmaceutically acceptable salt or stereoisomer thereof according to claim 1 wherein:

s is as above defined;
A is the following group:

1a)

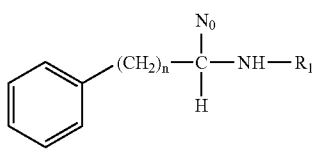

wherein n is an integer equal to 1 or 2; $N_0$ is —COO— or —COOR$_0$ wherein R$_0$ is H or (C$_1$–C$_{10}$)-alkyl;

R$_1$ can be:

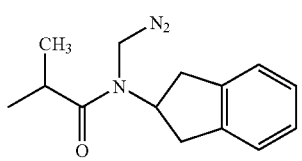
(V)

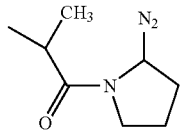
(VI)

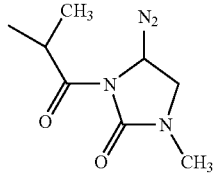
(VII)

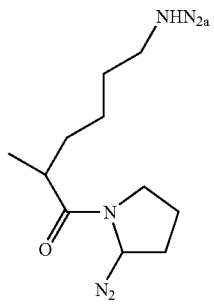
(VIII)

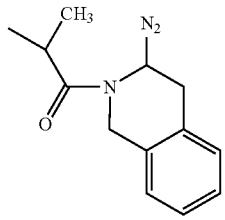
(IX)

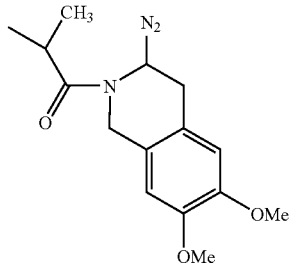
(X)

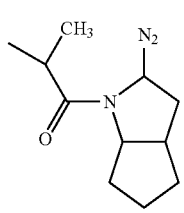
(XI)

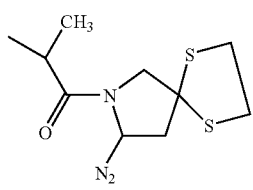
(XII)

-continued (XIV)

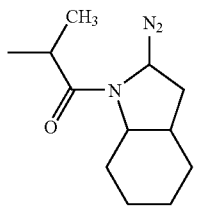

wherein $N_2$ has the same meanings as defined for $N_0$ and they may be equal or different, $N_{2a}$ is H, —C(O)—, —COO—, —COOR$_0$, —C(O)R$_0$ wherein R$_0$ is a linear or branched (C$_1$–C$_{10}$)-alkyl; with the proviso that at least one of the groups $N_0$, $N_2$ or $N_{2a}$ is —COO— or —C(O)— i.e. it has a free valence capable of binding to $X_1$;

$X_1$ is a linear (C$_3$–C$_5$)-alkylene or —(CH$_2$–CH$_2$–S)$_2$—.

3. A compound of general formula (I) or a pharmaceutically acceptable salt or stereoisomer thereof according to claim 1 wherein:

s is 1;
A is:

1a)

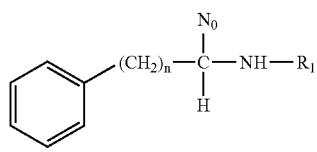

wherein n is 1; $N_0$ is —COO—, that has a free valance capable of binding $X_1$;

$R_1$ is (III)

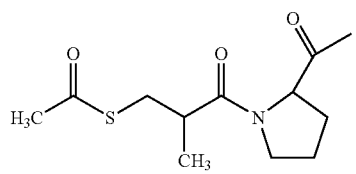

$X_1$ is a bivalent radical equal to —(CH$_2$—CH$_2$—S)$_2$—.

4. A compound of general formula (I) or a pharmaceutically acceptable salt or stereoisomer thereof according to claim 1 wherein:

A is the following group:

1a)

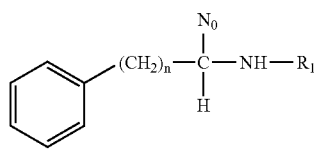

wherein n is 2; $N_0$ is —COO— or —COOR$_0$ wherein R$_0$ is H or (C$_1$–C$_{10}$)-alkyl;

$R_1$ is selected from the group consisting of:

(VI)

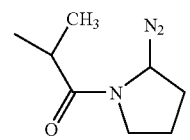

(V)

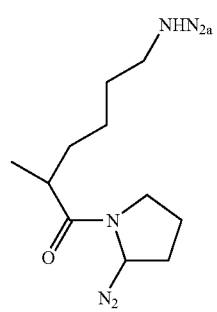

$N_2$ has the same meanings as defined for $N_0$ and they may be equal or different, $N_{2a}$ is H;

with the proviso that at least one of the groups $N_0$ or $N_2$ is —COO—;

$X_1$ is a linear (C$_3$–C$_5$)-alkylene.

5. A compound according to claim 1, selected from the group consisting of:

(1)

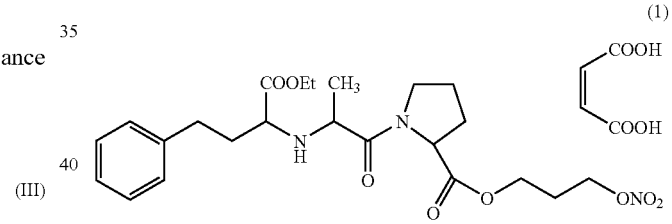

(2)

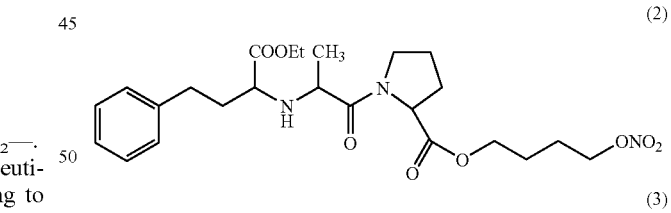

(3)

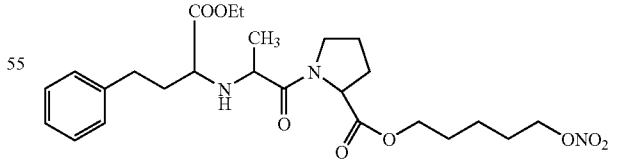

(5)

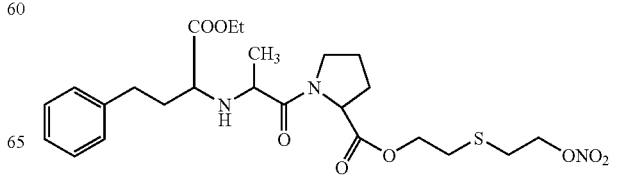

-continued

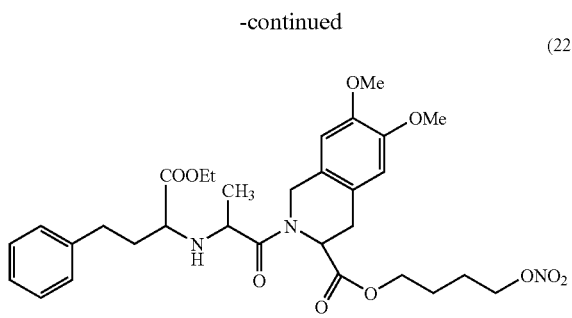
(22)
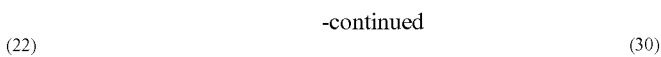
(30)
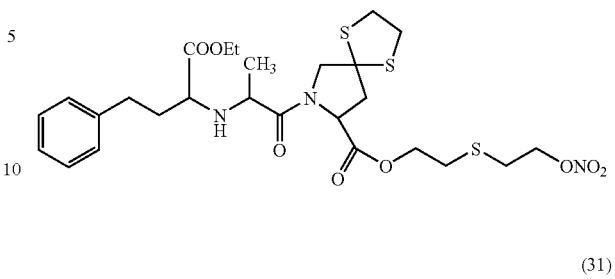
(23)
(31)
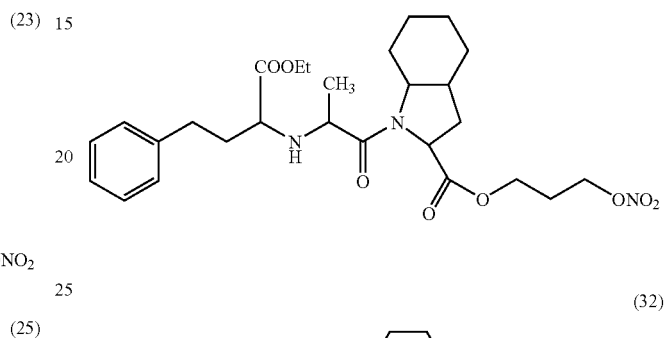
(25)
(32)
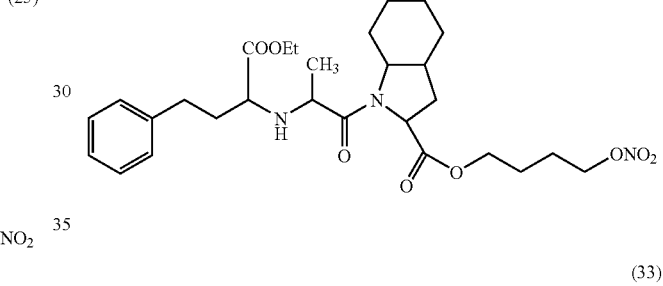
(26)
(33)
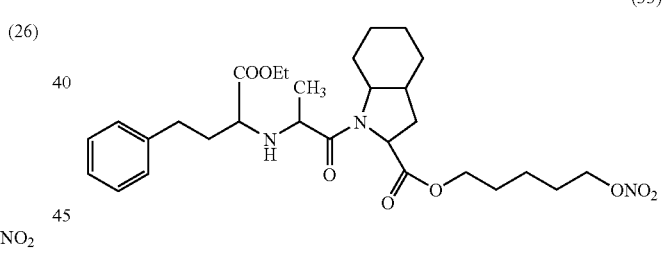
(27)
(35)
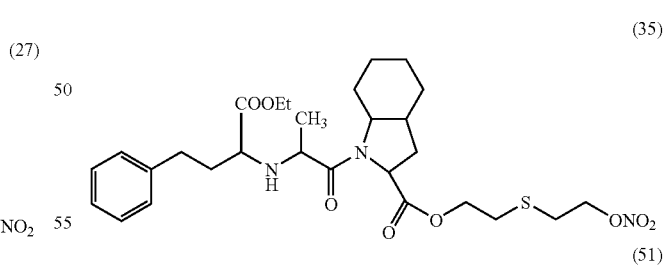
(28)
(51)
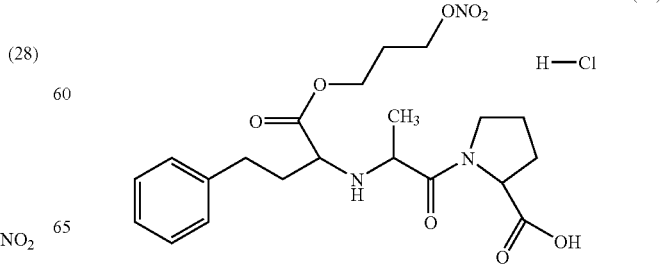

-continued
(52)
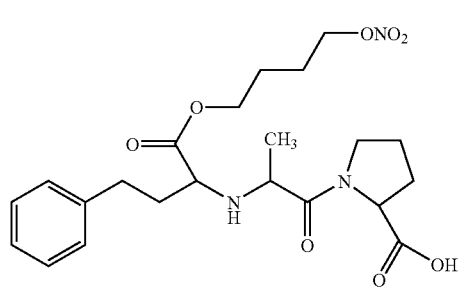
(53)
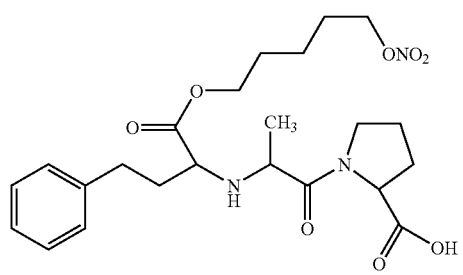
(55)
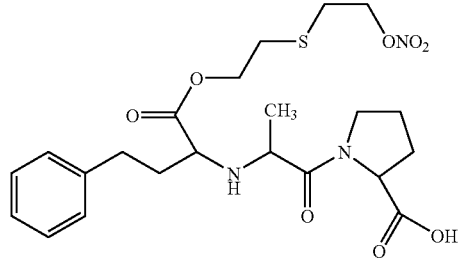
(56)
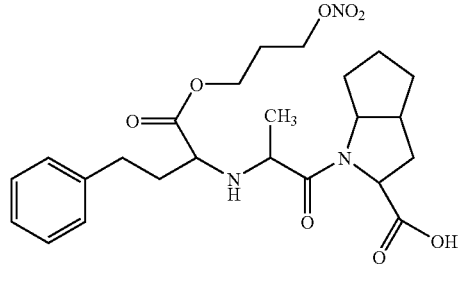
(57)
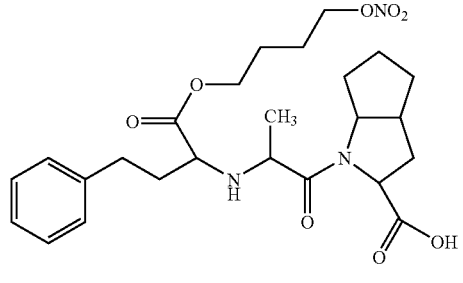
-continued
(58)
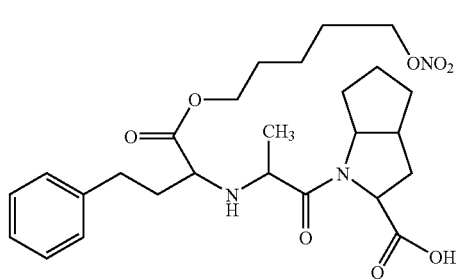
(60)
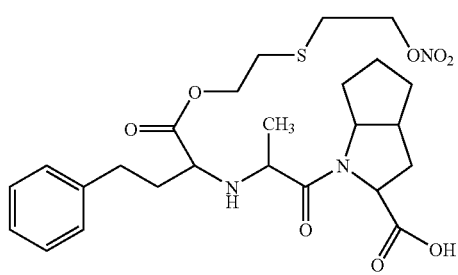
(61)
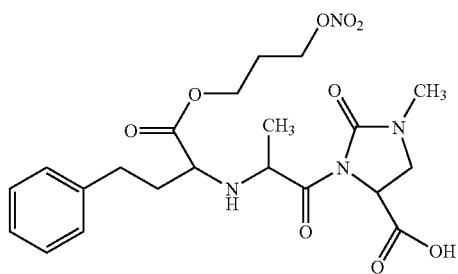
(62)
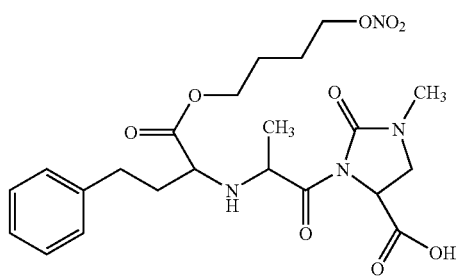
(63)
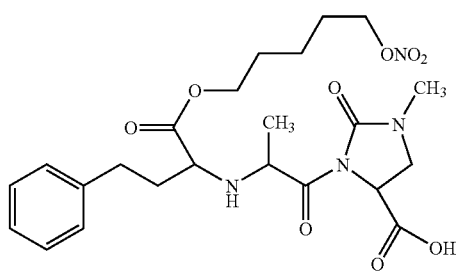
(65)
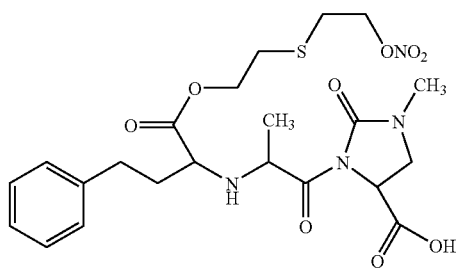

-continued
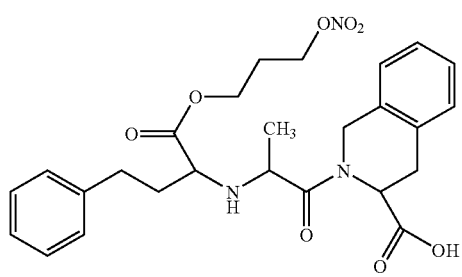
(66)
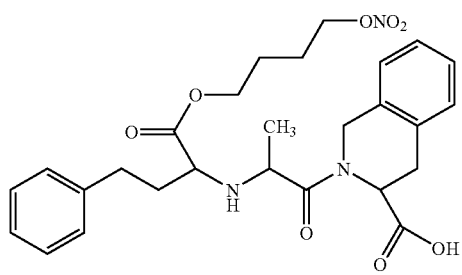
(67)
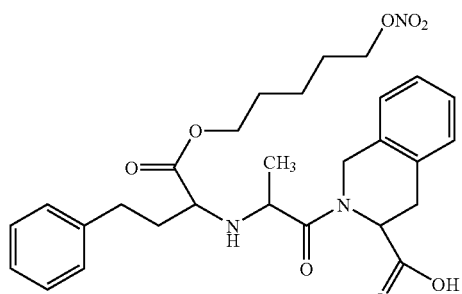
(68)
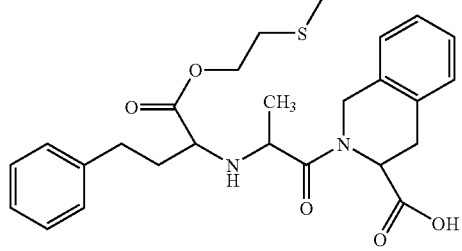
(70)
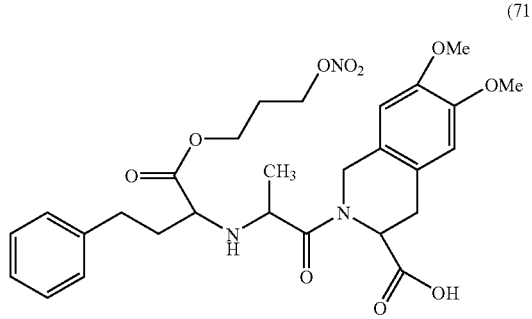
(71)
-continued
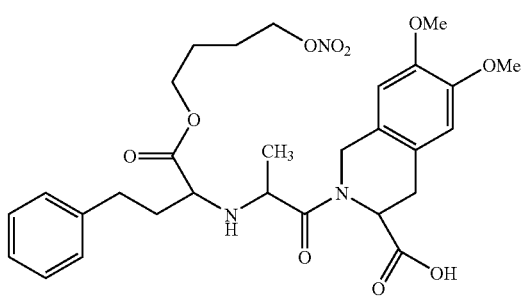
(72)
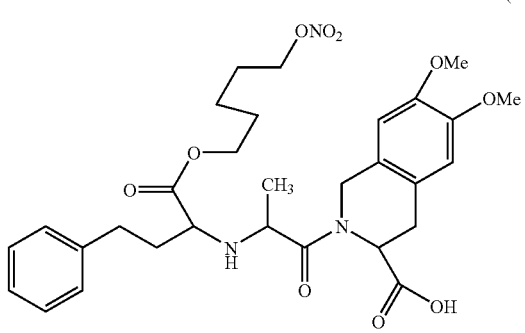
(73)
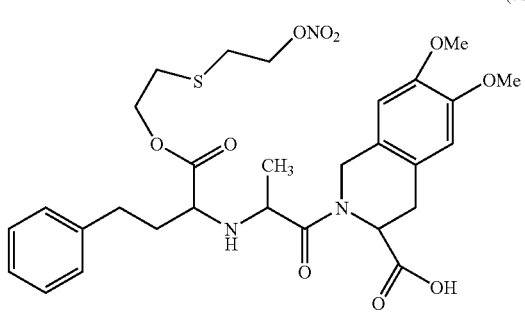
(75)
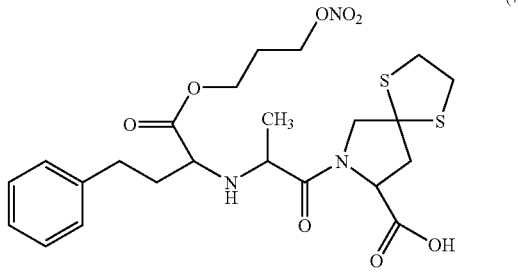
(76)
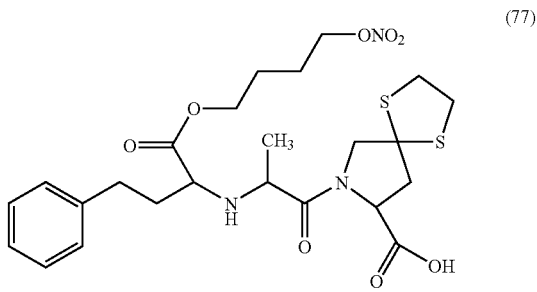
(77)

-continued
(78)
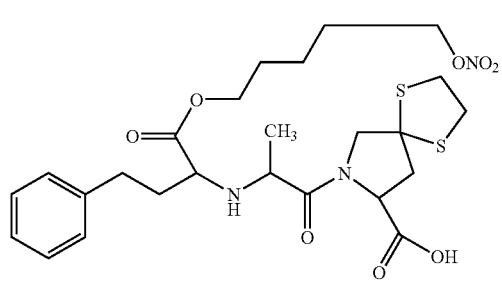
(80)
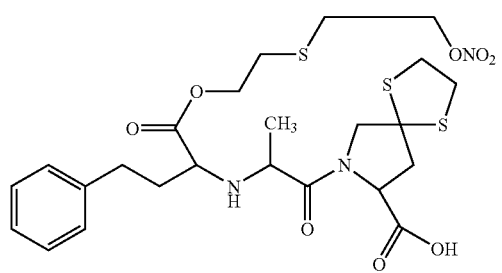
(81)
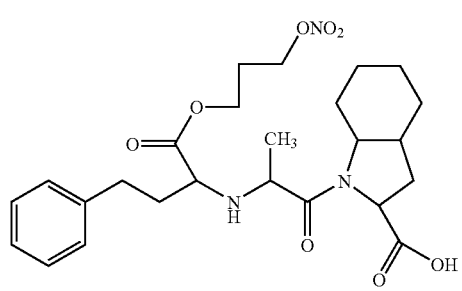
(82)
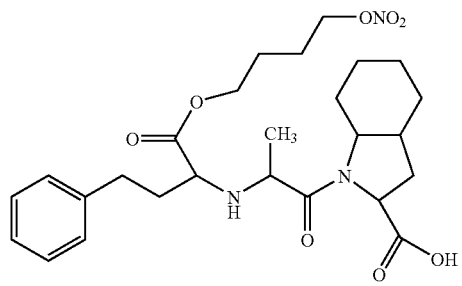
(83)
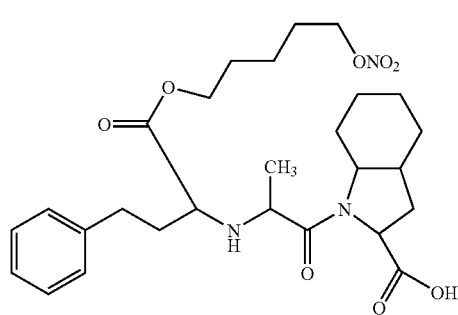
-continued
(85)
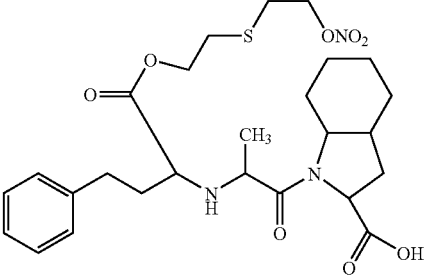
(86)
(87)
(88)

-continued
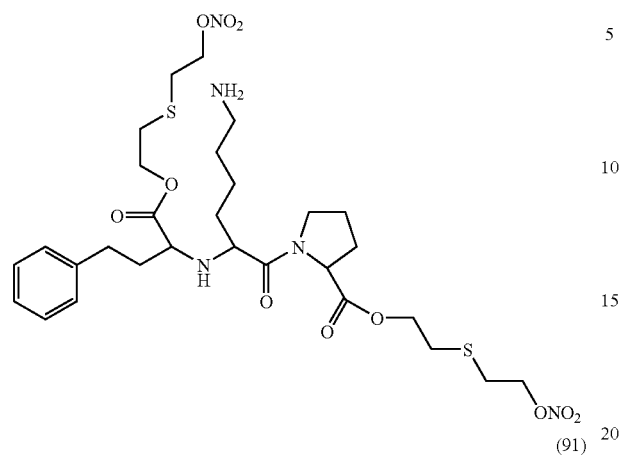
(90)
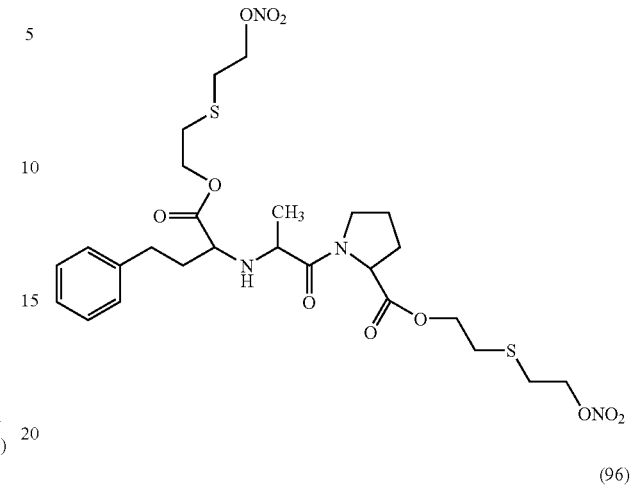
(95)
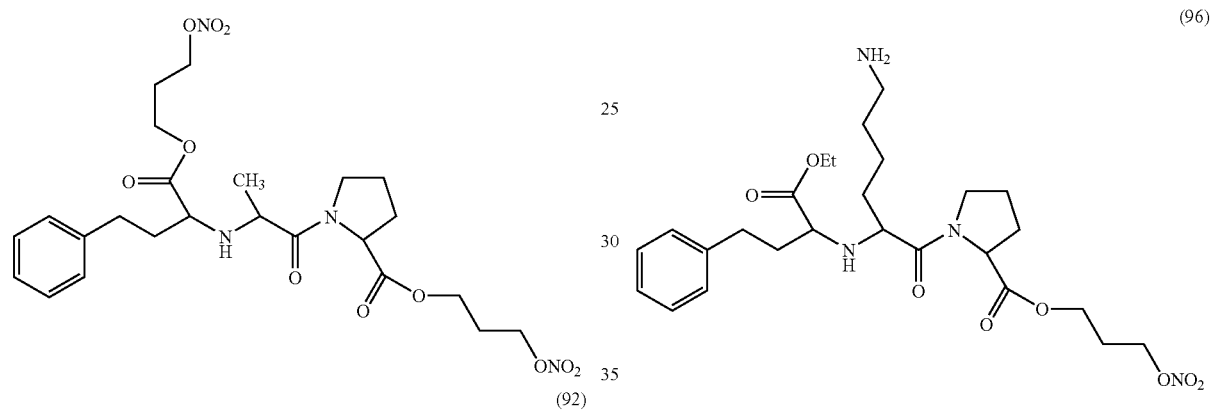
(91)
(92)
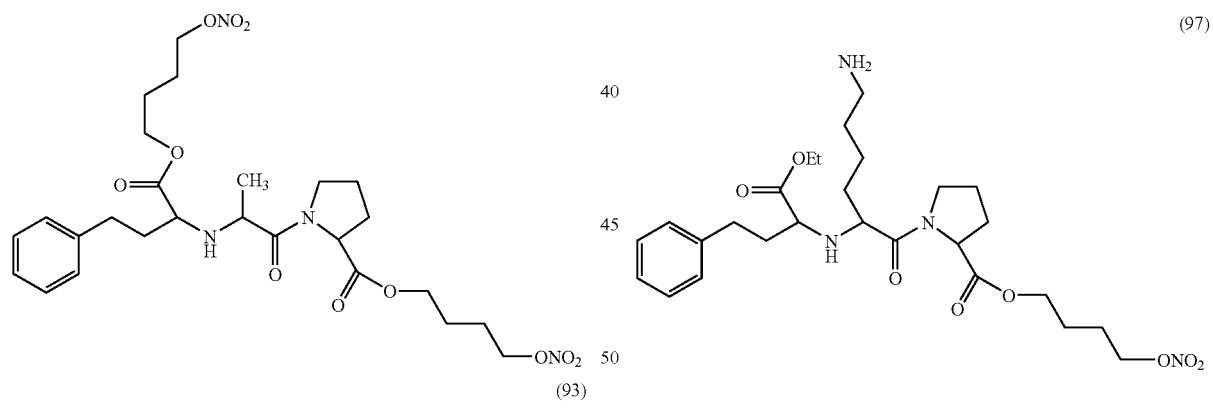
(96)
(97)
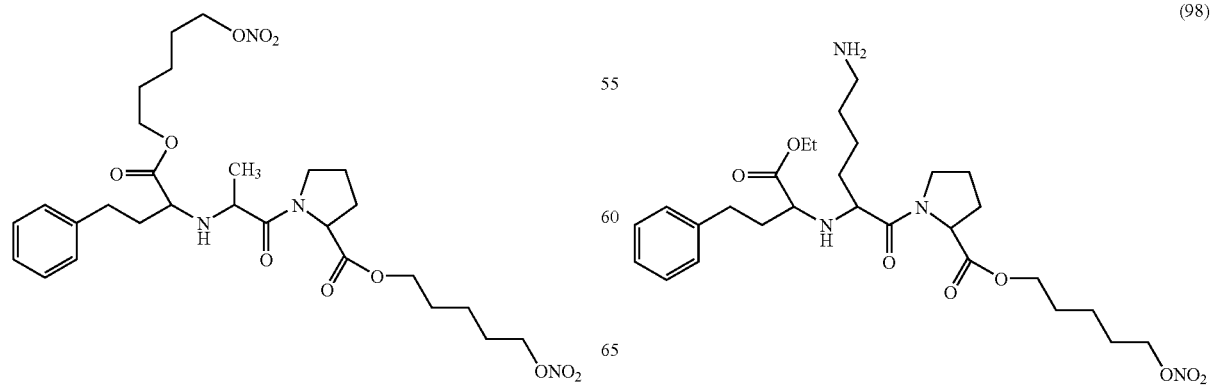
(93)
(98)

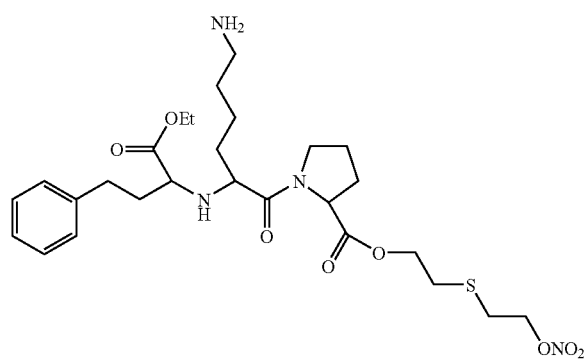
(100)
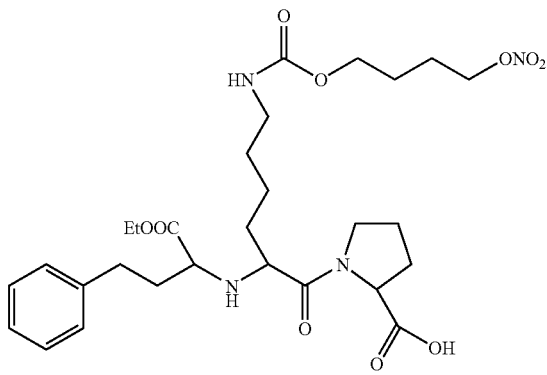
(104)
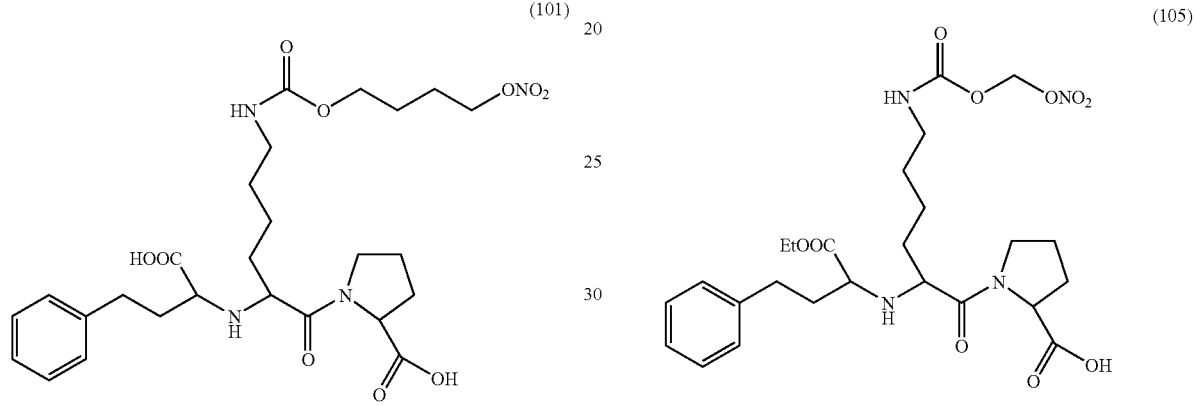
(101)
(105)
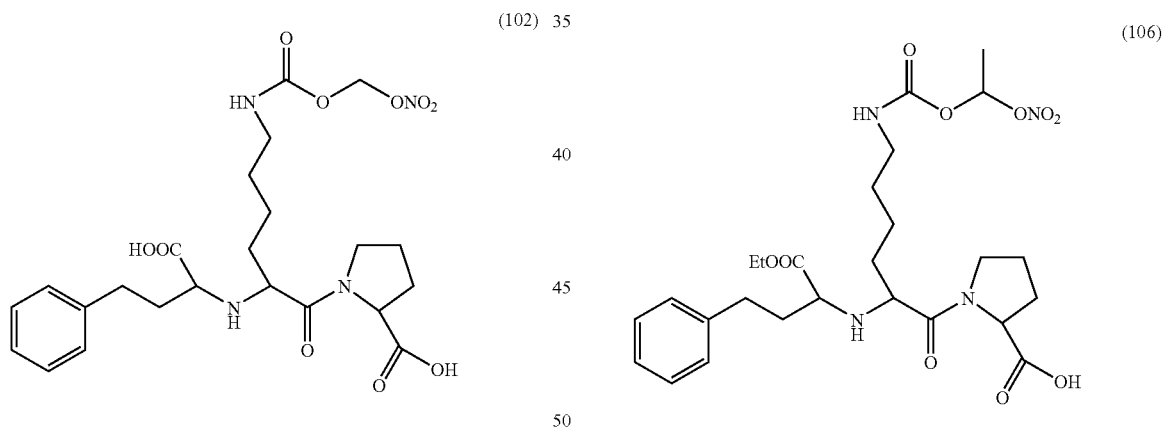
(102)
(106)
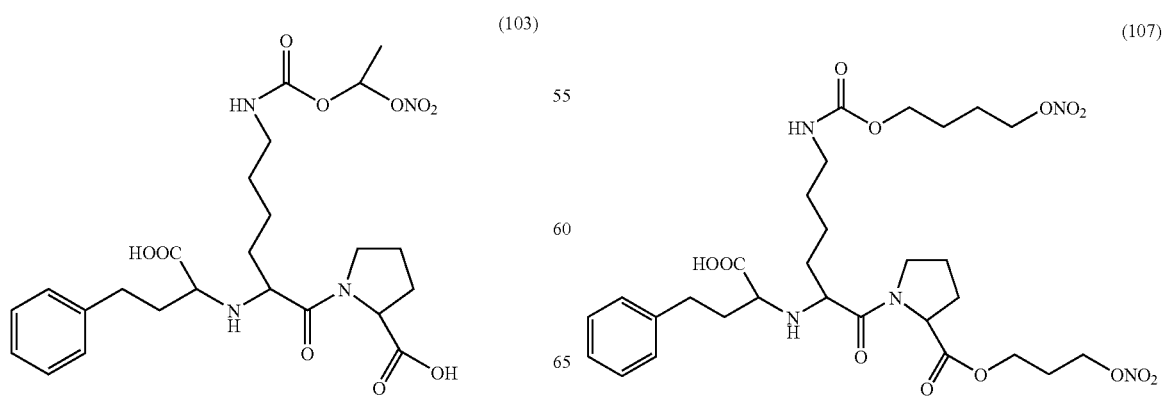
(103)
(107)

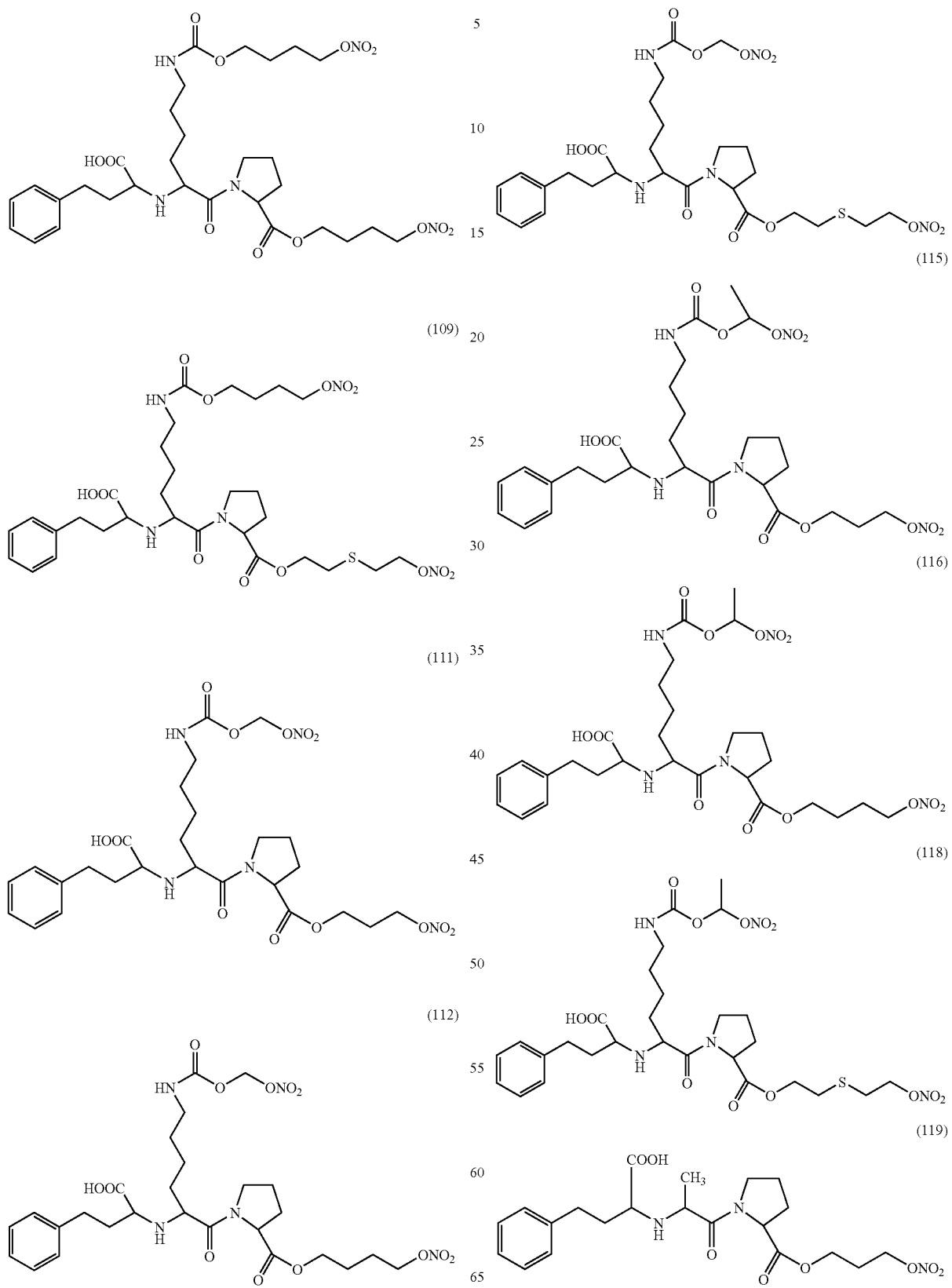

-continued
(120)
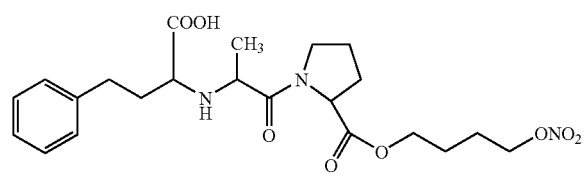
(121)
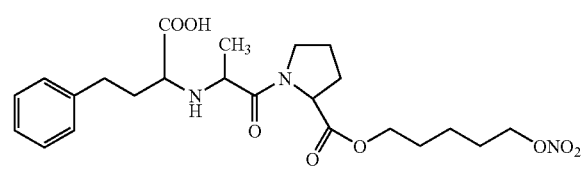
(123)
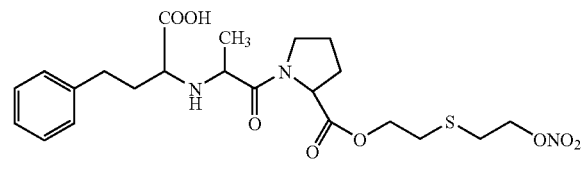
(124)
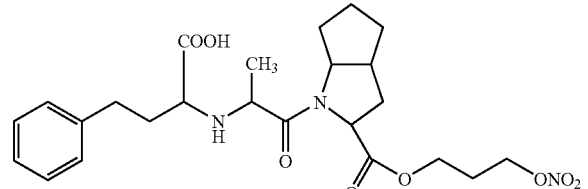
(125)
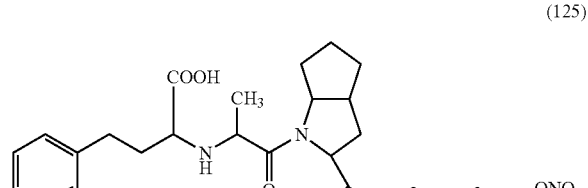
(126)
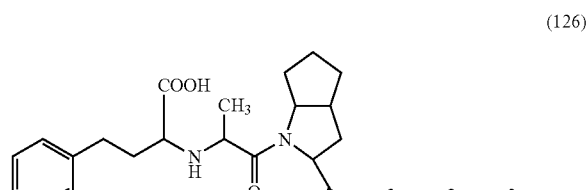
(128)
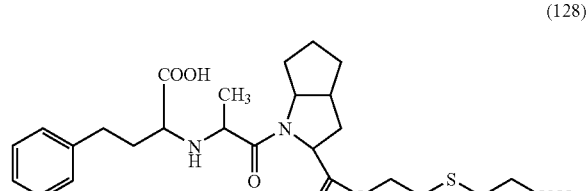
-continued
(129)
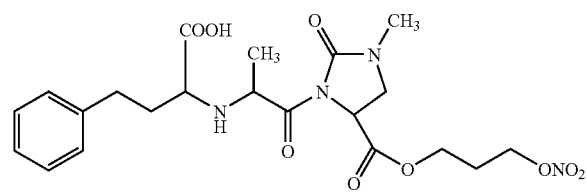
(130)
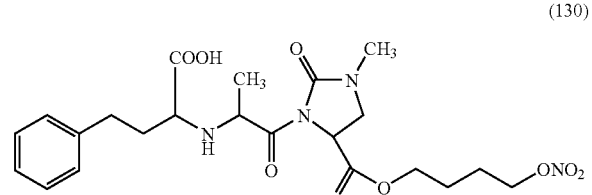
(131)
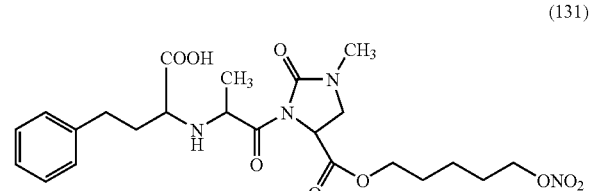
(133)
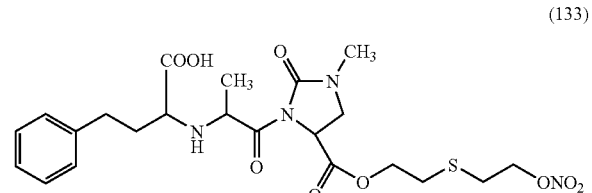
(134)
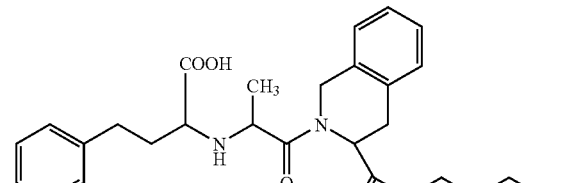
(135)
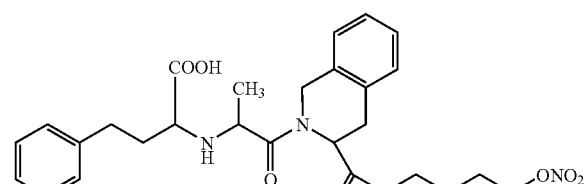
(136)
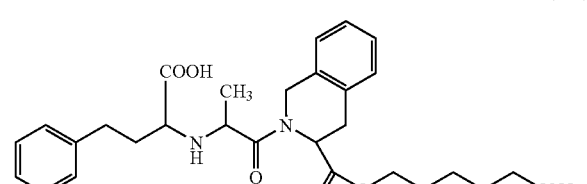

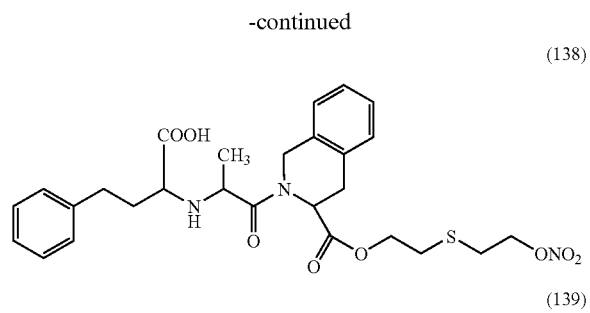
(138)
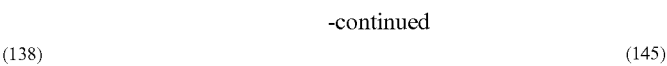
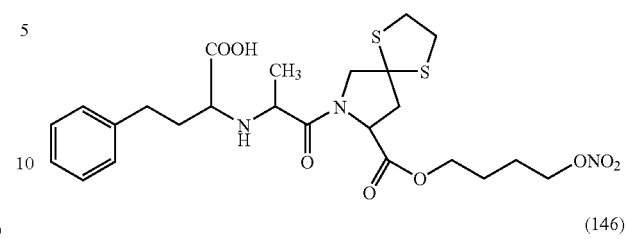
(145)
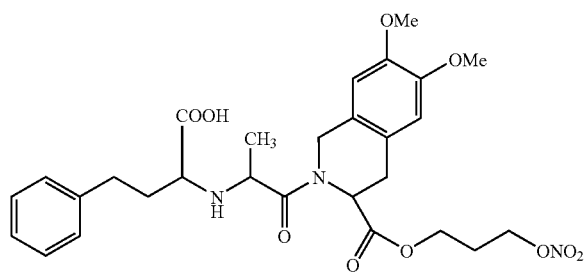
(139)
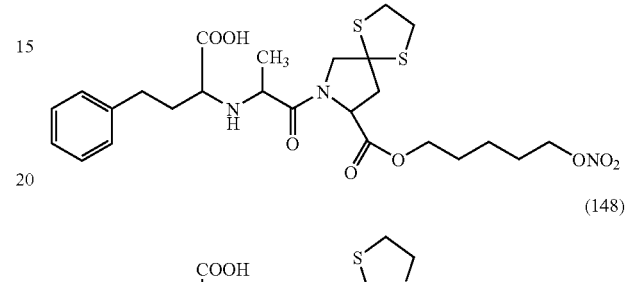
(146)
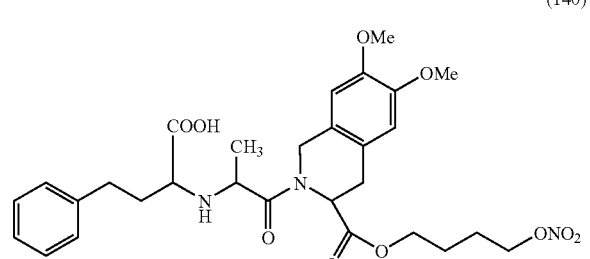
(140)
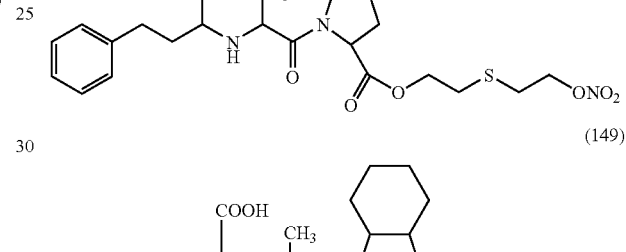
(148)
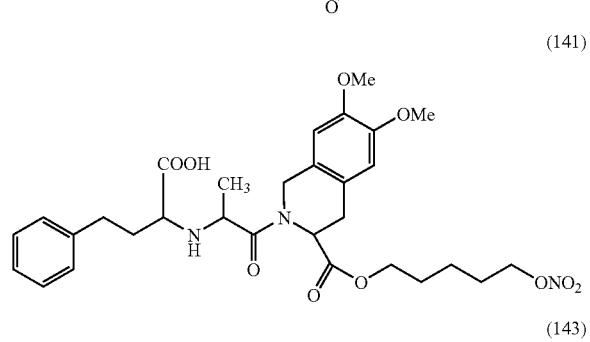
(141)
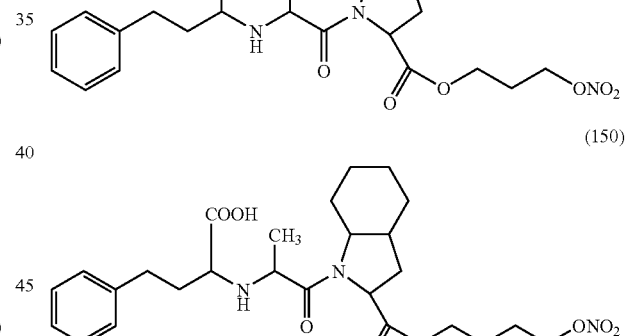
(149)
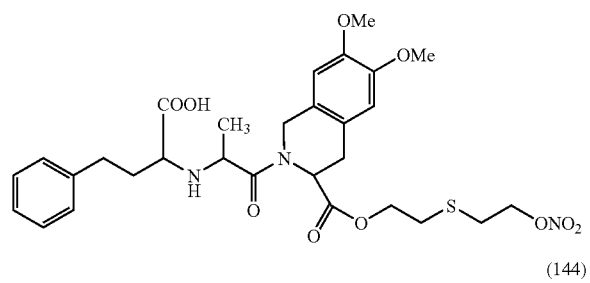
(143)
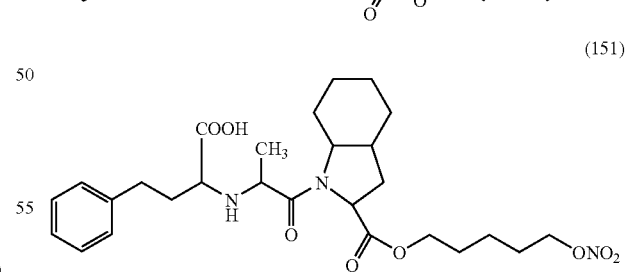
(150)
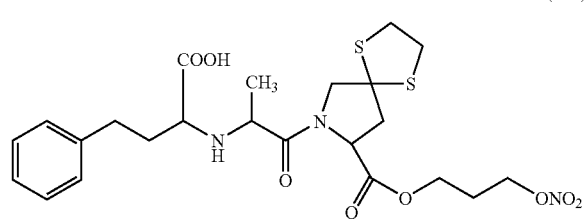
(144)
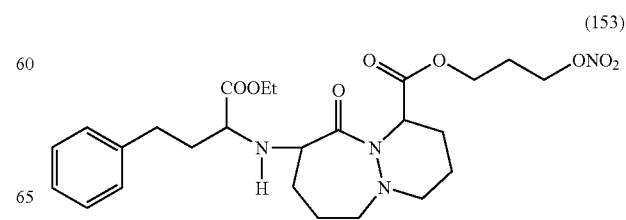
(151)
(153)

6. Compounds according to claim 1 selected from the group consisting of:
- N-[(1S)-1-(3-nitrooxypropoxycarbonyl)-3-phenylpropyl]-L-alanyl-L-proline hydrochloride;
- N-[(1S)-1-(Ethoxycarbonyl)-3-phenylpropyl]-L-alanyl-L-proline 3-nitrooxypropyl ester hydrogen maleate;
- N-[(1S)-1-(Ethoxycarbonyl)-3-phenylpropyl]-L-alanyl-L-proline 4-nitrooxybutyl ester hydrogen maleate;
- N-[(1S)-1-(Ethoxycarbonyl)-3-phenylpropyl]-L-lysyl-L-proline 4-nitrooxybutyl ester dihydrochloride;
- N-[(1S)-1-(ethoxycarbonyl)-3-phenylpropyl]-L-lysyl-L-proline 3-nitrooxypropyl ester dihydrochloride;
- N-[(1S)-1-(3-Nitrooxypropoxycarbonyl)-3-phenylpropyl]-L-lysyl-L-proline 3-nitrooxypropyl ester dihydrochloride;
- N-[(1S)-1-(4-Nitrooxybutoxycarbonyl)-3-phenylpropyl]-L-lysyl-L-proline 4-nitrooxybutyl ester dihydrochloride.

7. A compound of general formula (I) according to claim 1 for use as a medicament.

8. A pharmaceutical composition comprising a pharmaceutically effective amount of a compound of general formula (I) or a salt or stereoisomer thereof according to claim 1 and a pharmaceutically acceptable carrier.

9. A pharmaceutical composition according to claim 8 in a suitable form for the oral, parenteral, rectal, topic and transdermic administration, by inhalation spray or aerosol or iontophoresis devices.

10. Liquid or solid pharmaceutical composition for oral, parenteral, rectal, topic and transdermic administration or inhalation in the form of tablets, capsules and pills eventually with enteric coating, powders, granules, gels, emulsions, solutions, suspensions, syrups, elixir, injectable forms, suppositories, in transdermal patches or liposomes, containing a compound of formula (I) or a salt or stereoisomer thereof according to claim 1 and a pharmaceutically acceptable carrier.

11. Pharmaceutical composition comprising a compound of formula I as defined in claim 1, a compound used to treat cardiovascular disease and a pharmaceutical acceptable carrier.

12. Pharmaceutical composition according to claim 11 wherein the compound used to treat cardiovascular disease is selected from the group consisting of: beta adrenergic blockers, calcium channel blockers, angiotensin II receptor antagonists, antithrombotics, HMGCoA reductase inhibitors, aspirin or nitrooxyderivatives of aspirin, nitrosated beta blockers, nitrosated or nitrosilated calcium channel blockers.

* * * * *